(12) United States Patent
Prouza et al.

(10) Patent No.: US 11,266,850 B2
(45) Date of Patent: Mar. 8, 2022

(54) HIGH POWER TIME VARYING MAGNETIC FIELD THERAPY

(71) Applicant: BTL Healthcare Technologies A.S., Prague (CZ)

(72) Inventors: Ondra Prouza, Ricany u Prahy (CZ); Tomás Schwarz, Prague (CZ)

(73) Assignee: BTL Healthcare Technologies A.S., Prague (CZ)

( * ) Notice: Subject to any disclaimer, the term of this patent is extended or adjusted under 35 U.S.C. 154(b) by 639 days.

(21) Appl. No.: 15/404,384

(22) Filed: Jan. 12, 2017

(65) Prior Publication Data

US 2017/0120067 A1    May 4, 2017

Related U.S. Application Data

(63) Continuation-in-part of application No. 14/926,365, filed on Oct. 29, 2015, now abandoned, which is a continuation-in-part of application No. 14/789,156, filed on Jul. 1, 2015, application No. 15/404,384, which is a continuation-in-part of application No. 14/789,658, filed on Jul. 1, 2015, now Pat. No. 9,636,519.

(60) Provisional application No. 62/441,805, filed on Jan. 3, 2017.

(51) Int. Cl.
*A61N 2/02* (2006.01)
*A61N 2/00* (2006.01)

(52) U.S. Cl.
CPC ............... *A61N 2/02* (2013.01); *A61N 2/008* (2013.01); *A61N 2/004* (2013.01)

(58) Field of Classification Search
CPC .... A61N 2/006; A61N 2/02; A61B 21/00181; A61B 71/0009
USPC ....................................... 600/9–15
See application file for complete search history.

(56) References Cited

U.S. PATENT DOCUMENTS

| | | |
|---|---|---|
| 1,973,387 A | 9/1934 | Neymann et al. |
| 2,021,676 A | 11/1935 | Wood et al. |
| 3,163,161 A | 12/1964 | Courtin |
| 3,566,877 A | 3/1971 | Smith et al. |
| 3,658,051 A | 4/1972 | Maclean et al. |
| 3,841,306 A | 10/1974 | Hallgren et al. |
| 3,915,151 A | 10/1975 | Kraus |
| 3,946,349 A | 3/1976 | Haldeman, III |
| 3,952,751 A | 4/1976 | Yarger |
| 4,068,292 A | 1/1978 | Berry et al. |

(Continued)

FOREIGN PATENT DOCUMENTS

| | | |
|---|---|---|
| AU | 747678 B2 | 5/2002 |
| AU | 2011265424 B2 | 7/2014 |

(Continued)

OTHER PUBLICATIONS

US 10,398,895 B2, 09/2019, Tomás (withdrawn)

(Continued)

*Primary Examiner* — Samuel G Gilbert
(74) *Attorney, Agent, or Firm* — Sterne, Kessler, Goldstein & Fox P.L.L.C.

(57) ABSTRACT

In a method for stimulation and treatment, a biological structure is stimulated by a high power time-varying magnetic field. The stimulation is followed by at least a partial muscle contraction. The methods can be used e.g. in physiotherapy, urology or urogynaecology.

29 Claims, 27 Drawing Sheets

(56) References Cited

U.S. PATENT DOCUMENTS

| | | |
|---|---|---|
| 4,143,661 A | 3/1979 | LaForge et al. |
| 4,237,898 A | 12/1980 | Whalley |
| 4,305,115 A | 12/1981 | Armitage |
| 4,315,503 A | 2/1982 | Ryaby et al. |
| 4,392,040 A | 7/1983 | Rand et al. |
| 4,454,883 A | 6/1984 | Fellus |
| 4,456,001 A | 6/1984 | Pescatore |
| 4,550,714 A | 11/1985 | Talish |
| 4,665,898 A | 5/1987 | Costa et al. |
| 4,674,482 A | 6/1987 | Waltonen et al. |
| 4,674,505 A | 6/1987 | Pauli et al. |
| 4,723,536 A | 2/1988 | Rauscher et al. |
| 4,850,959 A | 7/1989 | Findl |
| 4,889,526 A | 12/1989 | Rauscher et al. |
| 4,957,480 A | 9/1990 | Morenings |
| 4,989,604 A | 2/1991 | Fang |
| 4,993,413 A | 2/1991 | McLeod et al. |
| 5,061,234 A | 10/1991 | Chaney |
| 5,067,940 A | 11/1991 | Liboff et al. |
| 5,085,626 A | 2/1992 | Frey |
| 5,143,063 A | 9/1992 | Fellner |
| 5,156,587 A | 10/1992 | Montone |
| 5,181,902 A | 1/1993 | Erickson et al. |
| 5,199,951 A | 4/1993 | Spears |
| 5,334,181 A | 8/1994 | Rubinsky et al. |
| 5,344,384 A | 9/1994 | Ostrow et al. |
| 5,401,233 A | 3/1995 | Erickson et al. |
| 5,415,617 A | 5/1995 | Kraus |
| 5,419,344 A | 5/1995 | Dewitt |
| 5,433,737 A | 7/1995 | Aimone |
| 5,433,740 A | 7/1995 | Yamaguchi |
| 5,584,863 A | 12/1996 | Rauch et al. |
| 5,660,836 A | 8/1997 | Knowlton |
| 5,674,218 A | 10/1997 | Rubinsky et al. |
| 5,718,662 A | 2/1998 | Jalinous |
| 5,725,471 A | 3/1998 | Davey et al. |
| 5,755,753 A | 5/1998 | Knowlton |
| 5,766,124 A | 6/1998 | Polson |
| 5,782,743 A | 7/1998 | Russell |
| 5,807,232 A | 9/1998 | Espinoza et al. |
| 5,908,444 A | 6/1999 | Azure |
| 5,919,219 A | 7/1999 | Knowlton |
| 5,968,527 A | 10/1999 | Litovitz |
| 5,984,854 A | 11/1999 | Ishikawa et al. |
| 6,017,337 A | 1/2000 | Pira |
| 6,032,675 A | 3/2000 | Rubinsky |
| 6,047,215 A | 4/2000 | Mcclure et al. |
| 6,063,108 A | 5/2000 | Salansky et al. |
| 6,067,474 A | 5/2000 | Schulman et al. |
| 6,086,525 A | 7/2000 | Davey et al. |
| 6,094,599 A | 7/2000 | Bingham et al. |
| 6,099,459 A | 8/2000 | Jacobson |
| 6,099,523 A | 8/2000 | Kim et al. |
| 6,117,066 A | 9/2000 | Abrams et al. |
| 6,132,361 A | 10/2000 | Epstein et al. |
| 6,141,985 A | 11/2000 | Cluzeau et al. |
| 6,155,966 A | 12/2000 | Parker |
| 6,161,757 A | 12/2000 | Morris |
| 6,179,769 B1 | 1/2001 | Ishikawa et al. |
| 6,179,770 B1 | 1/2001 | Mould |
| 6,200,259 B1 | 3/2001 | March |
| 6,213,933 B1 * | 4/2001 | Lin .................. A61N 2/02 600/13 |
| 6,223,750 B1 | 5/2001 | Ishikawa et al. |
| 6,246,905 B1 | 6/2001 | Mogul |
| 6,255,815 B1 | 7/2001 | Davey |
| 6,261,301 B1 | 7/2001 | Knesch et al. |
| 6,273,862 B1 | 8/2001 | Privitera et al. |
| 6,273,884 B1 | 8/2001 | Altshuler et al. |
| 6,280,376 B1 | 8/2001 | Holcomb |
| 6,282,448 B1 | 8/2001 | Katz et al. |
| D447,806 S | 9/2001 | Davey et al. |
| 6,311,090 B1 | 10/2001 | Knowlton |
| 6,324,430 B1 | 11/2001 | Zarinetchi et al. |
| 6,324,432 B1 | 11/2001 | Rigaux et al. |
| 6,334,069 B1 | 12/2001 | George et al. |
| 6,334,074 B1 | 12/2001 | Spertell |
| 6,350,276 B1 | 2/2002 | Knowlton |
| 6,402,678 B1 | 6/2002 | Fischell et al. |
| 6,413,255 B1 | 7/2002 | Stern |
| 6,418,345 B1 | 7/2002 | Tepper et al. |
| 6,425,852 B1 | 7/2002 | Epstein et al. |
| 6,443,883 B1 | 9/2002 | Ostrow et al. |
| 6,453,202 B1 | 9/2002 | Knowlton |
| 6,461,375 B1 | 10/2002 | Baudry et al. |
| 6,491,620 B1 | 12/2002 | Davey |
| 6,500,110 B1 | 12/2002 | Davey et al. |
| 6,520,903 B1 | 2/2003 | Yamashiro |
| 6,527,694 B1 | 3/2003 | Ishikawa et al. |
| 6,527,695 B1 | 3/2003 | Davey et al. |
| 6,537,197 B1 | 3/2003 | Ruohonen et al. |
| 6,569,078 B2 | 5/2003 | Ishikawa et al. |
| 6,605,080 B1 | 8/2003 | Altshuler et al. |
| 6,635,053 B1 | 10/2003 | Lalonde et al. |
| 6,658,301 B2 | 12/2003 | Loeb et al. |
| 6,662,054 B2 | 12/2003 | Kreindel et al. |
| 6,663,556 B2 | 12/2003 | Barker |
| 6,663,659 B2 | 12/2003 | Mcdaniel |
| 6,701,185 B2 | 3/2004 | Burnett et al. |
| 6,735,481 B2 | 5/2004 | Bingham et al. |
| 6,738,667 B2 | 5/2004 | Deno et al. |
| 6,749,624 B2 | 6/2004 | Knowlton |
| 6,827,681 B2 | 12/2004 | Tanner et al. |
| 6,849,040 B2 | 2/2005 | Ruohonen et al. |
| 6,860,852 B2 | 3/2005 | Schonenberger et al. |
| 6,871,099 B1 | 3/2005 | Whitehurst et al. |
| 6,889,090 B2 | 5/2005 | Kreindel |
| 6,920,883 B2 | 7/2005 | Bessette et al. |
| 6,939,287 B1 | 9/2005 | Ardizzone et al. |
| 6,960,202 B2 | 11/2005 | Cluzeau et al. |
| 7,024,239 B2 | 4/2006 | George et al. |
| 7,030,764 B2 | 4/2006 | Smith et al. |
| 7,041,100 B2 | 5/2006 | Kreindel |
| 7,083,580 B2 | 8/2006 | Bernabei |
| 7,186,209 B2 | 3/2007 | Jacobson et al. |
| 7,217,265 B2 | 5/2007 | Hennings et al. |
| 7,276,058 B2 | 10/2007 | Altshuler et al. |
| 7,309,309 B2 | 12/2007 | Wang et al. |
| 7,318,821 B2 | 1/2008 | Lalonde et al. |
| 7,351,252 B2 | 4/2008 | Altshuler et al. |
| 7,367,341 B2 | 5/2008 | Anderson et al. |
| 7,369,895 B2 | 5/2008 | Hurtado |
| 7,372,271 B2 | 5/2008 | Roozen et al. |
| 7,376,460 B2 | 5/2008 | Bernabei |
| 7,396,326 B2 | 7/2008 | Ghiron et al. |
| 7,496,401 B2 | 2/2009 | Bernabei |
| 7,520,849 B1 | 4/2009 | Simon |
| 7,520,875 B2 | 4/2009 | Bernabei |
| 7,532,926 B2 | 5/2009 | Bernabei |
| 7,571,003 B2 | 8/2009 | Pozzato |
| 7,591,776 B2 | 9/2009 | Phillips et al. |
| 7,601,115 B2 | 10/2009 | Riehl |
| 7,608,035 B2 | 10/2009 | Farone |
| 7,618,429 B2 | 11/2009 | Mulholland |
| 7,630,774 B2 | 12/2009 | Karni et al. |
| 7,643,883 B2 | 1/2010 | Kreindel |
| 7,740,574 B2 | 6/2010 | Pilla et al. |
| 7,744,523 B2 | 6/2010 | Epstein |
| 7,783,348 B2 | 8/2010 | Gill et al. |
| 7,785,358 B2 | 8/2010 | Lach |
| 7,854,754 B2 | 12/2010 | Ting et al. |
| 7,909,786 B2 | 3/2011 | Bonnefin et al. |
| 7,914,469 B2 | 3/2011 | Torbati |
| 7,945,321 B2 | 5/2011 | Bernabei |
| 7,946,973 B2 | 5/2011 | Peterchev |
| 7,953,500 B2 | 5/2011 | Bingham et al. |
| 7,998,053 B2 | 8/2011 | Aho |
| 8,035,385 B2 | 10/2011 | Tomiha et al. |
| RE43,007 E | 12/2011 | Lalonde et al. |
| 8,088,058 B2 | 1/2012 | Juliana et al. |
| 8,128,549 B2 | 3/2012 | Testani et al. |
| 8,133,191 B2 | 3/2012 | Rosenberg et al. |
| 8,137,258 B1 | 3/2012 | Dennis et al. |
| 8,172,835 B2 | 5/2012 | Leyh et al. |

(56) References Cited

U.S. PATENT DOCUMENTS

| | | |
|---|---|---|
| 8,192,474 B2 | 6/2012 | Levinson |
| 8,204,446 B2 | 6/2012 | Scheer et al. |
| 8,251,986 B2 | 8/2012 | Chornenky et al. |
| 8,265,763 B2 | 9/2012 | Fahey |
| 8,275,442 B2 | 9/2012 | Allison |
| 8,285,390 B2 | 10/2012 | Levinson et al. |
| 8,335,566 B2 | 12/2012 | Muller et al. |
| 8,337,539 B2 | 12/2012 | Ting et al. |
| 8,366,756 B2 | 2/2013 | Tucek et al. |
| 8,376,825 B2 | 2/2013 | Guinn et al. |
| 8,376,925 B1 | 2/2013 | Dennis et al. |
| 8,454,591 B2 | 6/2013 | Leyh et al. |
| 8,457,751 B2 | 6/2013 | Pozzato |
| 8,523,927 B2 | 9/2013 | Levinson et al. |
| 8,548,599 B2 | 10/2013 | Zarsky et al. |
| 8,565,888 B2 | 10/2013 | Buhlmann et al. |
| 8,579,953 B1 | 11/2013 | Dunbar et al. |
| 8,593,245 B2 | 11/2013 | Zeng et al. |
| 8,603,073 B2 | 12/2013 | Allison |
| 8,646,239 B2 | 2/2014 | Rulon |
| 8,666,492 B2 | 3/2014 | Muller et al. |
| 8,676,338 B2 | 3/2014 | Levinson |
| 8,700,176 B2 | 4/2014 | Azar et al. |
| 8,702,774 B2 | 4/2014 | Baker et al. |
| 8,725,270 B2 | 5/2014 | Towe |
| 8,771,326 B2 | 7/2014 | Myeong et al. |
| 8,834,547 B2 | 9/2014 | Anderson et al. |
| 8,840,608 B2 | 9/2014 | Anderson et al. |
| 8,868,177 B2 | 10/2014 | Simon et al. |
| 8,906,009 B2 | 12/2014 | Nebrigic et al. |
| 8,915,948 B2 | 12/2014 | Altshuler et al. |
| 8,932,338 B2 | 1/2015 | Lim et al. |
| 8,979,727 B2 | 3/2015 | Ron et al. |
| 8,998,791 B2 | 4/2015 | Ron et al. |
| 9,002,477 B2 | 4/2015 | Burnett |
| 9,028,469 B2 | 5/2015 | Jones et al. |
| 9,037,247 B2 | 5/2015 | Simon et al. |
| 9,044,595 B2 | 6/2015 | Araya et al. |
| 9,061,128 B2 | 6/2015 | Hall et al. |
| 9,078,634 B2 | 7/2015 | Gonzales et al. |
| 9,089,719 B2 | 7/2015 | Simon et al. |
| 9,101,524 B2 | 8/2015 | Aghion |
| 9,132,031 B2 | 9/2015 | Levinson et al. |
| 9,149,650 B2 | 10/2015 | Shanks et al. |
| 9,168,096 B2 | 10/2015 | Kreindel |
| 9,261,574 B2 | 2/2016 | Boskamp et al. |
| 9,265,690 B2 | 2/2016 | Kriksunov et al. |
| 9,308,120 B2 | 4/2016 | Anderson et al. |
| 9,314,368 B2 | 4/2016 | Allison et al. |
| 9,326,910 B2 | 5/2016 | Eckhouse et al. |
| 9,339,641 B2 | 5/2016 | Rajguru et al. |
| 9,358,068 B2 | 6/2016 | Schomacker et al. |
| 9,358,149 B2 | 6/2016 | Anderson et al. |
| 9,375,345 B2 | 6/2016 | Levinson et al. |
| 9,387,339 B2 | 7/2016 | Sham et al. |
| 9,398,975 B2 | 7/2016 | Muller et al. |
| 9,408,745 B2 | 8/2016 | Levinson et al. |
| 9,414,759 B2 | 8/2016 | Lang et al. |
| 9,433,797 B2 | 9/2016 | Pilla et al. |
| 9,439,805 B2 | 9/2016 | Gonzales et al. |
| 9,446,258 B1 | 9/2016 | Schwarz et al. |
| 9,468,774 B2 | 10/2016 | Zarsky et al. |
| 9,532,832 B2 | 1/2017 | Ron Edoute et al. |
| 9,545,523 B2 | 1/2017 | Nanda |
| 9,561,357 B2 | 2/2017 | Hall et al. |
| 9,586,057 B2 | 3/2017 | Ladman et al. |
| 9,596,920 B2 | 3/2017 | Shalev et al. |
| 9,610,429 B2 | 4/2017 | Harris et al. |
| 9,610,459 B2 | 4/2017 | Burnett et al. |
| 9,636,516 B2 | 5/2017 | Schwarz |
| 9,636,519 B2 | 5/2017 | Ladman et al. |
| 9,649,220 B2 | 5/2017 | Anderson et al. |
| 9,655,770 B2 | 5/2017 | Levinson et al. |
| 9,694,194 B2 | 7/2017 | Ron Edoute et al. |
| 9,737,434 B2 | 8/2017 | Allison |
| 9,757,584 B2 | 9/2017 | Burnett |
| 9,782,324 B2 | 10/2017 | Crunick et al. |
| 9,814,897 B2 | 11/2017 | Ron Edoute et al. |
| 9,844,460 B2 | 12/2017 | Weber et al. |
| 9,844,461 B2 | 12/2017 | Levinson et al. |
| 9,855,166 B2 | 1/2018 | Anderson et al. |
| 9,861,421 B2 | 1/2018 | O'Neil et al. |
| 9,861,520 B2 | 1/2018 | Baker et al. |
| 9,867,996 B2 | 1/2018 | Zarsky et al. |
| 9,901,743 B2 | 2/2018 | Ron Edoute et al. |
| 9,919,161 B2 | 3/2018 | Schwarz et al. |
| 9,937,358 B2 | 4/2018 | Schwarz et al. |
| 9,962,553 B2 | 5/2018 | Schwarz et al. |
| 9,968,797 B2 | 5/2018 | Sham et al. |
| 9,974,519 B1 | 5/2018 | Schwarz et al. |
| 9,974,684 B2 | 5/2018 | Anderson et al. |
| 9,980,765 B2 | 5/2018 | Avram et al. |
| 9,981,143 B2 | 5/2018 | Ron Edoute et al. |
| 9,999,780 B2 | 6/2018 | Weyh et al. |
| 10,037,867 B2 | 7/2018 | Godyak |
| 10,039,929 B1 | 8/2018 | Schwarz et al. |
| 10,080,906 B2 | 9/2018 | Schwarz |
| 10,092,346 B2 | 10/2018 | Levinson |
| 10,111,770 B2 | 10/2018 | Harris et al. |
| 10,111,774 B2 | 10/2018 | Gonzales et al. |
| 10,124,187 B2 | 11/2018 | Schwarz et al. |
| 10,183,172 B2 | 1/2019 | Ghiron et al. |
| 10,195,453 B2 | 2/2019 | Schwarz et al. |
| 10,195,454 B2 | 2/2019 | Yamashiro |
| 10,201,380 B2 | 2/2019 | Debenedictis et al. |
| 10,245,439 B1 | 4/2019 | Schwarz et al. |
| 10,271,900 B2 | 4/2019 | Marchitto et al. |
| 10,342,988 B2 | 7/2019 | Midorikawa et al. |
| 10,413,745 B2 | 9/2019 | Riehl |
| 10,463,869 B2 | 11/2019 | Ron Edoute et al. |
| 10,471,269 B1 | 11/2019 | Schwarz et al. |
| 10,478,588 B2 | 11/2019 | Walpole et al. |
| 10,478,633 B2 | 11/2019 | Schwarz et al. |
| 10,478,634 B2 | 11/2019 | Schwarz et al. |
| 10,493,293 B2 | 12/2019 | Schwarz et al. |
| 10,518,098 B2 | 12/2019 | Hong et al. |
| 10,549,109 B2 | 2/2020 | Schwarz et al. |
| 10,549,110 B1 | 2/2020 | Schwarz et al. |
| 10,556,121 B2 | 2/2020 | Gurfein |
| 10,556,122 B1 | 2/2020 | Schwarz et al. |
| 10,569,094 B2 | 2/2020 | Schwarz et al. |
| 10,569,095 B1 | 2/2020 | Schwarz et al. |
| 10,583,287 B2 | 3/2020 | Schwarz |
| 10,596,386 B2 | 3/2020 | Schwarz et al. |
| 10,610,696 B1 | 4/2020 | Peled |
| 10,632,321 B2* | 4/2020 | Schwarz ................. A61N 2/02 |
| 10,639,490 B2 | 5/2020 | Simon et al. |
| 10,661,093 B2 | 5/2020 | Ron Edoute et al. |
| 10,675,819 B2 | 6/2020 | Li et al. |
| 10,688,310 B2 | 6/2020 | Schwarz et al. |
| 10,695,575 B1 | 6/2020 | Schwarz et al. |
| 10,695,576 B1 | 6/2020 | Schwarz et al. |
| 10,709,894 B2 | 7/2020 | Schwarz et al. |
| 10,709,895 B2 | 7/2020 | Schwarz et al. |
| 10,806,943 B2 | 10/2020 | Sokolowski |
| 10,821,295 B1 | 11/2020 | Schwarz et al. |
| 2001/0031906 A1 | 10/2001 | Ishikawa et al. |
| 2002/0010414 A1 | 1/2002 | Coston et al. |
| 2002/0160436 A1 | 10/2002 | Markov et al. |
| 2002/0165590 A1 | 11/2002 | Crowe et al. |
| 2003/0028072 A1 | 2/2003 | Fischell et al. |
| 2003/0032950 A1 | 2/2003 | Altshuler et al. |
| 2003/0074037 A1 | 4/2003 | Moore et al. |
| 2003/0130711 A1 | 7/2003 | Pearson et al. |
| 2003/0149451 A1 | 8/2003 | Chomenky et al. |
| 2003/0153958 A1 | 8/2003 | Yamazaki et al. |
| 2003/0158585 A1 | 8/2003 | Burnett |
| 2004/0015163 A1 | 1/2004 | Buysse et al. |
| 2004/0093042 A1 | 5/2004 | Altshuler et al. |
| 2004/0162583 A1 | 8/2004 | Bingham et al. |
| 2004/0193003 A1 | 9/2004 | Mechlenburg et al. |
| 2004/0206365 A1 | 10/2004 | Knowlton |
| 2004/0210214 A1 | 10/2004 | Knowlton |
| 2004/0230226 A1 | 11/2004 | Bingham et al. |

(56) References Cited

U.S. PATENT DOCUMENTS

| | | |
|---|---|---|
| 2005/0049543 A1 | 3/2005 | Anderson et al. |
| 2005/0075701 A1 | 4/2005 | Shafer |
| 2005/0075702 A1 | 4/2005 | Shafer |
| 2005/0134193 A1 | 6/2005 | Myers et al. |
| 2005/0203504 A1 | 9/2005 | Wham et al. |
| 2005/0215987 A1 | 9/2005 | Slatkine |
| 2005/0216062 A1 | 9/2005 | Herbst |
| 2006/0020236 A1 | 1/2006 | Ben-Nun |
| 2006/0036300 A1 | 2/2006 | Kreindel |
| 2006/0106375 A1 | 5/2006 | Werneth et al. |
| 2006/0152301 A1 | 7/2006 | Rohwedder |
| 2006/0184214 A1 | 8/2006 | Mcdaniel |
| 2006/0187607 A1 | 8/2006 | Mo |
| 2006/0195168 A1 | 8/2006 | Dunbar et al. |
| 2006/0199992 A1 | 9/2006 | Eisenberg et al. |
| 2006/0206103 A1 | 9/2006 | Altshuler et al. |
| 2006/0206180 A1 | 9/2006 | Alcidi |
| 2006/0253176 A1 | 11/2006 | Caruso et al. |
| 2006/0259102 A1 | 11/2006 | Slatkine |
| 2006/0271028 A1 | 11/2006 | Altshuler et al. |
| 2006/0287566 A1 | 12/2006 | Zangen et al. |
| 2007/0010766 A1 | 1/2007 | Gil et al. |
| 2007/0083237 A1 | 4/2007 | Teruel |
| 2007/0088413 A1 | 4/2007 | Weber et al. |
| 2007/0135811 A1 | 6/2007 | Hooven |
| 2007/0173749 A1 | 7/2007 | Williams et al. |
| 2007/0173805 A1 | 7/2007 | Weinberg et al. |
| 2007/0232966 A1 | 10/2007 | Applebaum et al. |
| 2007/0244530 A1 | 10/2007 | Ren |
| 2007/0255355 A1 | 11/2007 | Altshuler et al. |
| 2007/0260107 A1 | 11/2007 | Mishelevich et al. |
| 2007/0270795 A1 | 11/2007 | Francischelli et al. |
| 2007/0282156 A1 | 12/2007 | Konings |
| 2007/0293911 A1 | 12/2007 | Crowe et al. |
| 2008/0009885 A1 | 1/2008 | Del Giglio |
| 2008/0082094 A1 | 4/2008 | Mcpherson et al. |
| 2008/0132971 A1 | 6/2008 | Pille et al. |
| 2008/0183251 A1 | 7/2008 | Azar et al. |
| 2008/0228520 A1 | 9/2008 | Day et al. |
| 2008/0234534 A1 | 9/2008 | Mikas et al. |
| 2008/0249350 A1 | 10/2008 | Marchitto et al. |
| 2008/0255572 A1 | 10/2008 | Zeller et al. |
| 2008/0255637 A1 | 10/2008 | Oishi |
| 2008/0262287 A1 | 10/2008 | Dussau |
| 2008/0262574 A1 | 10/2008 | Briefs et al. |
| 2008/0287948 A1 | 11/2008 | Newton et al. |
| 2008/0306325 A1 | 12/2008 | Burnett et al. |
| 2008/0306326 A1 | 12/2008 | Epstein |
| 2008/0312647 A1 | 12/2008 | Knopp et al. |
| 2009/0005631 A1 | 1/2009 | Simenhaus et al. |
| 2009/0018384 A1 | 1/2009 | Boyden et al. |
| 2009/0018628 A1 | 1/2009 | Burns et al. |
| 2009/0024192 A1 | 1/2009 | Mulholland |
| 2009/0036958 A1 | 2/2009 | Mehta |
| 2009/0043293 A1 | 2/2009 | Pankratov et al. |
| 2009/0108969 A1 | 4/2009 | Sims et al. |
| 2009/0149930 A1 | 6/2009 | Schenck |
| 2009/0156958 A1 | 6/2009 | Mehta et al. |
| 2009/0221938 A1 | 9/2009 | Rosenberg et al. |
| 2009/0227831 A1 * | 9/2009 | Burnett .................... A61N 2/02 600/13 |
| 2009/0248004 A1 | 10/2009 | Altshuler et al. |
| 2009/0254154 A1 | 10/2009 | De et al. |
| 2009/0284339 A1 | 11/2009 | Choi et al. |
| 2009/0306648 A1 | 12/2009 | Podhajsky et al. |
| 2009/0326571 A1 | 12/2009 | Mulholland |
| 2010/0004536 A1 | 1/2010 | Rosenberg |
| 2010/0004715 A1 | 1/2010 | Fahey |
| 2010/0016761 A1 | 1/2010 | Rosenberg |
| 2010/0036368 A1 | 2/2010 | England et al. |
| 2010/0049188 A1 | 2/2010 | Nelson et al. |
| 2010/0069704 A1 * | 3/2010 | Peterchev .............. A61N 2/006 600/14 |
| 2010/0081971 A1 | 4/2010 | Allison |
| 2010/0087699 A1 | 4/2010 | Peterchev |
| 2010/0087816 A1 | 4/2010 | Roy |
| 2010/0121131 A1 | 5/2010 | Mathes |
| 2010/0130945 A1 | 5/2010 | Laniado et al. |
| 2010/0145399 A1 | 6/2010 | Johari et al. |
| 2010/0152522 A1 | 6/2010 | Roth et al. |
| 2010/0160712 A1 | 6/2010 | Burnett et al. |
| 2010/0168501 A1 | 7/2010 | Burnett et al. |
| 2010/0179372 A1 | 7/2010 | Glassman |
| 2010/0217253 A1 | 8/2010 | Mehta |
| 2010/0222629 A1 | 9/2010 | Burnett et al. |
| 2010/0228250 A1 | 9/2010 | Brogna |
| 2010/0274329 A1 | 10/2010 | Bradley et al. |
| 2010/0286691 A1 | 11/2010 | Kerr et al. |
| 2010/0309689 A1 | 12/2010 | Coulson |
| 2010/0324611 A1 | 12/2010 | Deming et al. |
| 2010/0331603 A1 | 12/2010 | Szecsi |
| 2011/0004261 A1 | 1/2011 | Sham et al. |
| 2011/0007745 A1 | 1/2011 | Schultz et al. |
| 2011/0009737 A1 | 1/2011 | Manstein |
| 2011/0015464 A1 | 1/2011 | Riehl et al. |
| 2011/0021863 A1 | 1/2011 | Burnett et al. |
| 2011/0046432 A1 | 2/2011 | Simon et al. |
| 2011/0046523 A1 | 2/2011 | Altshuler et al. |
| 2011/0077451 A1 | 3/2011 | Marchitto et al. |
| 2011/0082383 A1 | 4/2011 | Cory et al. |
| 2011/0112520 A1 | 5/2011 | Michael |
| 2011/0125203 A1 | 5/2011 | Simon et al. |
| 2011/0130618 A1 | 6/2011 | Ron et al. |
| 2011/0130713 A1 | 6/2011 | Dufay |
| 2011/0130796 A1 | 6/2011 | Louise |
| 2011/0152967 A1 | 6/2011 | Simon et al. |
| 2011/0172735 A1 | 7/2011 | Johari |
| 2011/0172752 A1 | 7/2011 | Bingham et al. |
| 2011/0190569 A1 | 8/2011 | Simon et al. |
| 2011/0202058 A1 | 8/2011 | Eder et al. |
| 2011/0218464 A1 | 9/2011 | Iger |
| 2011/0245900 A1 | 10/2011 | Turner et al. |
| 2011/0263925 A1 | 10/2011 | Bratton |
| 2011/0306943 A1 | 12/2011 | Dunbar et al. |
| 2012/0016359 A1 | 1/2012 | Podhajsky |
| 2012/0029394 A1 | 2/2012 | Babaev |
| 2012/0046598 A1 | 2/2012 | Kardos et al. |
| 2012/0046653 A1 | 2/2012 | Welches et al. |
| 2012/0053449 A1 | 3/2012 | Moses |
| 2012/0109241 A1 | 5/2012 | Rauscher |
| 2012/0116271 A1 | 5/2012 | Caruso et al. |
| 2012/0150079 A1 | 6/2012 | Rosenberg |
| 2012/0157747 A1 | 6/2012 | Rybski et al. |
| 2012/0158100 A1 | 6/2012 | Schomacker |
| 2012/0226272 A1 | 9/2012 | Chernov et al. |
| 2012/0240940 A1 | 9/2012 | Paraschac et al. |
| 2012/0245483 A1 | 9/2012 | Lundqvist |
| 2012/0271206 A1 | 10/2012 | Shalev et al. |
| 2012/0271294 A1 | 10/2012 | Barthe et al. |
| 2012/0277587 A1 | 11/2012 | Adanny et al. |
| 2012/0302821 A1 | 11/2012 | Burnett |
| 2012/0310033 A1 | 12/2012 | Muntermann |
| 2012/0310311 A1 | 12/2012 | Elkah |
| 2013/0012755 A1 | 1/2013 | Slayton |
| 2013/0030239 A1 | 1/2013 | Weyh et al. |
| 2013/0035745 A1 | 2/2013 | Ahmed et al. |
| 2013/0053620 A1 | 2/2013 | Susedik et al. |
| 2013/0123568 A1 | 5/2013 | Hamilton et al. |
| 2013/0123629 A1 | 5/2013 | Rosenberg et al. |
| 2013/0123764 A1 | 5/2013 | Zarsky et al. |
| 2013/0123765 A1 | 5/2013 | Zarsky et al. |
| 2013/0137918 A1 | 5/2013 | Phillips et al. |
| 2013/0144280 A1 | 6/2013 | Eckhouse et al. |
| 2013/0150653 A1 | 6/2013 | Borsody |
| 2013/0158634 A1 | 6/2013 | Ron Edoute et al. |
| 2013/0178764 A1 | 7/2013 | Eckhouse et al. |
| 2013/0184693 A1 | 7/2013 | Neev |
| 2013/0238043 A1 | 9/2013 | Beardall et al. |
| 2013/0238061 A1 | 9/2013 | Edoute |
| 2013/0261374 A1 | 10/2013 | Elder |
| 2013/0261683 A1 | 10/2013 | Soikum et al. |
| 2013/0267943 A1 | 10/2013 | Hancock |
| 2013/0303904 A1 | 11/2013 | Barthe et al. |
| 2013/0304159 A1 | 11/2013 | Simon et al. |

(56) References Cited

U.S. PATENT DOCUMENTS

| | | |
|---|---|---|
| 2013/0317281 A1 | 11/2013 | Schneider |
| 2013/0331637 A1 | 12/2013 | Greff |
| 2014/0005758 A1 | 1/2014 | Ben-Yehuda et al. |
| 2014/0046423 A1 | 2/2014 | Rajguru |
| 2014/0066786 A1 | 3/2014 | Naghavi et al. |
| 2014/0148870 A1 | 5/2014 | Burnett |
| 2014/0194958 A1 | 7/2014 | Chabal et al. |
| 2014/0200388 A1 | 7/2014 | Schneider et al. |
| 2014/0243933 A1 | 8/2014 | Ginggen |
| 2014/0249609 A1 | 9/2014 | Zarsky et al. |
| 2014/0257071 A1 | 9/2014 | Curran et al. |
| 2014/0276248 A1 | 9/2014 | Hall et al. |
| 2014/0276693 A1 | 9/2014 | Altshuler et al. |
| 2014/0277302 A1 | 9/2014 | Weber et al. |
| 2014/0303425 A1 | 10/2014 | Pilla et al. |
| 2014/0303525 A1 | 10/2014 | Sitharaman |
| 2014/0303696 A1 | 10/2014 | Anderson et al. |
| 2014/0303697 A1 | 10/2014 | Anderson et al. |
| 2014/0316393 A1 | 10/2014 | Levinson |
| 2014/0330067 A1 | 11/2014 | Jordan |
| 2014/0350438 A1 | 11/2014 | Papirov et al. |
| 2014/0364841 A1 | 12/2014 | Kornstein |
| 2014/0371515 A1 | 12/2014 | John |
| 2014/0378875 A1 | 12/2014 | Ron Edoute et al. |
| 2015/0025299 A1 | 1/2015 | Edoute |
| 2015/0080769 A1 | 3/2015 | Lotsch |
| 2015/0088105 A1 | 3/2015 | Fatemi |
| 2015/0112412 A1 | 4/2015 | Anderson et al. |
| 2015/0119849 A1 | 4/2015 | Aronhalt et al. |
| 2015/0123661 A1 | 5/2015 | Yui et al. |
| 2015/0127075 A1 | 5/2015 | Ward et al. |
| 2015/0133717 A1 | 5/2015 | Ghiron et al. |
| 2015/0141877 A1 | 5/2015 | Feldman |
| 2015/0157873 A1 | 6/2015 | Sokolowski |
| 2015/0165226 A1 | 6/2015 | Simon et al. |
| 2015/0165232 A1 | 6/2015 | Altshuler et al. |
| 2015/0165238 A1 | 6/2015 | Slayton et al. |
| 2015/0174002 A1 | 6/2015 | Burbank et al. |
| 2015/0202454 A1 | 7/2015 | Burnett |
| 2015/0216719 A1 | 8/2015 | DeBenedictis et al. |
| 2015/0216720 A1 | 8/2015 | Debenedictis et al. |
| 2015/0216816 A1 | 8/2015 | O'Neil et al. |
| 2015/0223975 A1 | 8/2015 | Anderson et al. |
| 2015/0238248 A1 | 8/2015 | Thompson et al. |
| 2015/0238771 A1 | 8/2015 | Zarsky et al. |
| 2015/0272776 A1 | 10/2015 | Gonzales et al. |
| 2015/0283022 A1 | 10/2015 | Lee et al. |
| 2015/0297909 A1 | 10/2015 | Peashock |
| 2015/0314133 A1 | 11/2015 | Yamashiro |
| 2015/0328077 A1 | 11/2015 | Levinson |
| 2015/0328475 A1 | 11/2015 | Kim et al. |
| 2015/0342661 A1 | 12/2015 | Ron Edoute |
| 2015/0342780 A1 | 12/2015 | Levinson et al. |
| 2015/0360045 A1 | 12/2015 | Fischell et al. |
| 2015/0367141 A1 | 12/2015 | Goetz |
| 2015/0375005 A1 | 12/2015 | Segal |
| 2016/0015995 A1 | 1/2016 | Leung |
| 2016/0016013 A1 | 1/2016 | Capelli et al. |
| 2016/0020070 A1 | 1/2016 | Kim et al. |
| 2016/0022349 A1 | 1/2016 | Woloszko et al. |
| 2016/0030763 A1 | 2/2016 | Midorikawa et al. |
| 2016/0045755 A1 | 2/2016 | Chun et al. |
| 2016/0051401 A1 | 2/2016 | Yee et al. |
| 2016/0051827 A1 | 2/2016 | Ron Edoute et al. |
| 2016/0066977 A1 | 3/2016 | Neal, II et al. |
| 2016/0066994 A1 | 3/2016 | Shanks |
| 2016/0067516 A1 | 3/2016 | Schneider et al. |
| 2016/0067517 A1 | 3/2016 | Burnett |
| 2016/0089550 A1 | 3/2016 | Debenedictis et al. |
| 2016/0106982 A1 | 4/2016 | Cakmak et al. |
| 2016/0121112 A1 | 5/2016 | Azar |
| 2016/0129273 A1 | 5/2016 | Park |
| 2016/0129274 A1 | 5/2016 | Park |
| 2016/0150494 A1 | 5/2016 | Tabet et al. |
| 2016/0151637 A1 | 6/2016 | Abe et al. |
| 2016/0158574 A1 | 6/2016 | Eckhouse et al. |
| 2016/0175193 A1 | 6/2016 | Jung |
| 2016/0184601 A1 | 6/2016 | Gleich et al. |
| 2016/0193466 A1 | 7/2016 | Burnett |
| 2016/0213924 A1 | 7/2016 | Coleman et al. |
| 2016/0220834 A1 | 8/2016 | Schwarz |
| 2016/0250494 A1 | 9/2016 | Sakaki et al. |
| 2016/0256702 A1 | 9/2016 | Schwarz et al. |
| 2016/0256703 A1 | 9/2016 | Schwarz et al. |
| 2016/0270951 A1 | 9/2016 | Martins et al. |
| 2016/0317346 A1 | 11/2016 | Kovach |
| 2016/0317827 A1 | 11/2016 | Schwarz et al. |
| 2016/0324684 A1 | 11/2016 | Levinson et al. |
| 2016/0346561 A1 | 12/2016 | Ron Edoute et al. |
| 2016/0354237 A1 | 12/2016 | Gonzales et al. |
| 2017/0001024 A1 | 1/2017 | Prouza |
| 2017/0001025 A1 | 1/2017 | Schwarz et al. |
| 2017/0001026 A1 | 1/2017 | Schwarz et al. |
| 2017/0001027 A1 | 1/2017 | Ladman et al. |
| 2017/0001028 A1 | 1/2017 | Ladman et al. |
| 2017/0001029 A1 | 1/2017 | Pribula et al. |
| 2017/0001030 A1 | 1/2017 | Pribula et al. |
| 2017/0007309 A1 | 1/2017 | Debenedictis et al. |
| 2017/0043177 A1 | 2/2017 | Ron Edoute et al. |
| 2017/0050019 A1 | 2/2017 | Ron Edoute et al. |
| 2017/0072212 A1 | 3/2017 | Ladman et al. |
| 2017/0087373 A1 | 3/2017 | Schwarz |
| 2017/0100585 A1 | 4/2017 | Hall et al. |
| 2017/0105869 A1 | 4/2017 | Frangineas, Jr. |
| 2017/0106201 A1 | 4/2017 | Schwarz et al. |
| 2017/0143958 A1 | 5/2017 | Shalev et al. |
| 2017/0156907 A1 | 6/2017 | Harris et al. |
| 2017/0173347 A1 | 6/2017 | Schwarz et al. |
| 2017/0182334 A1 | 6/2017 | Altshuler et al. |
| 2017/0182335 A1 | 6/2017 | Altshuler et al. |
| 2017/0189707 A1 | 7/2017 | Zabara |
| 2017/0196731 A1 | 7/2017 | Debenedictis et al. |
| 2017/0209708 A1 | 7/2017 | Schwarz |
| 2017/0239079 A1 | 8/2017 | Root et al. |
| 2017/0239467 A1 | 8/2017 | Shalev et al. |
| 2017/0259077 A1 | 9/2017 | Jin |
| 2017/0280889 A1 | 10/2017 | Koch |
| 2017/0304642 A1 | 10/2017 | Ron Edoute et al. |
| 2017/0319378 A1 | 11/2017 | Anderson et al. |
| 2017/0325992 A1 | 11/2017 | Debenedictis et al. |
| 2017/0325993 A1 | 11/2017 | Jimenez et al. |
| 2017/0326042 A1 | 11/2017 | Zeng et al. |
| 2017/0326346 A1 | 11/2017 | Jimenez et al. |
| 2017/0333705 A1 | 11/2017 | Schwarz |
| 2017/0348143 A1 | 12/2017 | Rosen et al. |
| 2017/0348539 A1 | 12/2017 | Schwarz et al. |
| 2017/0354530 A1 | 12/2017 | Shagdar et al. |
| 2018/0001106 A1 | 1/2018 | Schwarz |
| 2018/0001107 A1 | 1/2018 | Schwarz et al. |
| 2018/0028831 A1 | 2/2018 | Ron Edoute et al. |
| 2018/0103991 A1 | 4/2018 | Linhart et al. |
| 2018/0125416 A1 | 5/2018 | Schwarz et al. |
| 2018/0133498 A1 | 5/2018 | Chornenky et al. |
| 2018/0153736 A1 | 6/2018 | Mills et al. |
| 2018/0153760 A1 | 6/2018 | Rosen et al. |
| 2018/0161197 A1 | 6/2018 | Baker et al. |
| 2018/0185081 A1 | 7/2018 | O'Neil et al. |
| 2018/0185189 A1 | 7/2018 | Weber et al. |
| 2018/0214300 A1 | 8/2018 | Anderson et al. |
| 2018/0228646 A1 | 8/2018 | Gonzales et al. |
| 2018/0229048 A1 | 8/2018 | Sikora et al. |
| 2018/0236254 A1 | 8/2018 | Schwarz et al. |
| 2018/0250056 A1 | 9/2018 | Avram et al. |
| 2018/0263677 A1 | 9/2018 | Hilton et al. |
| 2018/0264245 A1 | 9/2018 | Edwards et al. |
| 2018/0271767 A1 | 9/2018 | Jimenez et al. |
| 2018/0310950 A1 | 11/2018 | Yee et al. |
| 2018/0345012 A1 | 12/2018 | Schwarz et al. |
| 2019/0000524 A1 | 1/2019 | Rosen et al. |
| 2019/0000529 A1 | 1/2019 | Kothare et al. |
| 2019/0000663 A1 | 1/2019 | Anderson et al. |
| 2019/0029876 A1 | 1/2019 | Anderson et al. |
| 2019/0030356 A1 | 1/2019 | Schwarz |
| 2019/0053941 A1 | 2/2019 | Samson |

(56) References Cited

U.S. PATENT DOCUMENTS

| | | |
|---|---|---|
| 2019/0134414 A1 | 5/2019 | Prouza et al. |
| 2019/0151655 A1 | 5/2019 | Hall et al. |
| 2019/0183562 A1 | 6/2019 | Widgerow |
| 2019/0192219 A1 | 6/2019 | Kreindel |
| 2019/0192872 A1 | 6/2019 | Schwarz et al. |
| 2019/0192873 A1 | 6/2019 | Schwarz et al. |
| 2019/0192875 A1 | 6/2019 | Schwarz et al. |
| 2019/0201705 A1 | 7/2019 | Schwarz et al. |
| 2019/0201706 A1 | 7/2019 | Schwarz et al. |
| 2019/0299018 A1 | 10/2019 | Chornenky et al. |
| 2019/0314629 A1 | 10/2019 | Kreindel |
| 2019/0314638 A1 | 10/2019 | Kreindel |
| 2019/0329065 A1 | 10/2019 | Gandel |
| 2019/0336783 A1 | 11/2019 | Sokolowski |
| 2019/0344091 A1 | 11/2019 | Fischer |
| 2019/0350646 A1 | 11/2019 | Kreindel |
| 2019/0365462 A1 | 12/2019 | Casalino et al. |
| 2019/0388698 A1 | 12/2019 | Schwarz et al. |
| 2020/0001103 A1 | 1/2020 | Schwarz et al. |
| 2020/0016422 A1 | 1/2020 | Ron Edoute et al. |
| 2020/0016423 A1 | 1/2020 | Ron Edoute et al. |
| 2020/0054890 A1 | 2/2020 | Schwarz et al. |
| 2020/0061385 A1 | 2/2020 | Schwarz et al. |
| 2020/0061386 A1 | 2/2020 | Schwarz et al. |
| 2020/0129759 A1 | 4/2020 | Schwarz |
| 2020/0139148 A1 | 5/2020 | Schwarz et al. |
| 2020/0155221 A1 | 5/2020 | Marchitto et al. |
| 2020/0206524 A1 | 7/2020 | Katznelson et al. |
| 2020/0237424 A1 | 7/2020 | Hunziker et al. |
| 2020/0281642 A1 | 9/2020 | Kreindel |
| 2020/0289838 A1 | 9/2020 | Schwarz et al. |
| 2020/0324133 A1 | 10/2020 | Schwarz et al. |

FOREIGN PATENT DOCUMENTS

| | | |
|---|---|---|
| AU | 2012244313 B2 | 11/2014 |
| AU | 2014203094 B2 | 7/2015 |
| AU | 2013207657 B2 | 11/2015 |
| BR | PI0812502 A2 | 6/2015 |
| CA | 2484880 A1 | 4/2006 |
| CA | 2604112 C | 7/2016 |
| CA | 3019140 A1 | 10/2017 |
| CA | 3019410 A1 | 10/2017 |
| CA | 3023821 A1 | 11/2017 |
| CH | 714113 A2 | 3/2019 |
| CN | 101234231 A | 8/2008 |
| CN | 201906360 U | 7/2011 |
| CN | 102319141 A | 1/2012 |
| CN | 102711706 A | 10/2012 |
| CN | 102847231 A | 1/2013 |
| CN | 202637725 U | 1/2013 |
| CN | 203169831 U | 9/2013 |
| CN | 102319141 B | 8/2014 |
| CN | 107613914 A | 1/2018 |
| CN | 108882992 A | 11/2018 |
| CN | 109310516 A | 2/2019 |
| DE | 718637 C | 3/1942 |
| DE | 1118902 B | 12/1961 |
| DE | 2748780 A1 | 5/1978 |
| DE | 3205048 A1 | 8/1983 |
| DE | 3610474 A1 | 10/1986 |
| DE | 69318706 T2 | 1/1999 |
| DE | 10062050 A1 | 4/2002 |
| DE | 60033756 T2 | 6/2007 |
| DE | 102009023855 A1 | 12/2010 |
| DE | 102009050010 A1 | 5/2011 |
| DE | 102010004307 A1 | 7/2011 |
| DE | 102011014291 A1 | 9/2012 |
| DE | 102016116399 A1 | 3/2018 |
| DE | 202016008884 U1 | 7/2020 |
| DE | 102010014157 B4 | 2/2021 |
| DK | 0633008 T3 | 3/1999 |
| EA | 000494 B1 | 8/1999 |
| EA | 002087 B1 | 12/2001 |
| EA | 002179 B1 | 2/2002 |
| EA | 003851 B1 | 10/2003 |
| EA | 007347 B1 | 8/2006 |
| EA | 007975 B1 | 2/2007 |
| EP | 0048451 A1 | 3/1982 |
| EP | 0209246 A1 | 1/1987 |
| EP | 0459101 A1 | 12/1991 |
| EP | 0459401 A1 | 12/1991 |
| EP | 0633008 A1 | 1/1995 |
| EP | 0788813 A1 | 8/1997 |
| EP | 0633008 B1 | 5/1998 |
| EP | 0692993 B1 | 9/1999 |
| EP | 1022034 A1 | 7/2000 |
| EP | 1917935 B1 | 1/2011 |
| EP | 2308559 A2 | 4/2011 |
| EP | 2139560 B1 | 5/2012 |
| EP | 2461765 A1 | 6/2012 |
| EP | 2069014 B1 | 6/2013 |
| EP | 2614807 A1 | 7/2013 |
| EP | 2676700 A2 | 12/2013 |
| EP | 2694159 A2 | 2/2014 |
| EP | 2749259 A1 | 7/2014 |
| EP | 2814445 A1 | 12/2014 |
| EP | 2856986 A1 | 4/2015 |
| EP | 3009167 A1 | 4/2016 |
| EP | 2501352 B1 | 7/2016 |
| EP | 3209246 A1 | 8/2017 |
| EP | 3342379 A1 | 7/2018 |
| EP | 3389532 A1 | 10/2018 |
| EP | 3434323 A1 | 1/2019 |
| EP | 3721939 A1 | 10/2020 |
| ES | 2118925 T3 | 10/1998 |
| ES | 2300569 T3 | 6/2008 |
| ES | 2305698 T3 | 11/2008 |
| ES | 2359581 T3 | 5/2011 |
| ES | 2533145 A2 | 4/2015 |
| ES | 2533145 B1 | 7/2016 |
| ES | 2533145 R1 | 10/2018 |
| FR | 3041881 A1 | 4/2017 |
| FR | 3061012 A1 | 6/2018 |
| GB | 260116 A | 10/1926 |
| GB | 390500 A | 4/1933 |
| GB | 871672 A | 6/1961 |
| GB | 2176009 B | 12/1989 |
| GB | 2286660 A | 8/1995 |
| GR | 3027678 T3 | 11/1998 |
| IT | 1217550 B | 3/1990 |
| JP | 2003305131 A | 10/2003 |
| JP | 2006130055 A | 5/2006 |
| JP | 4178762 B2 | 11/2008 |
| JP | 4324673 B2 | 9/2009 |
| JP | 2010207268 A | 9/2010 |
| JP | 2010533054 A | 10/2010 |
| JP | 2011194176 A | 10/2011 |
| JP | 2013063285 A | 4/2013 |
| JP | 2017518857 A | 7/2017 |
| JP | 2018501927 A | 1/2018 |
| JP | 2018018650 A | 2/2018 |
| KR | 20030065126 A | 8/2003 |
| KR | 100484618 B1 | 4/2005 |
| KR | 100491988 B1 | 5/2005 |
| KR | 100556230 B1 | 3/2006 |
| KR | 20090063618 A | 6/2009 |
| KR | 20110123831 A | 11/2011 |
| KR | 20120037011 A | 4/2012 |
| KR | 20130072244 A | 7/2013 |
| KR | 101292289 B1 | 8/2013 |
| KR | 20130128391 A | 11/2013 |
| KR | 101413022 B1 | 7/2014 |
| KR | 101415141 B1 | 7/2014 |
| KR | 101447532 B1 | 10/2014 |
| KR | 101511444 B1 | 4/2015 |
| KR | 20150058102 A | 5/2015 |
| KR | 20150079619 A | 7/2015 |
| KR | 20150106379 A | 9/2015 |
| KR | 101650155 B1 | 8/2016 |
| KR | 101673182 B1 | 11/2016 |
| KR | 20170090654 A | 8/2017 |
| KR | 20170107603 A | 9/2017 |
| KR | 101794269 B1 | 11/2017 |

(56) References Cited

FOREIGN PATENT DOCUMENTS

| | | |
|---|---|---|
| KR | 20180059114 A | 6/2018 |
| KR | 20180092020 A | 8/2018 |
| KR | 101941863 B1 | 1/2019 |
| KR | 20190005981 A | 1/2019 |
| KR | 102000971 B1 | 7/2019 |
| KR | 20190001779 U | 7/2019 |
| KR | 200491572 Y1 | 5/2020 |
| KR | 20200000889 U | 5/2020 |
| KR | 20200052602 A | 5/2020 |
| KR | 20200056692 A | 5/2020 |
| KR | 20200056693 A | 5/2020 |
| KR | 20200056801 A | 5/2020 |
| KR | 20200056802 A | 5/2020 |
| KR | 20200057154 A | 5/2020 |
| KR | 20210002973 A | 1/2021 |
| KR | 20210002974 A | 1/2021 |
| MX | 2012012158 A | 4/2014 |
| NL | 7510644 A | 3/1977 |
| NL | 1037451-02 | 5/2011 |
| RU | 2212909 C2 | 9/2003 |
| RU | 2226115-02 | 3/2004 |
| RU | 2281128 C2 | 8/2006 |
| RU | 2373971 C2 | 11/2009 |
| RU | 2392979 C2 | 6/2010 |
| RU | 2395267 C2 | 7/2010 |
| RU | 2496532 C2 | 10/2013 |
| RU | 2529471 C2 | 9/2014 |
| RU | 2596053 C2 | 8/2016 |
| RU | 2645923 C2 | 2/2018 |
| SI | 24921 A | 8/2016 |
| TW | 200423986 A | 11/2004 |
| WO | WO-9521655 A1 | 8/1995 |
| WO | WO9527533 A1 | 10/1995 |
| WO | WO-9932191 A1 | 7/1999 |
| WO | WO-0013749 A1 | 3/2000 |
| WO | WO-0044346 A1 | 8/2000 |
| WO | WO-0107111 A2 | 2/2001 |
| WO | WO-0112089 A1 | 2/2001 |
| WO | WO-0193797 A2 | 12/2001 |
| WO | 2002025675 A1 | 3/2002 |
| WO | WO-03078596 A2 | 9/2003 |
| WO | WO 03079916 A1 | 10/2003 |
| WO | 2003090863 A1 | 11/2003 |
| WO | WO-03103769 A1 | 12/2003 |
| WO | 2004087255 A1 | 10/2004 |
| WO | WO-2004095385 A2 | 11/2004 |
| WO | WO-2004095835 A1 | 11/2004 |
| WO | WO-2004108211 A1 | 12/2004 |
| WO | WO-2005032660 A1 | 4/2005 |
| WO | WO-2006115120 A1 | 11/2006 |
| WO | WO-2007140584 A1 | 12/2007 |
| WO | WO-2008012827 A2 | 1/2008 |
| WO | WO 2008060494 A2 | 5/2008 |
| WO | 2008109058 A1 | 9/2008 |
| WO | WO-2008127011 A2 | 10/2008 |
| WO | WO-2008145260 A2 | 12/2008 |
| WO | WO-2009011708 A1 | 1/2009 |
| WO | WO-2009013729 A2 | 1/2009 |
| WO | WO-2009042863 A1 | 4/2009 |
| WO | WO-2009044400 A2 | 4/2009 |
| WO | WO-2009083915 A2 | 7/2009 |
| WO | 2010007614 A3 | 1/2010 |
| WO | WO 2010022278 A1 | 2/2010 |
| WO | WO-2010007614 A3 | 5/2010 |
| WO | 2010135425 A1 | 11/2010 |
| WO | WO-2010139376 A1 | 12/2010 |
| WO | WO-2011011749 A1 | 1/2011 |
| WO | WO-2011016019 A1 | 2/2011 |
| WO | WO 2011021184 A1 | 2/2011 |
| WO | WO-2011045002 A1 | 4/2011 |
| WO | WO-2011058565 A2 | 5/2011 |
| WO | WO-2011156495 A2 | 12/2011 |
| WO | WO-2012029065 A2 | 3/2012 |
| WO | WO-2012040243 A1 | 3/2012 |
| WO | WO-2012103632 A1 | 8/2012 |
| WO | WO-2012138169 A2 | 10/2012 |
| WO | WO-2013021380 A1 | 2/2013 |
| WO | WO-2013026393 A1 | 2/2013 |
| WO | WO-2013035088 A1 | 3/2013 |
| WO | WO-2013074576 A2 | 5/2013 |
| WO | WO-2013098815 A1 | 7/2013 |
| WO | WO-2013191699 A1 | 12/2013 |
| WO | WO 2014009875 A2 | 1/2014 |
| WO | WO-2014016820 A2 | 1/2014 |
| WO | WO-2014109653 A1 | 7/2014 |
| WO | WO-2014141229 A1 | 9/2014 |
| WO | WO-2014149021 A2 | 9/2014 |
| WO | WO-2014151431 A2 | 9/2014 |
| WO | WO-2014163020 A1 | 10/2014 |
| WO | WO-2014164926 A1 | 10/2014 |
| WO | 2015012672 A1 | 1/2015 |
| WO | WO-2015052705 A1 | 4/2015 |
| WO | WO2015083305 A1 | 6/2015 |
| WO | WO-2015137733 A1 | 9/2015 |
| WO | WO-2015157725 A1 | 10/2015 |
| WO | WO-2015179571 A1 | 11/2015 |
| WO | WO-2016140871 A1 | 9/2016 |
| WO | WO-2017002065 A1 | 1/2017 |
| WO | WO-2017103923 A1 | 6/2017 |
| WO | WO-2017159959 A1 | 9/2017 |
| WO | WO-2017160097 A2 | 9/2017 |
| WO | WO-2017176621 A1 | 10/2017 |
| WO | WO-2017196548 A1 | 11/2017 |
| WO | WO-2018008023 A1 | 1/2018 |
| WO | WO-2018044825 A1 | 3/2018 |
| WO | WO-2018121998 A2 | 7/2018 |
| WO | WO-2018122535 A1 | 7/2018 |
| WO | WO-2017160097 A3 | 9/2018 |
| WO | WO-2018208992 A1 | 11/2018 |
| WO | WO-2019166965 A1 | 9/2019 |
| WO | WO-2019173866 A1 | 9/2019 |
| WO | WO-2019183622 A1 | 9/2019 |
| WO | WO-2020002801 A1 | 1/2020 |
| WO | WO-2020035852 A2 | 2/2020 |
| WO | WO-2020041502 A1 | 2/2020 |
| WO | WO-2020174444 A1 | 9/2020 |
| WO | WO-2020208590 A1 | 10/2020 |

OTHER PUBLICATIONS

Abulhasan, J.F., et al., "Peripheral Electrical and Magnetic Stimulation to Augment Resistance Training," Journal of Functional Morphology and Kinesiology, 1(3):328-342, (Sep. 2016).

Bachasson, D., et al., "Quadriceps Function Assessment Using an Incremental Test and Magnetic Neurostimulation: a Reliability Study," Journal of Electromyography and Kinesiology, 23(3):649-658, Elsevier, England, (Jun. 2013).

Barker, A.T, "An Introduction to the Basic Principles of Magnetic Nerve Stimulation," Journal of Clinical Neurophysiology, 8(1):26-37, Lippincott Williams & Wilkins, United States, (Jan. 1991).

Behrens, M., et al., "Repetitive Peripheral Magnetic Stimulation (15 Hz RPMS) of the Human Soleus Muscle did not Affect Spinal Excitability," Journal of Sports Science and Medicine, 10(1):39-44, Dept. of Sports Medicine, Medical Faculty of Uludag University, Turkey (Mar. 2011).

Beilin, G., et al., "Electromagnetic Fields Applied to the Reduction of Abdominal Obesity," Journal of Cosmetic & Laser Therapy, 14(1):24-42, Informa Healthcare, England, (Feb. 2012).

Bustamante, V., et al., "Muscle Training With Repetitive Magnetic Stimulation of the Quadriceps in Severe COPD Patients," Respiratory Medicine, 104(2):237-245, Elsevier, England, (Feb. 2010).

Bustamante, V., et al., "Redox Balance Following Magnetic Stimulation Training in the Quadriceps of Patients With Severe COPD," Free Radical Research, 42(11-12):939-948, Informa Healthcare, England, (Nov. 2008).

Caress, J.B., et al., "A Novel Method of Inducing Muscle Cramps Using Repetitive Magnetic Stimulation," Muscle Nerve, 23(1):126-128, John Wiley & Sons, United States, (Jan. 2000).

Course in Physical Therapy, Presentation, Jan. 4, 2013, 156 pages.

CR Technology, SALUS-TALENT, Technical File of Electromagnetic Stimulator, Document No. TF-C05, 2008, 241 pages.

(56) References Cited

OTHER PUBLICATIONS

CR Technology, Technology for Health and Business for Human Being, investor relations, 2008, 21 pages.
Effective PEMF Magnetic Fat Reduction Slimming Body Beauty Salon Machine (PEMF Star), Wolfbeauty 1980, PEMF STAR, China, Retrieved from the Internet: (URL: https://www.ec21.com/product-details/Effective-PEMF-Magnetic-Fat-Reduction--8928746.html), 2019, 5 pages.
Goetz, S.M., et al., "Coil Design for Neuromuscular Magnetic Stimulation Based on a Detailed 3-D Thigh Model," IEEE Transactions on Magnetics, 50(6):10, IEEE, (Jun. 2014).
Gorodnichev, R.M., "Magnetic Stimulation of Muscles as New Method to Enhance Their Strength," Velikie Luki State Academy of Physical Culture and Sport, Velikie Luki, 2016, 5 pages.
Hamnegard, C.H., et al., "Quadriceps Strength Assessed by Magnetic Stimulation of the Femoral Nerve in Normal Subjects," Clinical Physiology and Functional Imaging, 24(5):276-280, Blackwell, England, (Sep. 2004).
Han, T.R., et al., "Magnetic Stimulation of the Quadriceps Femoris Muscle: Comparison of Pain With Electrical Stimulation," American Journal of Physical Medicine & Rehabilitation, 85(7):593-599, Lippincott Williams & Wilkins, United States, (Jul. 2006).
Increasing Physiotherapy Presence in Cosmetology, Spa Inspirations, Jan. 2012, pp. 34-35.
Iskra Medical, Magneto System, 2012, 2 pages.
Katuscakova, Z.L., et al., High Induction Magnet Therapy in Rehabilitation, Department of Physiactric Rehabilitation, 2012, 72 pages.
Lampropoulou, S.I., et al., "Magnetic Versus Electrical Stimulation in the Interpolation Twitch Technique of Elbow Flexors," Journal of Sports Science and Medicine, 11(4):709-718, Dept. of Sports Medicine, Medical Faculty of Uludag University, Turkey (Dec. 2012).
Lin, V.W., et al., "Functional Magnetic Stimulation for Restoring Cough in Patients With Tetraplegia," Archives of Physical Medicine and Rehabilitation, 79(5):517-522, W.B. Saunders, United States, (May 1998).
Lin, V.W., et al., "Functional Magnetic Stimulation of Expiratory Muscles: a Noninvasive and New Method for Restoring Cough," Journal of Applied Physiology (1985), 84(4):1144-1150, American Physiological Society, United States, (Apr. 1998).
Madariaga, V.B., et al., "[Magnetic Stimulation of the Quadriceps: Analysis of 2 Stimulators Used for Diagnostic and Therapeutic Applications]," Archives De Bronconeumologia, 43(7):411-417, Elsevier Espana, Spain, (Jul. 2007).
MagVenture, Magnetic Stimulation, Accessories Catalogue, Accessories Catalogue, 2011, 54 pages.
MagVenture, MagPro® by MagVenture®, Versatility in Magnetic Stimulation, World Leading Transcranial Magnetic Stimulation Systems, 2011, 6 Pages.
Neuro Star, TMS Therapy, Bringing Hope to Patients with Depression, 2013, 6 Pages.
Neurosoft, Ivanovo, Since 1992, Magnetic Stimulator, NEURO-MS, Technical Manual, Neurosoft Ltd, Ivanovo, Russia, 2006, 67 Pages.
Nexstim NBS System, Navigated Brain Stimulation, Noninvasive, direct cortical mapping, 2012, 5 Pages.
Obsluze, N.K.,Usage Instructions, User's Manual, Device for high-induction magnetic stimulation of type designation:SaluterMoti, 2016, 88 Pages.
Operating Manual: Magstim D70$^2$ Coil, MOP06-EN, Revision 01, The Magstim Company Limited, Feb. 2012, 14 Pages.
Operating Manual: Magstim Magstim 200$^2$, MOP01-EN, Revision 01, The Magstim Company Limited, Sep. 2011, 25 Pages.
Operating Manual: Magstim, Magstim Alpha Coil Range, MOP11-EN, Revision 01, Oct. 2012, 18 Pages.
Operating Manual: Magstim, Magstim Bistim$^2$, MOP02-EN, Revision, The Magstim Company Limited, 01, Sep. 2011, 27 Pages.
Operating Manual, MAGSTIM, Model 200, P/N 3001-01, Double 70mm, Remote Coil, P/N 3190-00, The Magstim Company Limited, 2006, 32 pages.
Operating Manual: Magstim R, 2nd, Generation Coil Family, 3100-23-02, Magstim Coils, The Magstim Company Limited, Nov. 2002, 14 Pages.
Operating Manual, Magstim R Air-Cooled Double 70mm Coil System, 1600-23-04, The Magstim Company Limited, 1999, 18 Pages.
Operating Manual: Magstim R, Bistim System, P/N 3234-23-01, The Magstim Company Limited, Nov. 2004, 30 Pages.
Operating Manual: Magstim R, Coils & Accessories, 1623-23-07, Magstim Coils & Accessories, May 2010, 24 Pages.
Operating Manual: Magstim, RAPID2, P/N 3576-23-09, The Magstim Company LTD, Nov. 2009, 61 Pages.
Operator's Manual: BTL Emsculpt, BTL Industries Ltd, United Kingdom, 2018, 35 pages.
Operator's Manual: BTL, HPM-6000U, BTL Industries Ltd, United Kingdom, Dec. 2016, 36 pages.
Papimi, For Scientific Research, Pap Ion Magnetic Inductor, Presentation, Magnetotherapeutic Device, Nov. 2009, 61 Pages.
Podebradsky.K., et al., Clinical study of high-inductive electromagnetic stimulator SALUS talent, 2010, 8 pages.
Polkey M.I., et al., "Functional Magnetic Stimulation of the Abdominal Muscles in Humans," American Journal of Respiratory and Critical Care Medicine, 160(2):513-522, American Thoracic Society, United States (Aug. 1999).
Polkey, M.I., et al., "Quadriceps Strength and Fatigue Assessed by Magnetic Stimulation of the Femoral Nerve in Man," Muscle Nerve, 19(5):549-555, John Wiley & Sons, United States, (May 1996).
Quick Start Manuals, Magstim Super Rapid Plus Quick Start, Aalto TMS Laboratory, Aalto School of Science, 2013, 7 Pages.
Salus Talent-A, Remed, User Guide, High Intensity Electro Magnetic Field Therapy, 2017, 37 pages.
DuoMAG Magnetic Stimulator, Alien Technik User Manuel, Jun. 26, 2012, 48 pages, Version 2.1.
Szecsi, J., et al., "A Comparison of Functional Electrical and Magnetic Stimulation for Propelled Cycling of Paretic Patients," Archives of Physical Medicine and Rehabilitation, 90(4):564-570, W.B. Saunders, United States, (Apr. 2009).
Szecsi, J., et al., "Force-pain Relationship in Functional Magnetic and Electrical Stimulation of Subjects With Paresis and Preserved Sensation," Clinical Neurophysiology, 121(9):1589-1597, Elsevier, Netherlands, (Sep. 2010).
Taylor, J.L., "Magnetic Muscle Stimulation Produces Fatigue Without Effort," Journal of Applied Physiology (1985), 103(3):733-734, American Physiological Society, United States, (Sep. 2007).
Tesla Stym, Iskra Medical, Tone the inner muscle with FMS Functional Magnetic Stimulation, 2013, 4 pages.
User Guide: Mag Venture, Magpro family, MagPro R30, MagPro R30 with MagOption, MagPro X100, MagPro X100 with MagOption, MagPro software v.5.0, US-edition, MagPro family User Guide, 2010, 52 Pages.
User Guide, Salus Talent Pro, REMED, High Intensity Electro magnetic Field Therapy—2 Channel, 2017, Version M-1.0.0, 45 pages.
User Guide, Salus Talent, REMED, High Intensity Electro magnetic Field Therapy, Version. M-1.0.0, 2017, 40 pages.
User's Manual: BTL-6000, Super Inductive System Elite, BBTL Industries Ltd, United Kingdom, Sep. 2016, 36 pages.
User Manual: Electro-magnetic Stimulator, Salus-Talent, Version 1.00, Rehabilitation Medical Company, 2013, 34 Pages.
User Manual: Regenetron PRO, System Information, Regenetron PRO User Manual, Nov. 2014, 7 Pages.
Verges S., et al., "Comparison of Electrical and Magnetic Stimulations to Assess Quadriceps Muscle Function," Journal of Applied Physiology (1985), 106(2):701-710, American Physiological Society, United States, (Feb. 2009).
Wasilewski, M.L., Academy of Aesthetic and Anti-Aging Medicine, Application of magnetic fields with deep stimulation in the fight against local obesity of lower limbs, BTL, 2012, 4 pages.
Polk, "Therapeutic Applications of Low-Frequency Sinusoidal and Pulsed Electric and Magnetic Fields," The Biomedical Engineering Handbook, vol. I, 2000, Second edition, pp. 1625-1636.

(56) References Cited

OTHER PUBLICATIONS

Heisel, Physikalische Medizin. Stuttgart: Georg Thieme Verlag KG, 2005. ISBN 3-13-139881-7. p. 159.
Lin, et al., "Functional Magnetic Stimulation: A New Modality for Enhancing Systemic Fibrinolysis," Arch Phys Med Rehabil vol. 80, May 1999, pp. 545-550.
European Patent Office, International Search Report and Written Opinion for International Application No. PCT/IB2016/053930; dated Dec. 12, 2016; 19 pages.
2018 Cutera University, Clinical Forum, Cutera 20, 26 pages.
Accent Radiofrequency System, Operator's Manual, Alma Lasers, Wellbeing Through Technology, 2008, 82 Pages.
Buenos Aires, Oct. 14, 2014, Venus Concept, Provision No. 7246, 56 pages (With Machine Translation).
Exilis, Operator's Manual, BTL, 2012, 44 Pages.
Letter from Department of Health and Human Services, Public Health Service, Dec. 19, 2014, 7 pages.
Reaction User Manual, Viora, Doc No. MK-004 A, 2008, 53 Pages.
Vanquish Operator's Manual, BTL, 2012, 48 Pages.
Venus Legacy, User Manual International, 2009, Venus Concept, 49 pages.
Avram, M.M and Harry, R.S., "Cryolipolysis for Subcutaneous Fat Layer Reduction, " Lasers in Surgery and Medicine, 41(10):703-708, Wiley-Liss, United States (Dec. 2009).
Burge, S.M and Dawber, R.P., "Hair Follicle Destruction and Regeneration in Guinea Pig Skin After Cutaneous Freeze Injury, " Cryobiology, 27(2):153-163, Elsevier, Netherlands (Apr. 1990).
Chesterton, L.S., et al., "Skin Temperature Response to Cryotherapy, " Archives of Physical Medicine and Rehabilitation, 83(4):543-549, W.B. Saunders, United States (Apr. 2002).
CynoSure, SculpSure TM, The New Shape of Energy-Based body Contouring, 2015, Cynosure INC, 2 pages.
Cynosure, Smooth Shapes XV, Now with Smoothshape petite, Transforming non-invasive Body Shaping, Retrieved from the Internet: (http://www.cynosure.com), 2011, Cynosure Inc, 8 pages.
Dybek, T., et al., "Impact of 10 Sessions of Whole Body Cryostimulation on Aerobic and Anaerobic Capacity and on Selected Blood Count Parameters, " Biology of Sport, 29(1):39-43 (Jan. 2012).
Eliminate Stubborn Fat without Surgery or Downtime and Feel Great From Every Angle, Fear No Mirror®, Consultation Guide, Coolsculpting, 2014, 20 pages.
European Commission, "Neurogenerative Disorders," 10 pages printed Dec. 27, 2016.
Fisher, Robert S. et al., "A practical clinical definition of epilepsy", Epilepsia, 55(4): pp. 475-482 (2014).
Hirvonen, H.E., et al., "Effectiveness of Different Cryotherapies on Pain and Disease Activity in Active Rheumatoid Arthritis. A Randomised Single Blinded Controlled Trial, "Clinical and Experimental Rheumatology, 24(3):295-301, Clinical and Experimental Rheumatology S.A. S, Italy (May-Jun. 2006).
I-Lipo by Chromo genex, i-Lipo Ultra is the Intelligent, Non-Surgical Alternative to Liposuction, 2011, 2 pages.
Izumiya, et al., "Fast/Glycolytic Muscle Fiber Growth Reduces Fat Mass and Improves Metabolic Parameters in Obese Mice," Cell Metab. Feb. 2008: 7(2): 159-172.
Jutte, L.S., et al., "The Relationship Between Intramuscular Temperature, Skin Temperature, and Adipose Thickness During Cryotherapy and Rewarming, " Archives of Physical Medicine and Rehabilitation, 82(6):845-850, W.B. Saunders, United States (Jun. 2001).
Kim, Y.H., et al., "The Effect of Cold Air Application on Intra-Articular and Skin Temperatures in the Knee," Yonsei Medical Journal, 43(5):621-626, Yonsei University, Korea (South) (Oct. 2002).
Korman, P., et al., "Temperature Changes in Rheumatoid Hand Treated With Nitrogen Vapors and Cold Air," Rheumatology International, 32(10):2987-2992, Springer International, Germany (Oct. 2012).
Lineham, Christine et al., Brainwave the Irish Epilepsy Assoication, "The Prevalence of Epilepsy in Ireland" Summary Report, pp. 1-8 (May 2009).

Manstein, D., et al., "Selective Cryolysis: A Novel Method of Non-Invasive Fat Removal, " Lasers in Surgery and Medicine, 40(9):595-604, Wiley-Liss, United States (Nov. 2008).
MecoTec Freezing Technology, Presentation Cryoair Whole Body Cryotherapy Chambers, Germany, Jul. 2017, 52 Pages.
Medline, Body Temperature Norms, 2 pages (Year: 2019).
Nadler, S.F., et al., "The Physiologic Basis and Clinical Applications of Cryotherapy and Thermotherapy for the Pain Practitioner," Pain Physician, 7(3):395-399, American Society of Interventional Pain Physicians, United States (Jul. 2004).
Nassab, R., "The Evidence Behind Noninvasive Body Contouring Devices," Aesthetic Surgery Journal, 35(3):279-293, Oxford University Press, England (Mar. 2015).
National Institute of Neurological Disorders and Stroke, Epilepsy Information Page, www.ninds. iih.gov/disorders/epilepsy/epilepsy.htm, pp. 1-6 (Feb. 1, 2016).
Non Final Office Action dated Jun. 23, 2017, in U.S. Appl. No. 15/473,390, Schwarz, T., et al., filed Mar. 29, 2017.
Otte, J.S., et al., "Subcutaneous Adipose Tissue Thickness Alters Cooling Time During Cryotherapy," Archives of Physical Medicine and Rehabilitation, 83(11):1501-1505, W.B. Saunders, United States (Nov. 2002).
Periso SA, CTU mega Diamagnetic Pump 20: Device for Diamagnetic Therapy, CTU Mega 20 Manual, dated Aug. 28, 2019, 44 pages, Pazzallo Switzerland.
Physiomed, MAG-Expert, Physiomed Manual, Dec. 19, 2012.
Reshaping the Future of Your Practice, Cool sculpting, A Revolution in Aesthetic Fat Reduction, 2011, 10 Pages.
Starbelle, PEMF Shape, Webpage, dated Feb. 10, 2020, 3 pages, available at http://www.starbelle.cn/info/PEMFShape.html.
The Burn Centre Care, Education, 3 pages, printed from internet Nov. 13, 2017.
TSEM Med Swiss SA, Diamagnetic Therapy: A Revolutionary Therapy, CTU Mega 20 Catalogue, dated 2016, 24 pages, Lugano Switzerland.
Ultra Slim Professional, The very best body Contouring, Wardphotonics LLC, 2018, 16 pages.
U.S. Appl. No. 62/331,060, inventor Schwarz, T., filed May 3, 2016 (Not Published).
U.S. Appl. No. 62/331,072, inventor Schwarz, T., filed May 3, 2016 (Not Published).
U.S. Appl. No. 62/331,088, inventor Schwarz, T., filed May 3, 2016 (Not Published).
U.S. Appl. No. 62/333,666, inventor Schwarz, T., filed May 9, 2016 (Not Published).
U.S. Appl. No. 62/357,679, inventor Schwarz, T., filed Jul. 1, 2016 (Not Published).
U.S. Appl. No. 62/440,905, inventors Schwarz, T. et al., filed Dec. 30, 2016 (Not Published).
U.S. Appl. No. 62/440,912, inventors Schwarz, T. et al., filed Dec. 30, 2016 (Not Published).
U.S. Appl. No. 62/440,922, inventor Schwarz, T., filed Dec. 30, 2016 (Not Published).
U.S. Appl. No. 62/440,936, inventor Schwarz, T., filed Dec. 30, 2016 (Not Published).
U.S. Appl. No. 62/440,940, inventor Schwarz, T., filed Dec. 30, 2016 (Not Published).
U.S. Appl. No. 62/441,805, inventor Prouza, O., filed Jan. 3, 2017 (Not Published).
U.S. Appl. No. 62/786,731, inventor Schwarz, T., filed Dec. 31, 2018 (Not Published).
U.S. Appl. No. 62/351,156, inventor Schwarz, T., filed Jun. 16, 2016 (Not Published).
Web Md, what is normal body temperature? 3 pages, printed Mar. 4, 2019.
Weight to volume aluminum, 2 pages, printed from internet Sep. 25, 2018.
Weight to volume copper, 2 pages printed from internet Sep. 25, 2018.
Zelickson, B., et al., "Cryolipolysis for Noninvasive Fat Cell Destruction: Initial Results From a Pig Model," Dermatologic Surgery, 35(10):1462-1470, Hagerstown, MD Lippincott, Williams & Wilkins, United States (Oct. 2009).

(56) References Cited

OTHER PUBLICATIONS

ZELTIQ System User Manual—Print and Binding Specifications, ZELTIQ Aesthetics, Inc, Mar. 2011, 88 pages.
Zerona R-Z6 by Erchonia, Specifications,Retrieved from the Internet: (http://www.myzerona.com), 2015, 1 page.
Moon, Chi-Woong "Study on the Pulsed Electromagnetic Fields Effect of Adipocyte Decomposition" Final Report of a Middle-grade Researcher Support Project, Inje University, 2017.
Cutera, truSculptflex, Brochure, dated 2019, 2 pages.
Depatment of Health and Human Services, 501 (k) Letter and Summary for K092476 Body Control System 4M Powered Muscle Stimulator, dated May 7, 2010, 5 pages.
Depatment of Health and Human Services, 501 (k) Letter and Summary for K160992 HPM-6000 Powered Muscle Stimulator, dated Oct. 21, 2016, 9 pages.
Depatment of Health and Human Services, 501 (k) Letter and Summary for K163415 SlimShape System Powered Muscle Stimulator, dated Apr. 20, 2017, 8 pages.
Depatment of Health and Human Services, 501 (k) Letter and Summary for K182106 BTL 799-2T Powered Muscle Stimulator, dated Oct. 23, 2018, 9 pages.
Depatment of Health and Human Services, 501 (k) Letter and Summary for K190456 BTL 799-2L Powered Muscle Stimulator, dated Jul. 5, 2019, 9 pages.
Depatment of Health and Human Services, 501 (k) Letter and Summary for K192224 BTL 899 Powered Muscle Stimulator, dated Dec. 5, 2019, 11 pages.
Kocbach et al., "A Simulation Approach to Optimizing Performance of Equipment for Thermostimulation of Muscle Tissue using COMSOL Multiphysics" Article in Biophysics & Bioeng. dated 2011, 26 pages.
Mekawy et al., "Influence of Electro-lipolysis on Lipid Profile and Central Obesity in Obese Premenopausal Women" Bull. Fac. Ph. Th. Cairo Univ., vol. 17, No. (1), dated Jan. 2012, pp. 59-68.
Pollogen, Maximus Non-invasive body shaping System, User Manual, dated May 1, 2012, 44 pages.
Pollogen, TriFractional FAQs, User Manual, dated Aug. 2011, 4 pages.
Pollogen, TriLipo MED Procedure, Brochure, dated Apr. 7, 2021, 76 pages.
Publication of Medical Device Manufacturing Approval of Salus-TALENT-Pro, approval date Mar. 11, 2014, 39 pages.
Venus Concept Ltd., VenusFreeze MP2, User Manual, dated Jun. 2012, 46 pages.
Venus Concept Ltd., VenusViva, User Manual, dated Aug. 2013, 51 pages.
Wanitphakdeedecha et al., "Treatment of abdominal cellulite and circumference reduction with radiofrequency and dynamic muscle activation" Article in Journal of Cosmetic and Laser Therapy, dated Apr. 6, 2015, 7 pages.
*Allergan, Inc. et al v. BTL Healthcare Technologies A. S.*, PTAB-PGR2021-00015, Paper 16 (Decision Denying Institution of Post-Grant Review), Jun. 17, 2021, 20 pages.
*Allergan, Inc. et al v. BTL Healthcare Technologies A. S.*, PTAB-PGR2021-00016, Paper 16 (Decision Denying Institution of Post-Grant Review), Jun. 17, 2021, 20 pages.
*Allergan, Inc. et al v. BTL Healthcare Technologies A. S.*, PTAB-PGR2021-00017, Paper 16 (Decision Denying Institution of Post-Grant Review), Jun. 16, 2021, 33 pages.
*Allergan, Inc. et al v. BTL Healthcare Technologies A. S.*, PTAB-PGR2021-00018, Paper 16 (Decision Denying Institution of Post-Grant Review), Jun. 16, 2021, 42 pages.
*Allergan, Inc. et al v. BTL Healthcare Technologies A. S.*, PTAB-PGR2021-00020, Paper 16 (Decision Denying Institution of Post-Grant Review), Jun. 16, 2021, 35 pages.
*Allergan, Inc. et al v. BTL Healthcare Technologies A. S.*, PTAB-PGR2021-00021, Paper 17 (Decision Denying Institution of Post-Grant Review), Jun. 16, 2021, 33 pages.
*Allergan, Inc. et al v. BTL Healthcare Technologies A. S.*, PTAB-PGR2021-00022; PTAB-PGR2021-00023; PTAB-PGR2021-00024; PTAB-PGR2021-00025; PTAB-IPR2021-00296; PTAB-IPR2021-00312, Paper 11 (Decision Settlement Prior to Institution of Trial), Jul. 6, 2021, 4 pages.
*BTL Industries, Inc. v. Allergan USA, Inc et al.*, DDE-1-19-cv-02356, Order Administratively Closing Case, Jul. 26, 2021, 1 page.
*BTL Industries, Inc. v. Allergan Ltd. et al.*, DDE-1-20-cv-01046, Order Adminstratively Closing Case, Jul. 26, 2021, 1 page.
*Certain Non-Invasive Aesthetic Body-Contouring Devices, Components Thereof and Methods of Using the Same*, Inv. No. 337-TA-1219, Order No. 30 (Order Concerning the Procedural Schedule), Aug. 4, 2021, 3 pages.
Doucet, B., et al., "Neuromuscular Electrical Stimulation for Skeletal Muscle Function," Yale Journal of Biology & Medicine 85:201-215 (2012).
Gorgey, A., et al., "Effects of Electrical Stimulation Parameters on Fatigue in Skeletal Muscle," J. Orthop. & Sports Phys. Therapy vol. 39(9):684-92 (Sep. 2009).
Iskra Medical, "TESLA Stym Website," URL: <https://web.archive.org/web/20131106123126/http:/www.iskramedical.eu:80/magneto-therapy-medical/tesla-stym (Nov. 6, 2013).
*Lumenis Ltd. v. BTL Healthcare Technologies A.S.*, PTAB-IPR2021-01275, U.S. Pat. No. 10,632,321, Petition for Inter Partes Review, Aug. 5, 2021, 92 pages.
*Lumenis Ltd. v. BTL Healthcare Technologies A.S.*, PTAB-IPR2021-01275, Declaration of Dr. Marom Bikson (EX1002), Aug. 5, 2021, 282 pages.
*Lumenis Ltd. v. BTL Healthcare Technologies A.S.*, PTAB-IPR2021-01276, U.S. Pat. No. 10,965,575, Petition for Inter Partes Review, Aug. 5, 2021, 79 pages.
*Lumenis Ltd. v. BTL Healthcare Technologies A.S.*, PTAB-IPR2021-01276, Declaration of Dr. Marom Bikson (EX1002), Aug. 5, 2021, 241 pages.
*Lumenis Ltd. v. BTL Healthcare Technologies A.S.*, PTAB-IPR2021-01279, U.S. Pat. No. 10,709,895, Petition for Inter Partes Review, Aug. 5, 2021, 88 pages.
*Lumenis Ltd. v. BTL Healthcare Technologies A.S.*, PTAB-IPR2021-01279, Declaration of Dr. Marom Bikson (EX1002), Aug. 5, 2021, 258 pages.
*Lumenis Ltd. v. BTL Healthcare Technologies A.S.*, PTAB-IPR2021-01282, U.S. Pat. No. 10,632,321, Petition for Inter Partes Review, Aug. 5, 2021, 89 pages.
*Lumenis Ltd. v. BTL Healthcare Technologies A.S.*, PTAB-IPR2021-01282, Declaration of Dr. Marom Bikson (EX1002), Aug. 5, 2021, 267 pages.
*Lumenis Ltd. v. BTL Healthcare Technologies A.S.*, PTAB-IPR2021-01283, U.S. Pat. No. 10,695,575, Petition for Inter Partes Review, Aug. 5, 2021, 84 pages.
*Lumenis Ltd. v. BTL Healthcare Technologies A.S.*, PTAB-IPR2021-01283, Declaration of Dr. Marom Bikson (EX1002), Aug. 5, 2021, 241 pages.
*Lumenis Ltd. v. BTL Healthcare Technologies A.S.*, PTAB-IPR2021-01284, U.S. Pat. No. 10,709,895, Petition for Inter Partes Review, Aug. 5, 2021, 93 pages.
*Lumenis Ltd. v. BTL Healthcare Technologies A.S.*, PTAB-IPR2021-01284, Declaration of Dr. Marom Bikson (EX1002), Aug. 5, 2021, 279 pages.
Stevens, J., et al., "Neuromuscular Electrical Stimulation for Quadriceps Muscle Strengthening After Bilateral Total Knee Arthroplasty: A Case Serie," Journal of Orthopaedic & Sports Physical Therapy, 34(1):21-29 (Jan. 2004).
U.S. Appl. No. 60/848,720, inventor Burnett, D., filed Sep. 30, 2006 (Not Published).
Woehrle, J., et al., "Dry Needling and its Use in Health Care—A Treatment Modality and Adjunct for Pain Management," J. Pain & Relief, 4(5):1-3 (Aug. 2015).
501 (k) K030708 Slendertone FLEX Letter from Department of Health and Humane Serivces, Public Health Service, Jun. 25, 2003, 6 pages.
501 (k) K163165 AM-100 Letter from Department of Health and Human Services, Public Health Service, Feb. 16, 2017, 9 pages.
Alma Lasers., "Accent Radiofrequency System, Operator's Manual," Wellbeing Through Technology, 2008, Chapters 1-6, Appendix A.

(56) References Cited

OTHER PUBLICATIONS

Arjunan, P.A., et al., "Computation and Evaluation of Features of Surface Electromyogram to Identify the Force of Muscle Contraction and Muscle Fatigue," BioMed research international 2014:197960, Hindawi Pub. Co, United States (2014).
Barker, A.T., et al., "Non-Invasive Magnetic Stimulation of Human Motor Cortex," Lancet 1(8437):1106-1107, Elsevier, England (May 1985).
Barker, A.T., "The History and Basic Principles of Magnetic Nerve Stimulation," Electroencephalography and Clinical Neurophysiology 51:3-21, Elsevier, Netherlands (1999).
Barrett, J., et al., "Mechanisms of Action Underlying the Effect of Repetitive Transcranial Magnetic Stimulation on Mood: Behavioral and Brain Imaging Studies," Neuropsychopharmacology 29(6):1172-1189, Nature Publishing Group, England (Jun. 1905).
Belanger, A-Y., "Chapter 13: Neuromuscular Electrical Stimulation," in Therapeutic Electrophysical Agents: Evidence Behind Practice, 3rd Edition, Lupash, E., ed., pp. 220-255, Lippincott Williams & Wilkins, United States (2015).
Benton, et al., "Functional Electrical Stimulation—A Practical Clinical Guide," Second Edition, The Professional Staff Association of the Rancho Los Amigos Hospital, Inc. :16 (1981).
Benton, L.A., et al., "Chapter 2: Physiological Basis of Nerve and Muscle Excitation" and "Chapter 4: General Uses of Electrical Stimulation," in Functional Electrical Stimulation: A Practical Guide, 2nd Edition, pp. 11-30 and 53-71, Rancho Los Amigos Rehabilitation Engineering Center, Downey, CA (1981), 42 pages.
Bergh, U., and Ekblom, B., "Influence of Muscle Temperature on Maximal Muscle Strength and Power Output in Human Skeletal Muscles," Acta Physiologica Scandinavica 107(1):33-37, Blackwell Scientific Publications, England (Aug. 1979).
Binder-Macleod, S.A., et al., "Force Output of Cat Motor Units Stimulated with Trains of Linearly Varying Frequency," Journal of Neurophysiology 61(1):208-217, American Physiological Society, United States (Jan. 1989).
Binder-Macleod, S.A., et al., "Use of a Catchlike Property of Human Skeletal Muscle to Reduce Fatigue," Muscle & Nerve 14(9):850-857, John Wiley & Sons, United States (Sep. 1991).
Bio Medical Research Limited., "Slendertone Flex Abdominal Training System, Instructions for Use," All pages (Aug. 2006).
Bio Medical Research Limited., "Slendertone Flex Max Instruction Manual," All pages (Apr. 2006).
Bio-Medical Research Ltd., K010335, 510(k) Summary, Slendertone Flex, All pages (Sep. 2001).
Bio-Medical Research Ltd., K022855 510(k) Summary, Slendertone, 1-6 (Mar. 2003).
Bischoff, C., et al., "Repetitive Magnetic Nerve Stimulation: Technical Considerations and Clinical Use in the Assessment of Neuromuscular Transmission," Electroencephalography and Clinical Neurophysiology 93(1):15-20, Elsevier, Ireland (Feb. 1994).
Bourland, J.D., et al., "Transchest Magnetic (Eddy-Current) Stimulation of the Dog Heart," Medical & Biological Engineering & Computing 28(2):196-198, Springer, United States (Mar. 1990).
BTL Industries, Inc., K163165 510(k) Summary, AM-100, All pages (Feb. 2017).
BTL Industries, Inc., K180813 510(k) Summary, Emsculpt, All pages (Mar. 2018).
*BTL Industries, Inc.* v. *Allergan Ltd et al* DDE-1-20-cv-01046, Complaint for Patent Infringement and Exhibits 1-38, 821 pages (Aug. 2020).
*BTL Industries, Inc.* v. *Allergan Ltd et al* DDE-1-20-cv-01046, Order Granting Motion to Stay Pending Resolution of Proceedings at the International Trade Commission (Unopposed), 2 pages (Oct. 2020).
Busso, M. and Denkova, R., "Efficacy of High Intensity Focused Electro-Magnetic (HIFEM) Field Therapy When Used For Non-Invasive Buttocks Augmentation and Lifting: A Clinical Study" American Society for Laser Medicine and Surgery Abstracts, 382 (2018).
Callaghan, M.J., et al., "Electric Muscle Stimulation of the Quadriceps in the Treatment of Patellofemoral Pain," Archives of Physical Medicine and Rehabilitation 85(6):956-962, W.B. Saunders, United Staes (Jun. 2004).
Carbonaro, M., et al., "Architectural Changes in Superficial and Deep Compartments of the Tibialis Anterior during Electrical Stimulation over Different Sites," IEEE transactions on Neural Systems and Rehabilitation Engineering 28(11):2557-2565, IEEE, United States (Nov. 2020).
Certain Non-Invasive Aesthetic Body Contouring Devices, Components Thereof, and Methods of Using the Same, Inv. No. 337-TA-1219, BTL's Statement of Suggested Claim Terms to Be Construed Pursuant to Ground Rule 6b, Nov. 4, 2020, 2 pages.
Certain Non-Invasive Aesthetic Body Contouring Devices, Components Thereof, and Methods of Using the Same, Inv. No. 337-TA-1219, Complainant BTL's Proposed Construction of Disputed Claim Terms, Dec. 8, 2020, 19 pages.
Certain Non-Invasive Aesthetic Body Contouring Devices, Components Thereof, and Methods of Using the Same, Inv. No. 337-TA-1219, Complaint, Aug. 5, 2020, 93 pages.
Certain Non-Invasive Aesthetic Body Contouring Devices, Components Thereof, and Methods of Using the Same, Inv. No. 337-TA-1219, Joint Claim Construction Chart, Dec. 14, 2020, 15 pages.
Certain Non-Invasive Aesthetic Body Contouring Devices, Components Thereof, and Methods of Using the Same; Inv. No. 337-TA-1219, Joint Claim Construction Chart, Dec. 18, 2020, 15 pages.
Certain Non-Invasive Aesthetic Body Contouring Devices, Components Thereof, and Methods of Using the Same, Inv. No. 337-TA-1219, Respondents' Allergan Limited, Allergan USA, Inc., Allergan, Inc., Zeltiq Aesthetics, Inc., Zeltiq Ireland Unlimited Company, and Zimmer MedizinSysteme GmbH's Notice of Prior Art, Nov. 20, 2020, 53 pages.
Certain Non-Invasive Aesthetic Body Contouring Devices, Components Thereof, and Methods of Using the Same, Inv. No. 337-TA-1219, Respondents' List of Claim Terms for Construction, Nov. 4, 2020, 8 pages.
Certain Non-Invasive Aesthetic Body Contouring Devices, Components Thereof, and Methods of Using the Same; Inv. No. 337-TA-1219, Respondents' List of Proposed Claim Constructions and Their Intrinsic and Extrinsic Support, filed Dec. 15, 2020, 23 pages.
Certain Non-Invasive Aesthetic Body Contouring Devices, Components Thereof, and Methods of Using the Same, Inv. No. 337-TA-1219, Response of Respondent Zimmer MedizinSysteme GmbH to the Complaint and Notice of Investigation, Oct. 22, 2020, 68 pages.
Certain Non-Invasive Aesthetic Body Contouring Devices, Components Thereof, and Methods of Using the Same, Inv. No. 337-TA-1219, Response of Respondents Allergan Limited, Allergan USA, Inc., Allergan, Inc., Zeltiq Aesthetics, Inc., and Zeltiq IrelandUnlimited Company to the Complaint and Notice of Investigation, Oct. 22, 2020, 69 pages.
Certain Non-Invasive Aesthetic Body-Contouring Devices, Components Thereof, and Methods of Using Same, Notice of Institution of Investigation, Inv. No. 337-TA-1219, Notice of Institution of Investigation, Sep. 2, 2020, 21 pages.
Certain Non-Invasive Aesthetic Body-Contouring Devices, Components Thereof, and Methods of Using the Same, Inv. No. 337-TA-1219, Order No. 21 (Initial Determination), Apr. 28, 2021, 5 pages.
Certain Non-Invasive Aesthetic Body-Contouring Devices, Components Thereof, and Methods of Using the Same, Inv. No. 337-TA-1219, Order No. 17: Amending Procedural Schedule, Apr. 9, 2021, 4 pages.
Certified English Translation of Belyaev, A.G., "Effect of Magnetic Stimulation on the Strength Capacity of Skeletal Muscles," Ph.D. Thesis ABSTRACT, Smolensk State Academy of Physical Culture, Sport, and Tourism, Dec. 11, 2020, 23 pages.
Certified English Translation of Belyaev, A.G., "Effect of Magnetic Stimulation on the Strength Capacity of Skeletal Muscles," Ph.D. Thesis, Smolensk State Academy of Physical Culture, Sport, and Tourism, Dec. 11, 2020, 117 pages.

(56) References Cited

OTHER PUBLICATIONS

Chattanooga Group of Encore Medical, L.P., "Intelect SWD 100 User Manual, Operation & Installation Instructions for Intelect SWD 00- Model 1600," All pages (2009).
Collins, D.F., et al., "Large Involuntary Forces Consistent With Plateau-Like Behavior of Human Motoneurons," Journal of Neuroscience 21(11):4059-4065, Society for Neuroscience, United States (Jun. 2001).
Colson, S., et al., "Re-Examination of Training Effects by Electrostimulation in the Human Elbow Musculoskeletal System," International Journal of Sports Medicine 21(4):281-288, Stuttgart, Thieme (May 2000).
CR Technologies, "Salus Talent Pop Manual KFDA First Approval Document" (English Translation), Nov. 25, 2011, 47 pages.
CR Technologies, "Notification of medical device manufacturing item permission, Salus Talent Pop KFDA Approval Document" (English Translation), 3 pages (Sep. 2011).
CR Technology Co, Ltd., "Salus-Talent DOUBLE Sales Brochure" 2 pages, (Oct. 2020).
CR Technology Co. Ltd., "Medical Laser Irradiator Salus-Talent-Pop User Manual Version 1.00" (Nov. 2020).
CR Technology Co. Ltd., Salus Talent Pop User Manual, Ver. 1.00, All pages, Approx. 2012.
Currier, D. P., "Effects of Electrical and Electromagnetic Stimulation after Anterior Cruciate Ligament Reconstruction," The Journal of Orthopaedic and Sports Physical Therapy 17(4):177-84, Williams and Wilkins, United States (1993).
Davies, C.T., et al., "Contractile Properties of the Human Triceps Surae With Some Observations on the Effects of Temperature and Exercise," European Journal of Applied Physiology and Occupational Physiology 49(2):255-269, Springer Verlag, Germany (Aug. 1982).
Deng, Z.D., et al., "Electric Field Depth-Focality Tradeoff in Transcranial Magnetic Stimulation: Simulation Comparison of 50 Coil Designs," Brain stimulation 6(1):1-13, Elsevier, New York (Jan. 2013).
Dudley, G. and Stevenson, S., "Use of Electrical Stimulation in Strength and Power Training," Special Problems in Strength and Power Training :426-435 (2003).
Duncan, D., et al., "Noninvasive Induction of Muscle Fiber Hypertrophy and Hyperplasia: Effects of High-Intensity Focused Electromagnetic Field Evaluated in an In-Vivo Porcine Model: A Pilot Study," Aesthetic Surgery Journal 40(5):568-574, Oxford University Press, United States (Apr. 2020).
Dynatronics., "Better Rehab Solutions for Better Outcomes," Rehabilitation Products Guide 2.3, 2017, 52 pages.
Energist Ltd—Acquired Chromogenez—Old Account, iLipo—Laser Liposuction (i-Lipo), Video Screenshots, Aug. 10, 2009, 5 pages.
Enoka, R.M., "Muscle Strength and Its Development," Sports Medicine 6:146-168, Springer (Oct. 1988).
Epstein, C., et al., "The Oxford Handbook of Transcranial Stimulation," 773 pages (2008).
Faghri, P.D., et al., "The Effects of Functional Electrical Stimulation on Shoulder Subluxation, Arm Function Recovery, and Shoulder Pain in Hemiplegic Stroke Patients," Archives of Physical Medicine and Rehabilitation 75(1):73-79, W.B. Saunders, United States (Jan. 1994).
Fischer, J., et al., "Precise Subpixel Position Measurement with Linear Interpolation of CMOS Sensor Image Data," The 6th IEEE International Conference on Intelligent Data Acquisition and Advanced Computing Systems, 500-504 (Sep. 2011).
Fujimura, K., et al., "Effects of Repetitive Peripheral Magnetic Stimulation on Shoulder Subluxations Caused by Stroke: A Preliminary Study," Neuromodulation : Journal of the International Neuromodulation Society 23(6):847-851, Wiley-Blackwell, United States (Nov. 2020).
Gaines, M., "Slendertone Abdominal Training System, the First FDA-Cleared Abdominal Belt, Introduced in United States by Compex Technologies on Time for Holiday Gift-Giving," Business Wire 44199 (Oct. 2003).
Geddes, L. A., "History of Magnetic Stimulation of the Nervous System," Journal of Clinical Neurophysiology 8(1):3-9, Lippincott Williams & Wilkins, New York, (Jan. 1991).
Geddes, L.A., "History of Magnetic Stimulation of the Nervous System," Journal of Clinical Neurophysiology 8(1):3-9, Lippincott Williams & Wilkins, United States (Jan. 1991).
Goodman, B.E., "Channels Active in the Excitability of Nerves and Skeletal Muscles Across the Neuromuscular Junction: Basic Function and Pathophysiology," Advances in Physiology Education 32(2):127-135, American Physiological Society, United States (Jun. 2008).
Gorodnichev, R.M., et al., "The Effect of Electromagnetic Stimulation on the Parameters of Muscular Strength," Human Physiology 40:65-69 (2014).
Halaas, Y. and Bernardy, J., "Biochemical Perspective of Fat Physiology after Application of HIFEM Field Technology: Additional Investigation of Fat Disruption Effects in a Porcine Study," American Society for Laser Medicine and Surgery Abstracts, S4 (2019).
Han, B.H., et al., "Development of four-channel magnetic nerve stimulator," 2001 Proceedings of the 23rd Annual EMBS International Conference, pp. 1325-1327, Turkey (2001).
Harkey, M.S., "Disinhibitory Interventions and Voluntary Quadriceps Activation: A Systematic Review," Journal of Athletic Training 49(3):411-421, National Athletic Trainers' Association, United States (2014).
Heidland, A., et al., "Neuromuscular Electrostimulation Techniques: Historical Aspects and Current Possibilities in Treatment of Pain and Muscle Waisting," Clinical Nephrology 79 Suppl 1:S12-S23, Dustri-Verlag Dr. Karl Feistle, Germany (Jan. 2012).
Hill, A., "The Influence of Temperature on the Tension Developed in an Isometric Twitch," Proceeding of the Royal Society B 138:349-354, (Sep. 1951).
Hovey, C. and Jalinous, R., "The Guide to Magnetic Stimulation" Magstim, Pioneers in Nerve Stimulation and Monitoring, pp. 1-44 (2016).
Hovey, C., et al., "The Guide to Magnetic Stimulation," The Magstim Company Limited, 48 pages (Jul. 2006).
Huang, Y.Z., et al., "Theta Burst Stimulation of the Human Motor Cortex," Neuron 45(2):201-206, Cell Press, United States (Jan. 2005).
Irazoqui P., Post Grant Review of U.S. Pat. No. 10,695,576, PTAB-PGR2021-00024, filed as EX1085, Dec. 14, 2020, 25 pages.
Iskra Medical, "TESLA Stym—Functional Magnetic Stimulation FMS," Nov. 2013, http://ww.iskramedical.eu/magneto-therapy-medical/tesla-stym, 5 pages.
Jacob, C., et al., "High Intensity Focused Electro-Magnetic Technology (HIFEM) for Non-Invasive Buttock Lifting and Toning of Gluteal Muscles: A Multi-Center Efficacy and Safety Study," Journal of Drugs in Dermatology 17(11):1229-1232, Physicians Continuing Education Corporation, United States (Nov. 2018).
Jacob, C.I., et al., "Safety And Efficacy of a Novel High-Intensity Focused Electromagnetic Technology Device for Noninvasive Abdominal Body Shaping," Journal of Cosmetic Dermatology, 17(5):783-787, Blackwell Science, United States (Oct. 2018).
Jacobm C., and Paskova, "A Novel Non-lnvasive Technology Based on Simultaneous Induction of Changes in Adipose and Muscle Tissues: Safety and Efficacy of a High Intensity Focused Electro-Magnetic (HIFEM) Field Device Used for Abdominal Body Shaping," American Society for Laser Medicine and Surgery, 2018 Electronic Posters (ePosters) Town Hall and ePosters, 369, p. 1, Wiley Periodicals, Inc. (2018).
Johari Digital Healthcare Ltd., 510(k)—K062439 Powertone Letter from Department of Health and Humane Services Summary, Public Health Service, Jan. 8, 2007, 6 pages.
Johari Digital Healthcare Ltd., "510(k)—K131291 TORC BODY Letter from Department of Health and Humane Services", Public Health Service, Jun. 14, 2013, 10 pages.

(56) References Cited

OTHER PUBLICATIONS

Johari Digital Healthcare Ltd., K131291 510(k) Summary, TorcBody, All pages (Jun. 2013).

Katz, B., et al., "Changes in Subcutaneous Abdominal Fat Thickness Following High-Intensity Focused Electro-Magnetic (HIFEM) Field Treatments: A Multi Center Ultrasound Study," American Society for Laser Medicine and Surgery Abstracts, 360-361 (2018).

Katz, B., et al., "Ultrasound Assessment of Subcutaneous Abdominal Fat Thickness after Treatments with a High-Intensity Focused Electromagnetic Field Device: A Multicenter Study," Dermatologic Surgery 45(12):1542-1548, Williams & Wilkins, United States (Dec. 2019).

Kavanagh, S., et al., "Use of a Neuromuscular Electrical Stimulation Device for Facial Muscle Toning: A Randomized, Controlled Trial," Journal of Cosmetic Dermatology 11(4):261-266, Blackwell Science, United States (Dec. 2012).

Kent, D., and Jacob C., "Computed Tomography (CT) Based Evidence of Simultaneous Changes in Human Adipose and Muscle Tissues Following a High Intensity Focused Electro-Magnetic Field (HIFEM) Application: A New Method for Non-Invasive Body Sculpting," American Society for Laser Medicine and Surgery Abstracts, p. 370 (2018).

Kent, D,E. and Jacob, C.I., Simultaneous Changes in Abdominal Adipose and Muscle Tissues Following Treatments by High-Intensity Focused Electromagnetic HIFEM Technology-Based Device: Computed Tomography Evaluation, Journal of Drugs in Dermatology 18(11):1098-1102, Physicians Continuing Education Corporation, United States (Nov. 2019).

Kinney, B.M. and Lozanova P., "High Intensity Focused Electromagnetic Therapy Evaluated by Magnetic Resonance Imaging: Safety and Efficacy Study of a Dual Tissue Effect Based Non-Invasive Abdominal Body Shaping," Lasers in Surgery and Medicine 51 (1):40-46, Wiley-Liss, United States (Jan. 2019).

Kolin, A., et al., "Stimulation of Irritable Tissues by means of an Alternating Magnetic Field," Proceedings of the Society for Experimental Biology and Medicine 102:251-253, Blackwell Science, United States (Oct. 1959).

Kumar, N. and Agnihotri, R.C., "Effect of Frequency and Amplitude of Fes Pulses on Muscle Fatigue During Toning of Muscles," Journal of Scientific and Industrial Research 67(4):288-290, (Apr. 2008).

Langford, J. and Mccarthy, P.W., "Randomised controlled clinical trial of magnet use in chronic low back pain; a pilot study," Clinical Chiropractic 8(1):13-19, Elsevier (Mar. 2005).

Lee, P.B., et al., "Efficacy of Pulsed Electromagnetic Therapy for Chronic Lower Back Pain: a Randomized, Double-blind, Placebcontrolled Study," The Journal of International Medical Research 34(2):160-167, Cambridge Medical Publications, England (Mar.-Apr. 2006).

Leitch, M., et al., "Intramuscular Stimulation of Tibialis Anterior in Human Subjects: The Effects of Discharge Variability on Force Production and Fatigue," Physiological Reports 5(15):e13326, Wiley Periodicals, Inc., United States (Aug. 2017).

Leon-Salas, W.D., et al., "A Dual Mode Pulsed Electro-Magnetic Cell Stimulator Produces Acceleration of Myogenic Differentiation," Recent Patents on Biotechnology 7(1):71-81, Bentham Science Publishers, United Arab Emirates (Apr. 2013).

Lin, V.W., et al., "Functional Magnetic Stimulation for Conditioning of Expiratory Muscles in Patients with Spinal Cord Injury.," Archives of Physical medicine and Rehabilitation 82(2):162-166, W.B. Saunders, United States (Feb. 2001).

Lin, V.W., et al., "Functional Magnetic Stimulation of the Respiratory Muscles in Dogs," Muscle & Nerve 21 (8):1048-1057, John Wiley & Sons, United States (Aug. 1998).

Lotz, B.P., et al., "Preferential Activation of Muscle Fibers with Peripheral Magnetic Stimulation of the Limb," Muscle & Nerve, 12(8):636-639, John Wiley & Sons, United States (Aug. 1989).

Maffiuletti, N.A., et al., "Activation of Human Plantar Flexor Muscles Increases After Electromyostimulation Training," Journal of Applied Physiology 92(4):1383-1392, American Physiological Society, United States (Nov. 2001).

Maffiuletti, N.A., et al., "The Effects of Electromyostimulation Training and Basketball Practice on Muscle Strength and Jumping Ability," International journal of sports medicine 21(6):437-443, Thieme, Germany (Aug. 2000).

Magstim Company Limited, K051864 510(k) Summary, Magstim Rapid and Magstim Super Rapid, All pages (Dec. 2005).

Magstim Company US, LLC, K060847 510(k) Summary, Magstim Model 200-2 with Double 70mm Remote Coil, All pages (Sep. 2006).

Magstim Corporation US, K992911 510(k) Summary, Magstim Rapid, All pages (Jan. 2000).

Man, W.D-C., et al., "Magnetic Stimulation for the Measurement of Respiratory and Skeletal Muscle Function," The European Respiratory Journal 24(5):846-60, European Respiratory Society, England (2004).

Mantovani, A., et al., "Applications of Transcranial Magnetic Stimulation to Therapy in Pyschiatry," Psychiatric Times 21(9), Intellisphere, 29 pages (Aug. 2004).

Markov, M.S., "Pulsed Electromagnetic Field Therapy History, State of the Art and Future," Environment Systems and Decisions 27(4):465-475, Springer (Dec. 2007).

Mettler J.A., et al., "Low-Frequency Electrical Stimulation With Variable Intensity Preserves Torque," Journal of Electromyography and Kinesiology : Official Journal of the International Society of Electrophysiological Kinesiology 42:49-56, Oxford:Elsevier, England (Oct. 2018).

Mogyoros, I., et al., "Strength-Duration Properties of Human Peripheral Nerve," Brain 119(Pt 2):439-447, Oxford University Press, England (Apr. 1996).

Morrissey. M., "Electromyostimulation from a Clinical Perspective," Sports Medicine 6(1):29-41, Springer International, New Zealand (Aug. 1988).

Mustafa, B., "Design and Construction of a Low Cost dsPIC Controller Based Repetitive Transcranial Magnetic Stimulator TMS," Journal of medical systems 34(1):15-24, Kluwer Academic/Plenum Publishers, United States (2010).

Neotonus, Inc., K973096 510(k) Summary, Neotonus Model 100 Muscle Stimulator System, All pages (Jun. 1998).

Neotonus, Inc., K973929 510(k) Summary and FDA Correspondence, Neotonus, All pages (May 1998).

Neyroud, D., et al., "Comparison of Electrical Nerve Stimulation, Electrical Muscle Stimulation and Magnetic Nerve Stimulation to Assess the Neuromuscular Function of the Plantar Flexor Muscles," European journal of applied physiology 115(7):1429-1439, Springer-Verlag, Germany (2015).

Nielsen, J.F., et al., "A New High-frequency Magnetic Stimulator With an Oil-cooled Coil," Journal of Clinical Neurophysiology 12(5):460-467, Lippincott Williams & Wilkins, United States (Sep. 1995).

Novickij, V., et al., "Compact Microsecond Pulsed Magnetic Field Generator for Application in Bioelectronics," Elektronika ir Elektrotechnika 19(8):25-28 (Oct. 2013).

Novickij, V., et al., "Design and Optimization of Pulsed Magnetic Field Generator for Cell Magneto-Permeabilization," Elektronika ir Elektrotechnika(Electronics and Electrical Engineering) 23(2):21-25 (Apr. 2017).

Novickij, V., et al., "Magneto-Permeabilization of Viable Cell Membrane Using High Pulsed Magnetic Field," IEEE Transactions on Magnetics 51(9), All pages (Sep. 2015).

Novickij, V., et al., "Programmable Pulsed Magnetic Field System for Biological Applications," IEEE Transactions on Magnetics 50(11):5 (Nov. 2014).

Nuerosoft Ltd., "Neurosoft—Neuro-MS Transcranial Magnetic Simulator Technical Manual," All pages (Nov. 2014).

Oliveira, P.DE., et al., "Neuromuscular Fatigue After Low-and Medium-frequency Electrical Stimulation in Healthy Adults," Muscle & Nerve 58(2):293-299, John Wiley & Sons, United States (Aug. 2018).

Pain Management Technologies, "Pain Management Technologies Product Catalog," (2012).

(56) References Cited

OTHER PUBLICATIONS

Photograph, Alleged Photograph of Components of a Salus Talent Pop Double Device with an Aalleged Manufacture date of Nov. 14, 2012, 1 page.

Platil, A., "Magnetopneumography Using Optical Position Reference," Sensor Letters 11(1):69-73, ResearchGate (2013).

Pohanka, J., et al., "An Embedded Stereovision System: Aspects of Measurement Precision," 12th Biennial Baltic Electronics Conference, pp. 157-160 (Oct. 2010).

Porcari, J.P., et al., "Effects of Electrical Muscle Stimulation on Body Composition, Muscle Strength, and Physical Appearance," Journal of Strength and Conditioning Reasearch 16(2):165-172, Human Kinetics Pub., United States (May 2002).

Porcari, J.P., et al., "The Effects of Neuromuscular Electrical Stimulation Training on Abdominal Strength, Endurance, and Selected Anthropometric Measures," Journal of Sports Science and Medicine 4(1):66-75, Dept. of Sports Medicine, Turkey (Mar. 2005).

Pribula, O. and Fischer, J., "Real Time Precise Position Measurement Based on Low-Cost CMOS Image Sensor," IEEE, 5 pages (2011).

Pribula, O., et al., "cost-effective Image Acquisition System for Precise Pc-based Measurements," Przeglad Elektrotechniczny (Electrical Review), 2011, pp. 259-263.

Pribula, O., et al., "Optical Position Sensor Based on Digital Image Processing: Magnetic Field Mapping Improvement," Radioengineering 20 (1):55-60, (Apr. 2011).

Pribula, O., et al., "Real-Time Video Sequences Matching Spatio-Temporal Fingerprint," IEEE, 911-916 (Jun. 2010).

Prouza, O., et al., "High-Intensity Electromagnetic Stimulation Can Reduce Spasticity in PostStroke Patients," International Journal of Physiotherapy 5(3):87-91 (2018).

Prouza, O., "Targeted Radiofrequency Therapy for Training Induced Muscle Fatigue—Effective or Not?," International Journal of Physiotherapy 3(6):707-710 (Dec. 2016).

PTAB-IPR2021-00296, U.S. Pat. No. 10,493,293, Petition for Inter Partes Review, Dec. 14, 2020, 117 pages.

PTAB-IPR2021-00312, U.S. Pat. No. 10,478,634, Petition for Inter Partes Review, Dec. 14, 2020, 108 pages.

PTAB-PGR2021-00015, U.S. Pat. No. 10,709,895, Petition for Post-Grant Review, Dec. 14, 2020, 140 pages.

PTAB-PGR2021-00016, U.S. Pat. No. 10,709,895, Petition for Post-Grant Review, Dec. 14, 2020, 144 pages.

PTAB-PGR2021-00017, U.S. Pat. No. 10,632,321, Petition for Post-Grant Review, Dec. 14, 2020, 121 pages.

PTAB-PGR2021-00018, U.S. Pat. No. 10,632,321, Petition for Post-Grant Review, Dec. 14, 2020, 140 pages.

PTAB-PGR2021-00020, U.S. Pat. No. 10,695,575, Petition for Post-Grant Review, Dec. 14, 2020, 112 pages.

PTAB-PGR2021-00021, U.S. Pat. No. 10,695,575, Petition for Post-Grant Review, Dec. 14, 2020, 117 pages.

PTAB-PGR2021-00022, U.S. Pat. No. 10,709,894, Petition for Post-Grant Review, Dec. 14, 2020, 119 pages.

PTAB-PGR2021-00023, U.S. Pat. No. 10,709,894, Petition for Post-Grant Review, Dec. 14, 2020, 136 pages.

PTAB-PGR2021-00024, U.S. Pat. No. 10,695,576, Petition for Post-Grant Review, Dec. 14, 2020, 136 pages.

PTAB-PGR2021-00025, U.S. Pat. No. 10,695,576, Petition for Post-Grant Review, Dec. 14, 2020, 135 pages.

Radakovic T. and Radakovic N., "The Effectiveness of the Functional Magnetic Stimulation Therapy in Treating Sciatica Syndrome," Open Journal of Therapy and Rehabilitation 3(3):63-69 (2015).

Riehl., M., "Chapters: TMS Stimulator Design" The Oxford Handbook of Transcranial Stimulation, Wasserman, E.M., ed., pp. 13-23, Oxford University Press, 26 pages, United Kingdom (2008).

Roots, H., and Ranatunga, K.W., "An Analysis of the Temperature Dependence of Force, During Steady Shortening at Different Velocities, in (Mammalian) Fast Muscle Fibres," Journal of Muscle Research and Cell Motility 29(1):9-24, Springer, Netherlands (Jun. 2008).

Salus Talent Pop, The first sales bill, Authorization No. 20120221-41000096-66667961, 2 pages, (Feb. 2012).

Sargeant, A.J., "Effect of Muscle Temperature on Leg Extension Force and Short-term Power Output in Humans," European Journal of Applied Physiology and Occupational Physiology 56(6):693-698, Springer Verlag, Germany (Sep. 1987).

Schaefer, D.J., et al., "Review of Patient Safety in Time-Varying Gradient Fields," Journal of Magnetic Resonance Imaging, 12:20-29, Wiley-Liss, United States (Jul. 2000).

Shimada, Y., et al., "Effects of therapeutic magnetic stimulation on acute muscle atrophy in rats after hindlimb suspension," Biomedical Research 27(1):23-27, Biomedical Research Foundation, Japan (Feb. 2006).

Silinskas, V., et al., "Effect of Electrical Myostimulation on the Function of Lower Leg Muscles," Journal of strength and Conditioning Research 31(6):1577-1584, Human Kinetics Pub, United States (2017).

Sport-Elec S.A., K061914 510(k) Summary, Sport-Elec, All pages (Jul. 2007).

Sport-Elec S.A., K081026 510(k) Summary, Sport-Elec, All pages (Nov. 2008).

Stedman, T.L., "Aponeurosis—Apparatus," in Stedman's Medical Dictionary, 27th Edition, Pugh, M.B., ed., pp. 113-114, Lippincott Williams & Wilkins, Baltimore, MD (2000).

Struppler, A., et al., "Facilitation of Skilled Finger Movements by Repetitive Peripheral Magnetic Stimulation (RPMS)—A New Approach in Central Paresis.," NeuroRehabilitation 18(1):69-82, IOS Press, Amsterdam (2003).

Struppler, A., et al., "Modulatory Effect of Repetitive Peripheral Magnetic Stimulation on Skeletal Muscle Tone in Healthy Subjects: Stabilization of the Elbow Joint," Experimental Brain Research 157(1):59-66, Springer Verlag, Germany (Feb. 2004).

Suarez-Bagnasco, D., et al., "The Excitation Functional for Magnetic Stimulation of Fibers.," Annual International Conference of the IEEE Engineering in Medicine and Biology Society, IEEE Engineering in Medicine and Biology Society, Annual International Conference, 2010:4829-4833, IEEE, United States (2010).

Swallow, E.B., et al., "A Novel Technique for Nonvolitional Assessment of Quadriceps Muscle Endurance in Humans," Journal of Applied Physiology 103(3):739-746, American Physiological Society, United States (Sep. 2007).

The Magstim Company Ltd, K080499 510(k) Summary, Magstim Double 70mm Air Film Coil, All pages (Dec. 2008).

The Magstim Company Ltd., K130403 510(k) Summary, Magstim D702 coil, All pages (Aug. 2013).

Thermi Launches Arvati, powered by Thermi, with newest advances in True Temperature Controlled Radiofrequency Technology, 5 pages (2018).

Thompson, M.T., "Inductance Calculation Techniques—Part II: Approxmiations and Handbook Methods," Power Control and Intelligent Motion, 11 pages (Dec. 1999) http://www.pcim.com/.

Thompson, M.T., "Inductance Calculation Techniques—Part I: Classical Methods," Power Control and Intelligent Motion, 25(12):40-45, (Dec. 1999) http://www.pcim.com/.

Tomek, J., et al., "Magnetopneumography—Incorporation of optical position reference," Journal of Electrical Engineering, All pages (2012).

Torbergsen, T., "Abstracts of the International Course and Symposium in Single Fibre EMG and Quantitative EMG Analysis. Tromsø, Norway, Jun. 4-8, 1984," Muscle & Nerve 9(6):562-574, John Wiley & Sons, United States (Jul.-Aug. 1986).

Vance, C., et al., "Effects of Transcutaneous Electrical Nerve Stimulation on Pain, Pain Sensitivity, and Function in People with Knee Osteoarthritis," Physical Therapy 92:898-910 (2012).

Wada, K., et al., "Design and Implementation of Multi-Frequency Magnetic Field Generator Producing Sinusoidal Current Waveform for Biological Researches," IEEE, 9 pages (2016).

Ward, A.R. and Shkuratova, N., "Russian Electrical Stimulation: The Early Experiments," Physical therapy, 82(10):1019-1030, Oxford University Press, United States (2002).

Weiss, R.A., et al., "Induction of Fat Apoptosis by a Non-Thermal Device: Mechanism of Action of Non-Invasive High-Intensity Elec-

(56) References Cited

OTHER PUBLICATIONS tromagnetic Technology in a Porcine Model," Lasers in surgery and medicine 51(1):47-53, Wiley-Liss, United States (Jan. 2019).
Weng, O., "Electromagnetic Activation of the Calf Muscle Pump," UMI Dissertation Publishing (2014).
Yacyshy, A.F., et al., "The Inclusion of Interstimulus Interval Variability Does Not Mitigate Electrically-evoked Fatigue of the Knee Extensors," European Journal of Applied Physiology 120(12):2649-2656, Springer-Verlag, Germany (Sep. 2020).
Zao Okb Ritm, Electroneurostimulants, Transdermal Scenar-NT Instructions, All Pages (Nov. 2013).
Zao Okb Ritm, Percutaneous Electrical Stimulators With Individual Biofeedback Dosing Impact on Reflex Zones, All pages (Jul. 1905).
Zhang, G., et al., "A Method of Nerve Electrical Stimulation by Magnetic Induction," Annual International Conference of the IEEE Engineering in Medicine and Biology Society 2009:622-625, IEEE, United States (2009).
Zhi-De, D., "Electromagnetic Field Modeling of Transcranial Electric and Magnetic Stimulation: Targeting, Individualization, and Safety of Convulsive and Subconvulsive Applications," Academic Commons (2013).
Zhu, Y., et al., "Magnetic Stimulation of Muscle Evokes Cerebral Potentials by Direct Activation of Nerve Afferents: A Study During Muscle Paralysis," Muscle & Nerve 19(12):1570-1575, John Wiley & Sons, United Sates (Dec. 1996).
Kotz, Y., "Theory and Practice of Physical Culture," Training of Skeletal Muscle With Method of Electrostimulation, 64-67 (Mar. 1971).
Kotz, Y., "Theory and Practice of Physical Culture," Training of Skeletal Muscle With Method of Electrostimulation, 66-72 (Apr. 1971).
Werner, R., Magnetotherapy, Pulsating energy resonance therapy, 107 pages (Jun. 2007).
*BTL Industries, Inc. v. Allergan PLC et al* DDE-1-19-cv-02356, Complaint for Patent Infringement and Exhibits 1-34, 375 pages (Dec. 2019).
*BTL Industries, Inc. v. Allergan PLC et al* DDE-1-19-cv-02356, Order Granting Stipulation to Stay, Oct. 1, 2020, 1 page.
Prouza, O., "Ex-Post Analyza Spot Rebnich Dani," All pages, (2008).
Rutkove, S., "Effects of Temperature on Neuromuscular Electrophysiology," Muscle & Nerve 24(7):867-882, John Wiley & Sons, United States (Jul. 2001).
*Lumenis Ltd. v. BTL Healthcare Technologies A.S.*, PTAB-IPR2021-01273, U.S. Pat. No. 10,478,634, Petition for Inter Partes Review, Aug. 13, 2021, 70 pages.
*Lumenis Ltd. v. BTL Healthcare Technologies A.S.*, PTAB-IPR2021-01273, Declaration of Dr. Marom Bikson (EX1002), Aug. 13, 2021, 225 pages.
*Lumenis Ltd. v. BTL Healthcare Technologies A.S.*, PTAB-IPR2021-01278, U.S. Pat. No. 10,709,894, Petition for Inter Partes Review, Aug. 13, 2021, 85 pages.
*Lumenis Ltd. v. BTL Healthcare Technologies A.S.*, PTAB-IPR2021-01278, Declaration of Dr. Marom Bikson (EX1002), Aug. 13, 2021, 255 pages.
*Lumenis Ltd. v. BTL Healthcare Technologies A.S.*, PTAB-IPR2021-01280, U.S. Pat. No. 10,478,634, Petition for Inter Partes Review, Aug. 13, 2021, 69 pages.
*Lumenis Ltd. v. BTL Healthcare Technologies A.S.*, PTAB-IPR2021-01280, Declaration of Dr. Marom Bikson (EX1002), Aug. 13, 2021, 235 pages.
*Lumenis Ltd. v. BTL Healthcare Technologies A.S.*, PTAB-IPR2021-01285, U.S. Pat. No. 10,709,894, Petition for Inter Partes Review, Aug. 13, 2021, 79 pages.
*Lumenis Ltd. v. BTL Healthcare Technologies A.S.*, PTAB-IPR2021-01285, Declaration of Dr. Marom Bikson (EX1002), Aug. 13, 2021, 249 pages.
Agilent Technologies, Inc., "Agilent 33500 Series 30 MHz Function /Arbitrary Waveform Generator User's Guide," Publication No. 33520-90001 (Dec. 2010), 278 pages.
Agilent Technologies, Inc., "Agilent Announces 30 MHz Function/ Arbitrary Waveform Generators," Microwave J., URL: <https://www.microwavejournal.com/articles/9851-agilent-announces-30-mhz-function-arbitrary-waveform-generators> (Aug. 3, 2010), 8 pages.
Krueger, N. et al., "Safety and Efficacy of a New Device Combining Radiofrequency and Low-Frequency Pulsed Electromagnetic Fields for the Treatment of Facial Rhytides," J Drugs Dematol., 11(11):1306-1309 (Nov. 2012).
*Lumenis Be Ltd. v. BTL Healthcare Technologies A.S.*, PTAB-IPR2021-01402, U.S. Pat. No. 10,821,295 Petition for Inter Partes Review, Sep. 13, 2021, 81 pages.
*Lumenis Be Ltd. v. BTL Healthcare Technologies A.S.*, PTAB-IPR2021-01402, Declaration of Dr. Marom Bikson (EX1002), Sep. 13, 2021, 244 pages.
*Lumenis Be Ltd. v. BTL Healthcare Technologies A.S.*, PTAB-IPR2021-01403, U.S. Pat. No. 10,821,295 Petition for Inter Partes Review, Sep. 13, 2021, 84 pages.
*Lumenis Be Ltd. v. BTL Healthcare Technologies A.S.*, PTAB-IPR2021-01403, Declaration of Dr. Marom Bikson (EX1002), Sep. 13, 2021, 243 pages.
*Lumenis Be Ltd. v. BTL Healthcare Technologies A.S.*, PTAB-IPR2021-01404, U.S. Pat. No. 10,124,187 Petition for Inter Partes Review, Sep. 13, 2021, 82 pages.
*Lumenis Be Ltd. v. BTL Healthcare Technologies A.S.*, PTAB-IPR2021-01404, Declaration of Dr. Marom Bikson (EX1002), Sep. 13, 2021, 245 pages.
*Lumenis Be Ltd. v. BTL Healthcare Technologies A.S.*, PTAB-IPR2021-01405, U.S. Pat. No. 10,124,187 Petition for Inter Partes Review, Sep. 13, 2021, 86 pages.
*Lumenis Be Ltd. v BTL Healthcare Technologies A.S.*, PTAB-IPR2021-01405, Declaration of Dr. Marom Bikson (EX1002), Sep. 13, 2021, 247 pages.
Ruiz-Esparza, J. & J. Barba Gomez, "The Medical Face Lift: A Noninvasive, Nonsurgical Approach to Tissue Tightening in Facial Skin Using Nonablative Radiofrequency," Dermatol Surg, 29(4):325-32 (Apr. 2003).
Turley, J., "Agilent Technologies Announces 30 MHz Function/ Arbitrary Waveform Generators with Unparalleled Signal Accuracy," Elec. Eng'g J., URL: <https://www.eejournal.com/article/20100804-03/> (Aug. 4, 2010), 8 pages.
*Lumenis Be LTD. v. BTL Healthcare Technologies A.S.*, PTAB-IPR2022-00126, U.S. Pat. No. 10,695,576 Petition for Inter Partes Review, Nov. 10, 2021, 83 pages.
*Lumenis Be LTD. v. BTL Healthcare Technologies A.S.*, PTAB-IPR2022-00126, Declaration of Dr. Marom Bikson (EX1002), Nov. 10, 2021, 263 pages.
*Lumenis Be LTD. v. BTL Healthcare Technologies A.S.*, PTAB-IPR2022-00127, U.S. Pat. No. 10,695,576 Petition for Inter Partes Review, Nov. 10, 2021, 84 pages.
*Lumenis Be LTD. v. BTL Healthcare Technologies A.S.*, PTAB-IPR2022-00127, Declaration of Dr. Marom Bikson (EX1002), Nov. 10, 2021, 269 pages.
Hera Estetik Medikal, "LIPOSTAR" dated Jul. 7, 2014. https://www.youtube.com/watch?v=-R70nFIK9go, accessed Dec. 15, 2021.
Marek Heinfarth, "LipoStar" dated Jan. 10, 2013. https://www.youtube.com/watch?v=hZurkn8iU_U, accessed Dec. 15, 2021.
Hera Estetik Medikal, "Lipostar Manyetik incelme" https://www.heraestetik.com/en/urun-detay/liposter-manyetik-incelme, accessed Dec. 15, 2021.

\* cited by examiner

HIGH POWER TIME VARYING MAGNETIC FIELD THERAPY

PRIORITY CLAIMS

This Application is a Continuation-in-Part of U.S. patent application Ser. No. 14/926,365 filed Oct. 29, 2015, which is a Continuation-in-Part of U.S. patent application Ser. No. 14/789,156 filed Jul. 1, 2015. This Application is also a Continuation-in-Part of U.S. patent application Ser. No. 14/789,658 filed Jul. 1, 2015. This Application also claims priority to U.S. Provisional Patent Application No. 62/441,805 filed Jan. 3, 2017. The Application listed above are incorporated herein by reference.

BACKGROUND OF THE INVENTION

Magnet therapy uses the influence of magnetic flux on biological tissue. Electric current is induced in the tissue due to voltage change which causes a polarization of the cell membrane. One of fundamental phenomenon of electric current in biological tissue is a transfer of neural excitation or muscle contraction. The intensity of the effect is dependent on the magnetic flux density, repetition rate of the pulses, pulse time duration or envelope of the stimulation signal.

Water and biological molecules are diamagnetic substances. The magnetic field is not affected by diamagnetic substances. Therefore no loss of intensity or magnetic flux density occurs when passing through the biological structure or tissue.

Magnet therapy originally used permanent magnets with a stationary magnetic field. Natural magnets were applied especially to acupuncture points, or to the location of pain. Thereafter natural magnets were replaced by synthetic magnets and electromagnets of stationary magnetic field of higher induction than permanent magnets. In the last few decades, therapeutic methods have used mainly a pulsed magnetic field.

Existing methods of magnetic therapy generally tend to be limited to the key parameters of magnetic flux density and repetition rate. High values of magnetic flux density are reached at low repetition rate or vice versa. These combinations limit the effectiveness of muscle therapy at higher repetition rates over 50 Hz. Therefore the stimulation of deep structures or stimulation by high repetition rates or the combination of both is limited. Existing designs do not provide any device and/or method for stimulating biological structure at repetition rate over 50 Hz and magnetic flux density sufficient to cause at least partial muscle contraction repetitively. Additionally existing methods do not disclose time duration of the therapy.

Existing methods are also not able to provide stimulation of biological structures by pulsed magnetic field at repetition rates which exceed the frequency resolution of the biological structure. Some systems also require making physical contact with the patient since the magnetic field is weak or the stimulation signal cannot be transferred without the electrical contact. Generally, these known methods are limited to repetition rates over 50 Hz in order to provide biological structure stimulation. Furthermore, repetition rates exceeding 100 Hz are not utilized. The therapeutic methods at higher repletion rates over 100 Hz are provided only by electrotherapeutic methods.

Presently, muscle contraction leading to strengthening, training, myorelaxation or analgesic effect at higher repetition rates over 50 Hz and at sufficient intensity stimulus may be achieved only by direct current therapy. However, direct current methods require contact with the patient and even may be invasive. These methods can result in skin irritation, painful application especially for the stimulus of higher intensity, discomfort during the treatment, lack of deep tissue stimulation by non-invasive methods, and a lack of patient compliance with a prescribed therapy due to these factors.

SUMMARY OF THE INVENTION

The present invention generally relates to methods using the influence of magnetic and induced electric field on biological structure. The magnetic field is time-varying and high powered therefore the method is based on a value of magnetic flux density sufficient to induce at least partial muscle contraction.

In a first aspect, a method provides stimulation of biological structure using magnetic field at repetition rates exceeding 50 Hz for purpose of at least a partial muscle contraction.

In another aspect, the stimulation utilizes non-invasive and/or contactless transfer of the stimulation signal from an applicator to biological structure to evoke the action potential of the biological structure to induce at least partial muscle contraction. The applicator may include a source of magnetic field e.g. a coil.

The method may provide a non-invasive transfer of a stimulation signal from an applicator to biological structure to evoke the action potential of biological structure.

The method may use a peak to peak magnetic flux density on a coil surface at least 0.2 T, 0.4 T, 1.5 T, 2 T, or at least 3 T. The repetition rate may exceed 50 Hz, 80 Hz, 90 Hz, 100 Hz or 120 Hz, and up to 150 Hz, with preferable repetition rate up to 700 Hz. with initial or successive treatments lasting several seconds or longer, for example, for at least 5, 10, 30, 60, 120 or 240 seconds, or longer. The pulse width is in the range of tens to hundreds of microseconds.

In another aspect of the invention, a neuromuscular plate is stimulated causing an at least partial contraction of the muscle. The muscle is contracted at higher repetition rates and the contraction is stronger and more efficient for improving the muscle strength. The method is especially useful for deep muscles, major muscles, and for treatment of patients with high value of BMI. Deep muscle is the muscle underneath the superficial muscle. Muscle tissues may be selectively stimulated and the magnetic flux density of the stimulation may be adjusted based on patient characteristics or input. Treatment time can be shortened to a minimum due to selective stimulation of targeted muscles. Additionally, the treatment may be non-invasive or even contactless due to the high value of magnetic flux density. The patient may be treated without removing clothing, thereby reducing patient discomfort.

In further aspect, a neuromuscular plate and/or the nerve innervating the neuromuscular plate is stimulated and at least partial muscle contraction is provided. The muscle may be contracted at higher repetition rates and the contraction is stronger. Therefore the stimulation is more efficient for reducing the number and/or volume of adipocytes and enhancing the visual appearance of the treated body area via targeted muscle contraction. Additionally, strong muscle contractions at higher repetition rates cause mechanical movement of all the layers in proximity of the contracted muscle. This method therefore causes remodeling and/or neogenesis of the collagen and elastin fibres.

The present methods may be used for enhancing visual appearance of body areas including adipose tissue reduction, muscle toning, muscle shaping, body contouring, body shaping, skin tightening, cellulite treatment, circumferential reduction, breast enhancement and/or lip enhancement.

The target biological structure may be a joint. Due to the pulsed magnetic field, the dynamic fluid properties of synovial fluid are improved and muscle contraction is achieved, contributing to positioning of the joint by short movements of the joint compartments.

In another aspect of the invention the repetition rate may exceed the frequency resolution of the structure. The magnetic flux density of the stimulation signal may increase over time. Therefore the envelope of resulting stimulation signal is increasing and it is perceived by the stimulated biological structure as a continuous stimulation signal instead of plurality of discrete stimuli. The envelope may be preferably triangular and other shapes may be used as well. This method is effective for stimulation of denervated muscle.

The envelope may be generated by time-varying magnetic flux density and/or repetition rate and/or impulse duration.

In a further aspect of the invention, the method stimulates the biological structure via a magnetic stimulation signal of at least 100 Hz, where the stimulation is intended for at least partial muscle contraction. The pulsed magnetic field induces the electric current which may provide myorelaxation. The stimulation signal repetition rate may be at least 120 Hz or at least 140 Hz.

Alternatively the treatment may combine a plurality of different treatment methods using different approaches. Such a combination may be magnetic treatment in combination with optical treatment, electromagnetic treatment such as radiofrequency treatment and/or treatment using mechanical interactions such as ultrasound wave, acoustic wave, shock wave treatment (SWT) which may be unfocused or focused.

The present invention relates to device and methods for treating a patient by a magnetic and/or electromagnetic field. The application of the magnetic and/or electromagnetic field is provided by at least one energy delivery element. The device may be used for treatment or focused remodeling of adipose tissue by reducing number and/or value of lipid-rich cells.

The present device and methods as described below provide combined treatment by high power magnetic and/or electromagnetic field, particularly radiofrequency treatment. The combined treatment may be provided by one device using at least one coil for providing both treatments, the magnetic and even the electromagnetic treatment.

The device may include a plurality of energy delivery elements. The positioning of the plurality of the energy delivery elements may be controlled by a mathematic method including monitoring a characteristic quantity of an operation parameter.

The energy delivery element may be used as an energy source for another functional part of an applicator, e.g. e blower, or for providing energy to light emitting device providing still another treatment.

GLOSSARY

Figure 1:
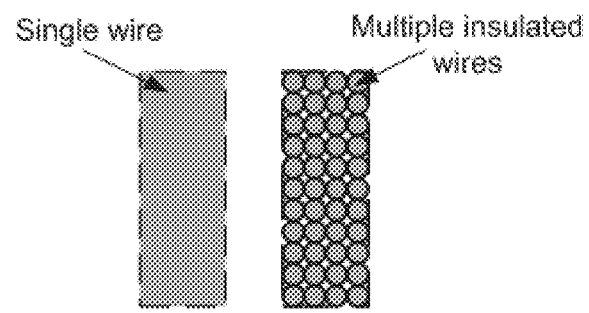
FIG. 1 is a cross section view of a coil winding.

Biological structure/target biological structure includes a cell, a neuron, a nerve, a muscle fibre, a tissue, a filament.

Stimulation signal refers to a magnetic flux density inducing an electric current in the biological structure.

Active response of a biological structure includes a change in a permeability of cell membrane for ions or any other particles, generation of an action potential, at least partial muscle contraction, a change of rheological properties of synovial fluid.

Sensory intensity is the stimulation intensity when the patient feels the first perception of the induced current flow in the stimulated biological structure.

Motoric intensity is the stimulation intensity when the patient registers the first muscle contraction.

Noxious intensity is the stimulation intensity when the patient recognizes first painful stimulus.

Impulse refers to the only one biphasic magnetic stimulus.

Pulse refers to a period of stimulation signal consisting of at least one biphasic stimulus and a time duration of no stimulation, i.e. time duration between two impulses from rise edge to next rise edge.

Repetition rate refers to frequency of firing the pulses; it is derived from the time duration of a pulse.

Envelope refers to use of a repetition rate sufficiently high so that the muscle reacts as if the stimulus is continuous and not a plurality of discrete stimuli.

Modulated means that during the stimulation the magnetic flux density and/or repetition rate is changed to prevent adaptation of the muscle.

Isometric contraction means the muscle is activated, but instead of being allowed to lengthen or shorten, it is held at a constant length.

Duty cycle is the ratio of the duration of active stimulation to the entire period.

Conventional non-invasive and/or invasive aesthetic medicine applications refer to aesthetic medicine applications based on application of mechanical waves, e.g. ultrasound or shock wave therapy; or electromagnetic waves, e.g. radiofrequency or diathermy treatment or light treatment, such as intense pulsed light or laser treatment; or mechanical stimulation, e.g. positive or negative pressure, rollerball, massage etc.; or thermal treatment, e.g. cryotherapy; or electrotherapy method; or mesotherapy method and or any combination thereof.

Neural system includes central neural system and/or peripheral neural system.

Central neural system (CNS) includes brain and/or spinal cord.

Muscle includes at least one of muscle fibre, muscle tissue or group, neuromuscular plate or nerve innervating the at least one muscle fibre.

Deep muscle refers to a muscle that is at least partly below superficial muscles and/or to the muscle that is covered by the thick layer of other tissue, e.g. mostly adipose tissue and/or the skin, with thickness 0.5, 1, 2, 3, 4, 5 or more centimetres.

Induced energy refers to energy stimulating the target neural structure, the amount of induced energy corresponds to repetition rate, magnetic flux density and impulse duration.

Adipose tissue refers to at least one lipid rich cell, e.g. adipocyte.

Bolus refers to a layer of fluid material, e.g. water or fluid solution of ceramic particles, preferably enclosed in a flexible sac made of biocompatible material.

Hardware panel refers to at least one hardware component used for controlling the optical and/or magnetic treatment. The hardware panel includes at least one of input interface for inputting treatment parameters by an operator and processing unit for controlling the optical and/or magnetic treatment.

Treatment parameters refer to one or more of: magnetic flux density, repetition rate, impulse duration, wavelength, power flux density and/or energy flux density of the optical waves, pulse width, modulation, treatment protocol or treatment duration.

Optical waves include electromagnetic waves from ultraviolet, visible and infrared spectrum ranges, i.e. the waves of wavelength in the range of 190 to 13000 nm.

Optical waves generating device refers to laser or laser diode, light emitting diode (LED), electric discharge source, incandescent source, fluorescent source, luminescent source, electroluminescent source etc.

Optical treatment refers to treatment by optical waves.

DETAILED DESCRIPTION OF THE INVENTION

Electric current is induced in the stimulated biological structure during pulsed magnet therapy. A distribution of a magnetic field is uniform in the biological structure. Particles (e.g. atoms, ions, molecules etc.) in the biological structures are affected by the magnetic field and permeability of a cell membrane also increases.

Due to increased permeability of the cell membrane, an action potential may occur and a partial or full muscle contraction is induced. Convenient repetition rates may cause pain relief and/or myorelaxation, different repetition rate may cause stimulation of denervated muscle, and further different repetition rates may improve movability of a joint.

Advantages of the present magnet therapy include: affecting the deep structures which are problematically stimulated by superficial stimulation; non-invasive or non-contact application of magnetic flux, it may be applied even with clothes; absolute non-invasiveness of the stimulation and elimination of skin irritation in the place of magnetic field application; high rate of acceptability of the stimulation by patients; elimination of stimulation side effects; elimination necessity of applicator made of biocompatible materials; providing a clean and sterile applicator on the highest level; possibility of local or area treatment.

It is to be understood that the method is not limited to the particular applications and that the method may be practiced or carried out in various ways.

The present methods may use magnetic stimulation of magnetic flux density at least sufficient to cause active response of a biological structure at the repetition rates at least 50 Hz. The broad spectrum of application of biological structure stimulation by magnetic field is achieved due to high repetition rates and/or high value of magnetic flux density. Methods are intended especially for at least partial muscle contraction.

The magnetic stimulation of the biological structure has various applications for enhancing visual appearance of the contour body area. High density magnetic field reaches such values which may be used for: adipose tissue reduction, wherein the adipose tissue reduction is achieved by reduction of number and/or volume of adipose cells; muscle toning, wherein the muscle appearance enhancement is achieved by adipose tissue reduction with no muscle bulking; muscle shaping, wherein the muscle appearance enhancement is achieved by adipose tissue reduction and/or muscle bulking; body contouring, wherein the silhouette appearance enhancement is achieved by adipose tissue reduction with no muscle bulking; body shaping, wherein the silhouette appearance enhancement is achieved by adipose tissue reduction and/or muscle bulking; skin tightening, wherein the skin appearance enhancement is achieved by obtaining smoother and younger appearance, including wrinkles reduction; cellulite treatment, wherein the appearance enhancement is achieved by adipose tissue reduction, muscle contraction and/or elastic fibres neogenesis; circumferential reduction, wherein the reduction is achieved by adipose tissue reduction and/or the muscle bulking; breast enhancement, wherein the appearance enhancement effect is achieved by elevation or shape modification; lip enhancement, wherein the lip appearance enhancement is achieved by obtaining fuller and firmer appearance.

One application of time-varying magnetic field for enhancing the visual appearance of body area may be stimulation of a muscle by magnetic flux density for reducing the cellulite. The magnetic flux density is delivered through the skin to the neuromuscular plate and/or nerve innervating at least one muscle fibre. The electric current is induced in the target biological structure causing at least partial muscle contraction. The at least partial muscle contraction causes the movement of the skin and all the biological structures subtending epidermis. Additionally, the at least partial muscle contraction improves blood circulation by itself, or via the movement of the muscle in the vicinity including fibrous septae. Additionally, blood and/or lymph circulation is improved in the layers subtending epidermis since the muscle contraction moves the fibrous septae. Also local and/or adipose tissue metabolism is improved. The at least partial muscle contraction is more effective for adipose tissue metabolism as the value of magnetic flux density increases since the muscle contraction is stronger. The higher magnetic flux density effects the higher number of muscle fibres contraction and the more adipose tissue is reduced. Therefore the visual appearance of regions prone to cellulite is enhanced.

The method causes the circumferential reduction i.e. a reduction of the size of the treated body area. The method is mostly indicated for the regions with cellulite, especially for buttocks, abdomen, hips, thighs or arms. However, the indication is not limited to the mentioned regions and the method may be used for stimulation of any other body area.

The present method may provide a massage effect via the stimulation which is caused by the at least partial muscle contraction. Therefore the massage effect may be achieved by contactless methods instead of manual massage techniques or soft tissue techniques. The massage effect improves lymph circulation.

With the present method muscle contractions induced by the applied magnetic flux density help to tone the muscle providing a more attractive appearance. As the muscle structure is stimulated by time-varying magnetic field the entire limb may be moved due to the high power of the magnetic stimulation signal. Nevertheless, the method is not limited to the applications to the limbs and the method is able to be applied to stimulation of any muscle, e.g. gluteus maximus or any muscle/deep muscle to induce body contouring and/or body shaping effect and fat burn. Additionally, shortened and/or flabby muscles are stretched. The physical fitness of the patient is improved as well.

The present methods may also induce muscle contraction to reduce effect of skin laxity. Skin laxity may be caused by e.g. the aging process or increasing number and/or volume of adipose cells which pulls down the skin by gravity, rapid weight loss or skin stretching during the pregnancy. The muscles are stimulated by the induced electric current to contract. Repetitive contractions cause the muscles to obtain the tonus and flexibility. Therefore the skin appearance is enhanced by stimulating the flabby muscles. The effect of skin tightening is achieved. The method also stimulates the creation of the collagen and elastin fibres in the layers subtending the epidermis hence the skin obtains enhanced visual appearance. The method may be widely applied but not limited to application to the regions of neck, breasts, arms or abdomen. The method provides the smoother and younger appearance of the skin to the patient.

Similar methods of stimulation the muscle structure by time-varying magnetic field for inducing the at least partial muscle contraction may be used for treatment of wrinkles as well. Wrinkles are results of extrinsic and intrinsic factors. Nowadays, wrinkles are considered to be negative effect of natural aging process which decreases the production of collagen and elastin fibres and weakens the skin which becomes thinner. As the muscle stimulation by the magnetic flux density induces at least partial muscle contraction, the stimulation of collagen and elastin fibres neogenesis is improved. Additionally, the muscles subtending the stimulated region are toned and the skin gets a younger and enhanced visual appearance. Therefore, the effect of skin tightening is achieved.

The present methods may improve the neogenesis and remodelling of collagen fibres in the lips to reach a full, plump and firmer appearance. The magnetic flux density is applied to the lips by an applicator. Therefore the lips become fuller and firmer without any need of invasive method such as injection of the synthetic fillers, permanent makeup or the facial implants. The present method stimulates the remodelling and/or neogenesis of collagen fibres in a natural way. Additionally, the collagen is natural substance of the human body which provides the elasticity to the structure.

The collagen constitutes around 30% of proteins. Treatment by time-varying magnetic field may induce the neocollagenesis. The collagen may be treated by various repetition rates, e.g. in the range of 1 to 250 Hz, more preferably in the range of 10 to 100 Hz, or up to 700 Hz. However, the repetition rate of 25 Hz may be preferably used because the results achieved by stimulation of repetition rate of 25 Hz were the most significant. High value of magnetic flux density may improve the neocollagenesis more than low value of magnetic flux density. Hence the magnetic flux density may be at least 0.5 T, more preferably 1 T, most preferably at least 2 T, or up to 7 T.

The present methods may be used for enhancing the visual appearance of breasts. Cooper's ligament may be stimulated, improved and/or firmed by the at least partial muscle contraction. The muscle stimulation induces the elevation of the breast tissue. Additionally, the breast tissue is stimulated to be modified in a shape, wherein the shape includes the size and/or the contour of the breast tissue. Therefore the visual appearance is enhanced and breasts are more attractive for the patient. The present method is a non-invasive alternative for current aesthetic surgery method for the treatment of sagging breast tissue. The present method provides a patient a method of breast visual appearance enhancement without surgery. Therefore the method lacks post-surgery complications such as scars, postoperative pain or long recovery period. Various treatment protocols may be used.

The present invention provides new methods of aesthetic treatment of a patient focused on remodeling the buttocks of the patient.

In one application, the muscle stimulation may induce the same effect as muscle exercising of buttocks. During the stimulation of buttocks the magnetic field is targeted to stimulation of muscles shaping the buttocks, e.g. tensor fasciae latae muscle or at least one of gluteal muscles: maximus, medius or minimus. In one preferred application all three gluteal muscles may be stimulated. Further other muscles may be stimulated, e.g. abdominal muscles, spinal muscles and/or thoracic muscles. By the complex stimulation and muscle contraction in the target area the stimulated muscles are strengthened, toned, the cellulite may be reduced and dimples may be removed. Buttocks and even the patient's figure may be enhanced in visual shape appearance and become more attractive. Buttocks become wellshaped, round, firm, well-trained, toned, smoother, tight and lifted. The complex stimulation may reduce hips, an make perfect round and lifted buttocks, increasing the self-confidence of the patient.

In still another application the magnetic treatment may be used for improving sport performances, such as the sports where the movement technique may be important factor for the result, e.g. pole vaulting, ski jump or gymnastics. The magnetic treatment may be applied to motoric cortex of the patient. The magnetic treatment may improve the production of newly created neural interconnection during the learning the skill. Hence specific sport performance may be learned in shorter time period and/or less number of repetitions. Furthermore the magnetic treatment may improve the movement coordination and/or the jumping force.

Alternatively the magnetic treatment influencing sport performance may be used in combined treatment preferably for regeneration after sport performance and/or for recovering of the athletes after injuries by regenerating the muscles, improving local metabolism, preventing atrophy and/or by selective training of correct motion patterns.

Alternatively the magnetic treatment may be used for strengthening the muscle in natural way following the motion pattern, e.g. dumbbell exercise of biceps. In an exemplary application the repetition rate of the treatment may be constant, e.g. at least 5 Hz, more preferably at least 20 Hz, even more preferably at least 40 Hz, most preferably at least at least 80 Hz, and the amplitude of magnetic flux density may vary, e.g. the amplitude of magnetic flux density may rise for a defined time period and decrease for a defined time period. The magnetic flux density may be in the range of 0.1 to 2.5 T, more preferably at least 0.5 to 2 T, even more preferably at least 1 T, or up to 7 T. The strength of the at least partial muscle contraction may correspond with the value of magnetic flux density. This exemplary application may cause a motion corresponding with motion during dumbbell exercise of biceps.

The treatment is more efficient than standard workout in fitness since the machines strengthen only the isolated muscles. The results may be achieved in very short-time periods with minimal time of treatment. Without being limited, it is believed that the exercising of the gluteus medius may reduce the volume of the buttocks; exercising of the gluteus maximus may shape and/or lift the buttocks; exercising of the gluteus minimus may lift the buttocks.

The one approach is stimulating central neural system or peripheral neural structure and determining the feedback, e.g. muscle contraction.

In still another application of the invention, the time-varying magnetic field may be used for stimulation of neural structure to cause muscle stimulation. The muscle stimulation may occur during stimulation by envelopes of repetition frequencies below 100 Hz.

In the preferred application the magnet treatment may be combined with other treatment methods using different approaches, e.g. conventional non-invasive treatments. The combined treatment may be applied to the surroundings tissues around buttocks to reduce the cellulite around the buttocks and enhance the shape of the enhanced appearance of the buttocks. The surrounding tissues may be represented by e.g. abdomen, love handles, thighs or saddle bags.

The present methods may be provided by the magnetic stimulation device which contains no magnetic core, however, the magnetic core may also be used. The magnetic stimulation device may be cooled by a fluid, such as air. The total power consumption may be preferable, but is not limited to values below 1.3 kW. Convenient therapeutic apparatus is described in the U.S. patent application Ser. No. 14/789,156 or U.S. patent application Ser. No. 14/789,658, incorporated herein by reference.

A device for time variable magnetic field generation may include an energy source, an energy storage device, a switching circuit, a coil and possibly a core. The energy storage device accumulates tens of Joules of energy and the magnetic flux density induced by the coil is in the range of tenths of a Tesla to about one Tesla.

The coil may be made of insulated wires with a conductor diameter less than 3 mm even more preferably less than 0.5 mm and most preferably less than 0.05 mm. Smaller diameter and individual insulation of the wires significantly reduces self-heating of the coil and therefore increase efficiency of magnetic stimulation device. The coil may be flexibly attached in a casing of device. The casing may comprise a blower or blowers which ensure cooling of the coil.

Space between the insulated wires may be filled with a solid material so as to reduce the noise caused by vibrations. The coil is connected with an energy storage device which serves as a storage of energy.

The switch can be any kind of switch such as diode, MOSFET, JFET, IGBT, BJT, thyristor or a combination of them. The switch can be connected in parallel to the coil and the energy storage device, to eliminate reversal polarity of high voltage on the terminals of the energy source in the second half of the resonant effect. Therefore there is no need for additional protective circuits to protect the energy source from the negative voltage. Electric losses associated with such protective circuits are avoided. Energy use is reduced. The voltage drop in the energy storage device between first and second oscillation maximum during resonance is also reduced. Via the lower voltage drop, higher repetition rates of magnetic pulses and higher magnetic flux density may be achieved for treatment of the patient.

The coil of the magnetic stimulation device may be flexibly attached to casing of the device. The blower or blowers may be arranged to blow air on both sides of coil. Optionally, the coil may be a flat type coil.

FIG. 1 illustrates a cross section of winding of a coil for a magnetic stimulation device. The coil may be constructed from litz-wire, wherein each wire is insulated separately. Each individual conductor is coated with non-conductive material so the coil constitutes multiple insulated wires. Unlike existing magnetic coil conductors, the present coil is not made of bare wire e.g. litz-wire without insulation, or conductive tapes, conductive strips, or copper pipe with hollow inductors. The insulation of wires separately is a substantial improvement, since this leads to a significant reduction of the induced eddy currents. Power loss due to eddy currents, per single wire, is described by Equation 1 below. The small diameter wires of the present coil significantly reduce self-heating of the coil and therefore increases efficiency of the present magnetic stimulation device:

$$P_{EDDY} = \pi^2 \cdot B_P^2 \cdot d^2 \cdot f^2 / 6 \cdot k \cdot \rho \cdot D,$$ Eq. 1 where: $P_{EDDY}$ is power loss per unit mass (W·kg$^{-1}$); $B_p$ is the peak of magnetic field (T); f is frequency (Hz); d is the thickness of the sheet or diameter of the wire (m); k is constant equal to 1 for a thin sheet and 2 for a thin wire; $\rho$ is the resistivity of material ($\Omega$·m); D is the density of material (kg·m$^3$).

The individual insulation of each wire reduces eddy currents. The individually insulated wires may be wound either one by one or in a bundle of individually insulated wires so as to form a coil, which will serve as a magnetic field generator. The coil provides an improvement in the efficiency of energy transfer in the LC resonant circuit and also reduces or eliminates unwanted thermal effects.

The coil may have a planar coil shape where the individually insulated wires may have cross-section wires with conductor diameter less than 3 mm even more preferably less than 0.5 mm and most preferably less than 0.05 mm. The wires are preferably made of materials with higher density and higher resistivity e.g. gold, platinum or copper. The diameters of the single wires should be minimal. On the other hand the total diameter should be maximal because of inverse proportion between the cross-section of all wires forming the coil and the electrical resistance. Therefore the ohmic part of the heat is then lower. Eq. 2 describes power loss of the coil:

$$P_R = \rho \cdot l / S \cdot I^2 / m$$ Eq. 2 where: $P_R$ is the power loss heat dissipation (W); $\rho$ is the resistance ($\Omega$·m); l is the length of wire (m); S is the surface area (m$^2$); I is the current (A) and m is 1 kg of wire material.

Total power loss is (Eq.3):

$$P_{TOT} = P_{EDDY} + P_R$$ Eq. 3 where: $P_{TOT}$ is the total power losses (W·kg$^{-1}$); $P_{EDDY}$ is the power dissipation of eddy currents (W·kg$^{-1}$); $P_R$ is the power loss heat dissipation (W·kg$^{-1}$).

Dynamic forces produced by current pulses passing through the wires of the coil cause vibrations and unwanted noise. The individual insulated wires of the coil may be impregnated under pressure so as to eliminate air bubbles between the individual insulated wires. The space between wires can be filled with suitable material which causes unification, preservation and electric insulation of the system. Suitable rigid impregnation materials like resin, and elastic materials like PTE can be also used. With the coil provided as a solid mass, the vibrations and resonance caused by movements of the individual insulated wires are suppressed. Therefore noise is reduced.

The coil may be attached to the case of the applicator, such as a hand held applicator of the magnetic stimulation device; built-in applicator in e.g. chair, bed; or stand-alone applicator e.g. on mechanical fixture. The attachment may be provided by an elastic material e.g., silicone, gum; or other flexible manner. Connection with the coil of the applicator's case can be ensured by several points. The several fastening points ensure the connection of the coil to the casing by flexible material so that the main part of the coil and the main part of the casing of applicator are spaced apart. The spacing should be at least 0.1 mm so that air can easily flow. The gap between the coil and the casing can be used either for spontaneous or controlled cooling. The coil may optionally be connected to the case of the applicator by only one fastening point. The fastening points eliminate vibrations of wires which could be transferred to housing of the applicator and therefore reduce noise of the magnetic stimulation device.

The magnetic stimulation device may be cooled by a fluid, e.g. by a liquid or a gas. In the preferred embodiment the magnetic stimulation device is cooled by air.

Figure 2:
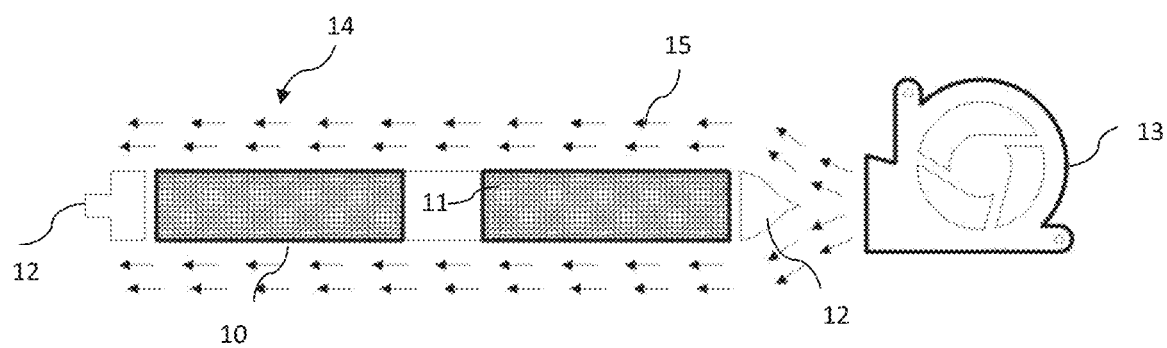
FIG. 2 is an illustrative embodiment of cross-section of the magnetic applicator.

FIG. 2 is a cross-section of the magnetic applicator which allows better flow on the lower and upper sides of the coil and thus more efficient heat dissipation. The magnetic stimulation device includes a coil 11, the circuit wires 11 and the fastening points 12 for connection of the coil to the casing of the applicator (not shown). The fastening points 12 are preferably made of flexible material however the rigid material may be used as well. The fastening points 12 may be located on the outer circumferential side of the coil. However, alternatively it is possible to put these fastening points to a lower or upper side of the coil.

The fastening points 12 connect the coil to the case of the applicator in at least one point. The fastening points 12 maintain the coil and the main part of the case of the applicator spaced apart so that fluid (which may be air or any liquid) can flow between them. At least one blower 13 can be placed around the circumference of the coil, or perpendicular to the coil. The blower can be any known kind of device for directing the fluid e.g. outer air directed into the case of the applicator. This arrangement of the blower allows air to bypass the coil from upper and lower (patient's) sides. In still another embodiment the outer air can be cooled before directing into the case. The blower can have an inlet placed around the circumference of the coil for injecting air, to remove heat from the coil. A connecting tube (not shown) can ensure connection of the applicator with the energy source and/or control unit of magnetic stimulation device. The connecting tube may also contain a conduit of the fluid.

The arrows 15 indicate the air flow through the applicator. This arrangement of the blower allows the air to bypass the coil from upper and lower (patient's) side. Outlet may be preferably placed on upper side of the casing. By placing the blower around the circumference of the coil instead of on the top/below the coil, the blower 13 does not interfere with the magnetic flux peak and therefore its lifespan and reliability is increased.

Figure 3:
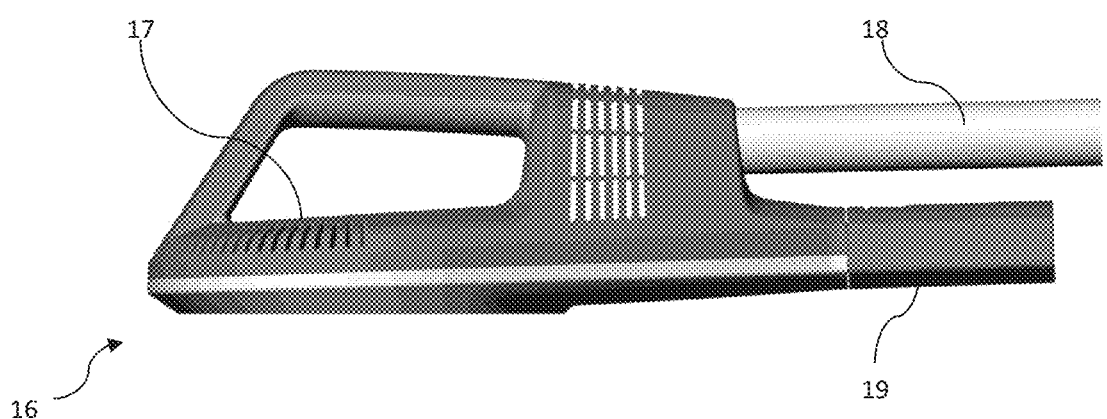
FIG. 3 is an illustrative embodiment of a casing of the magnetic applicator.

FIG. 3 is an illustrative embodiment of a casing of the magnetic applicator. The overview drawing contains casing itself 16, which might contain an outlet 17 preferably placed on upper side of the casing 16. A connecting tube 18 may not only ensure connection of the applicator with the energy source and/or control unit of magnetic stimulation device, but also connection to a source of the fluid; however the conduit of the fluid 19 may also be connected separately.

Figure 4A:
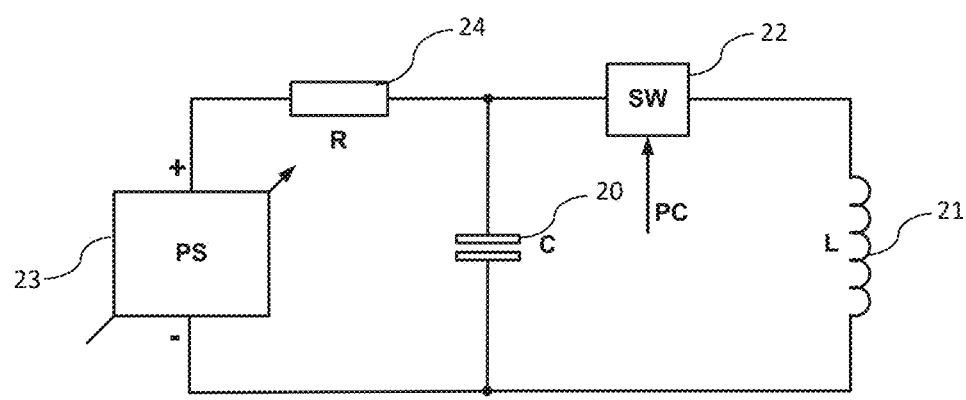
FIGS. 4A and 4B illustrates circuit for providing high power pulses to a stimulating coil.
Figure 4B:
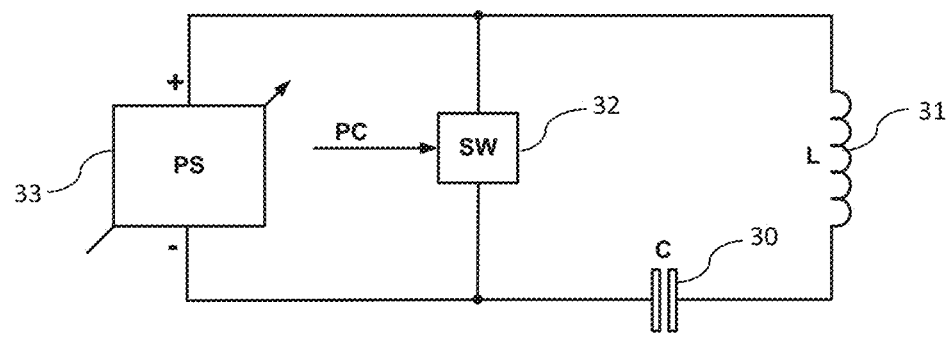

FIG. 4A and FIG. 4B illustrate circuits for providing high power pulses to the stimulating coil. FIG. 4A shows a circuit for providing high power magnetic pulses. FIG. 4B shows a circuit for providing high power pulses.

In FIG. 4A the circuits for providing high power pulses to the stimulating coil contain a series connection to the switch 20 and the coil 21. The switch 22 and the coil 21 together are connected in parallel with an energy storage device 20. The energy storage device 20 is charged by the energy source 23 and the energy storage device 20 then discharges through the switching device 22 to the coil 21.

During second half-period of LC resonance, the polarity on the energy storage device 20 is reversed in comparison with the energy source 23. In this second half-period, there is a conflict between energy source 23, where voltage on positive and negative terminals is typically thousands of Volts. The energy storage device 20 is also charged to the positive and negative voltage generally to thousands of Volts. As a result, there is in the circuit, consequently, twice the voltage of the energy source 23. Hence the energy source 23 and all parts connected in the circuit are designed for a high voltage load. Therefore, the protective resistors and/or protection circuitry 24 must be placed between energy source 23 and energy storage device 20. As a result a large amount of energy is transformed to undesired heat in the protective resistors and/or protection circuitry 24.

FIG. 4B shows a circuit for providing high power pulses for improved function of the magnet stimulation device. The coil 31 and an energy storage device 32 are connected in series and disposed in parallel to the switch 32. The energy storage device 30 is charged through the coil 31. To provide an energy pulse, controlled shorting of energy source 33 takes place through the switch 32. In this way the high voltage load at the terminals of the energy source 33 during the second half-period of LC resonance associated with known devices is avoided. The voltage on the terminals of energy source 33 during second half-period of LC resonance is a voltage equal to the voltage drop on the switch 32.

The switch 32 can be any kind of switch such as diode, MOSFET, JFET, IGBT, BJT, thyristor or their combination. Depending on the type of component the load of energy source 33 is reduced to a few Volts, e.g., 1-10 volts. Consequently, it is not necessary to protect the energy source 33 from a high voltage load, e.g., thousands of Volts. The use of protective resistors and/or protection circuits is reduced or eliminated. The present designs simplify the circuits used, increase efficiency of energy usage and provide higher safety.

Figure 5:
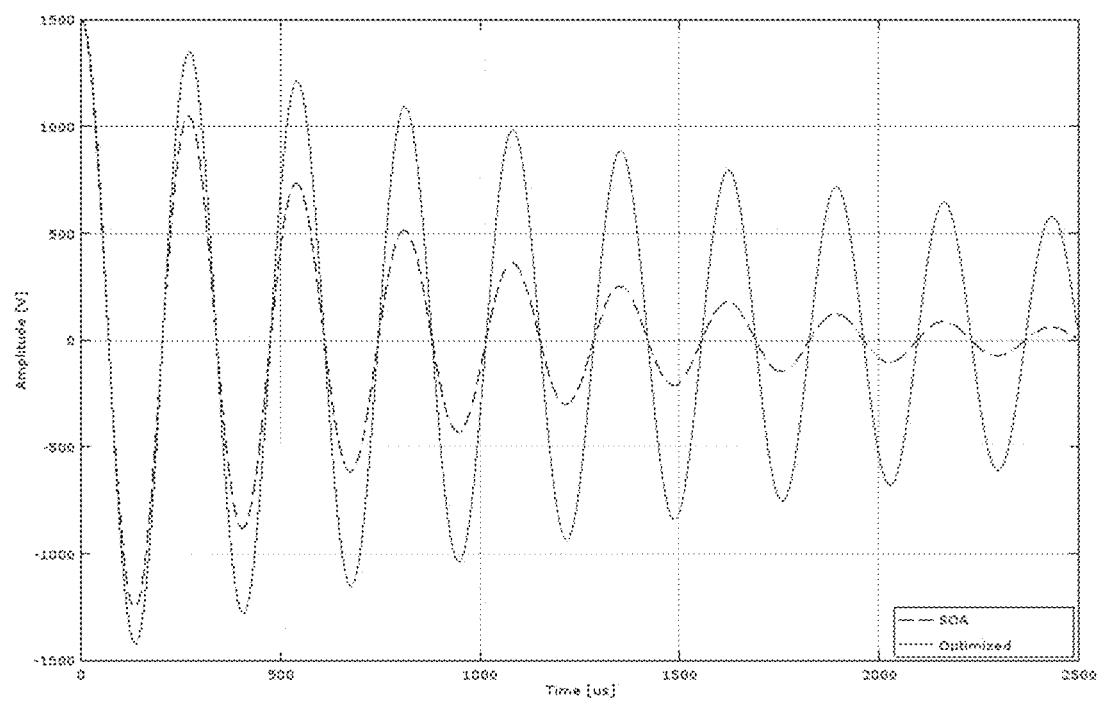
FIG. 5 is a graph showing voltage drop in the energy storage device.

FIG. 5 show an exponential voltage drop in the energy storage device. Energy savings during time-varying magnetic therapy may be characterized by reduced voltage drop in the energy storage device between the first, second and subsequent maximums of the resonant oscillation. The magnitude of the individual voltage oscillations is exponentially dampened up to establishing the energy balance. This allows increasing the maximum possible frequency/repetition rate of magnetic pulses, since the frequency/repetition rate is dependent on the speed with which it is possible to recharge the energy storage device. Since the energy storage device is recharged by the amount of energy loss during the previous pulse, it is possible to increase the frequency/repetition rate of the device up to hundreds of magnetic pulses per second without the need to increase the input power. The voltage drop between any of the successive amplitudes is not higher than 21%, even more preferably not higher than 14% and most preferably not higher than 7%.

The present invention provides a magnetic stimulation device and method of controlling the magnetic stimulation device using a plurality of magnetic field generating devices.

The magnetic stimulation device may include the at least one applicator, the at least one energy source and at least two magnetic field generating devices. However, in an alternative embodiment the magnetic stimulation device may include a plurality of applicators and/or plurality of energy sources. The plurality of applicators may be used for treatment of at least two cooperating muscle groups with different treatment effects. In an exemplary application e.g. the triceps brachii muscle may be treated to achieve myostimulation effects and the biceps brachii muscle may be treated to achieve myorelaxation effects.

The magnetic stimulation device may include a plurality of applicators. The applicator includes at least one magnetic field generating device which may be movable. The benefit of this embodiment is that the movement and/or positioning of the plurality of the applicators may be independent. Hence different parts of the patient's body may be treated simultaneously. Therefore the total treatment time is reduced and patient's downtimes are reduced as well. The movement of the at least one applicator may be automatic so that manual manipulation may not be needed. The movement of the at least one applicator may follow a predetermined trajectory or it may be random. In an alternative embodiment the movement of the plurality of applicators may be synchronized.

There is no necessity of constant movement of the applicator over a larger area. The applicator may remain in a stationary position relative to the patient for several seconds or longer, e.g. for at least 10, 30, 60, 120 or 240 seconds, or longer. The at least one applicator may be of such dimension which may allow to the treated biological structure to be within physiological conditions, e.g. the biological structure may not be overheated over critical temperature causing irreversible changes in the biological structure.

The static position of the at least one applicator may be provided by a positioning member. The positioning member may be e.g. an arm or an adjustable flexible belt. The positioning member may include a buckle for adjusting the length of the belt. The applicator may be placed within predefined locations of the belt. Alternatively the applicator may be shaped to be moveable along the positioning member, e.g. the shape of the applicator may be preferably concave, e.g. V-shaped or U-shaped. The positioning member may be inserted itself into the concavity of the applicator. The position of the applicator may be adjusted by limited movement along the positioning member because the positioning member may be used as guiding member. However, the applicator may not be fixed to a particular static position. The position of the applicator may be dynamically adjusted during the treatment following the patient's needs. The position of the applicator may be adjusted manually by the operator, or automatically by the treatment device. In one exemplary embodiment a plurality of applicators may be used for treating larger body part, e.g. buttocks, abdomen or thigh.

The applicator may include at least one sensor for detecting the temperature of the skin. The sensor may be preferably contactless. Alternatively the sensor may measure the temperature in contact manner. Alternatively, the skin impedance may be determined as well.

The plurality of applicators may be positioned with respect to each other in one plane; in at least two mutually tilted planes defined by convex or concave angles, or perpendicular to each other; or in at least two parallel planes. The angles of the planes may be adjusted by an operator following the patient's needs. In an alternative embodiment the patient may be positioned in the intersection of the magnetic fields generated by the plurality of magnetic field generating devices.

The benefit of this application may be treatment of a plurality of cooperating muscles, such as agonist and antagonists, e.g. one muscle may be stimulated to achieve strengthening effect and on the other side the other muscle may be stimulated to achieve myorelaxation effect.

Using a plurality of magnetic field generating devices provides faster treatment. Large and/or different areas may be treated in shorter time. Using a plurality of applicators allows different areas and/or target biological structures to be stimulated at the same time. The movement of the at least one applicator may automatically follow a predetermined trajectory. Hence manual manipulation is not needed. Furthermore the shape of the generated magnetic field may be adjusted by an operator.

The treatment device and/or the applicator, preferably a hand-held applicator, may include a human machine interface including inputting and/or outputting interface, e.g. graphical user interface. The outputting interface may include audio output, e.g. a speaker or beeping element; visual output, e.g. a display or color changing element; or any combination. The outputting interface may provide a notification for the operator and/or the patient in a human perceptible form such as beep, flashing light, color change or mechanical signal. Inputting interface may include at least one input element, e.g. touch member such as touchscreen, keyboard or control member for adjusting the treatment or microphone for providing the information from operator. The operator may adjust e.g. a treatment protocol or may adjust treatment parameters following the patient's needs. A communication link between the human machine interface and control unit of the treatment device may be established.

The graphical user interface may provide instruction to the patient to improve the treatment, e.g. contraction of correct muscles. The output in human perceptible form may be adjusted by the operator following the patient's needs, e.g. a plurality difficulty levels may be set.

Furthermore the applicator may include a human machine interface for providing the operator an interface for adjusting the treatment parameter, e.g. treatment protocol, magnetic flux density etc.

The magnetic stimulation device may include at least one energy source, at least one energy storage device (e.g. a capacitor), at least one magnetic field generating device (e.g. a coil) and at least one switching device. The magnetic field generating device may include a core, however in a preferred embodiment the magnetic field generating device includes no core. The switching device may be any kind of switch such as diode, MOSFET, JFET, IGBT, BJT, thyristor or a combination of them.

The at least one magnetic generating device may be in various shapes to enhance a variability of magnetic field profile. The shape of the magnetic field generating device may be circular, semicircular, rectangular, "FIG. 8", V-shape, Y shape or a butterfly shape. The magnetic field generating device may be flat (2-D shape). In an alternative embodiment the magnetic field generating device may correspond to various 3-D bodies, e.g. a hemisphere. In another alternative embodiment the magnetic field generating device may be flexible to be better fitted to the patient. The magnetic field generating device may or may not include a core for the field shaping.

Large areas may be stimulated by the plurality of the magnetic field generating devices. The plurality of magnetic field generating devices may generate a plurality of independent magnetic fields, e.g. two magnetic field generating devices may generate two magnetic fields with two peaks of magnitude of magnetic flux density.

The plurality of magnetic field generating devices may be operated at various treatment parameters and/or operation modes to provide various treatment effects for the patient during the treatment, e.g. myostimulation, myorelaxation, analgesic effect or aesthetic effects such as adipose tissue reduction, muscle toning, muscle shaping, body contouring, body shaping, skin tightening, cellulite treatment, circumferential reduction, breast enhancement and/or lip enhancement.

Figure 6A:
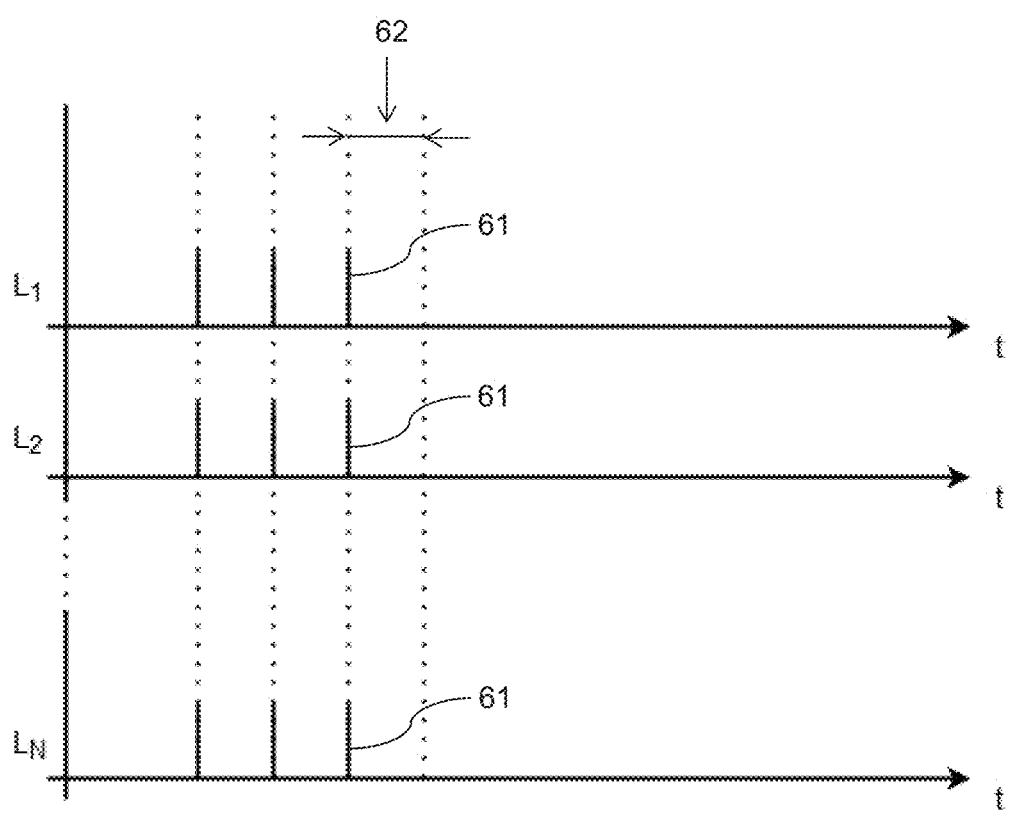
FIG. 6A illustrates an operation mode when impulses are generated by the plurality of magnetic field generating devices at one time within a pulse.
Figure 6B:
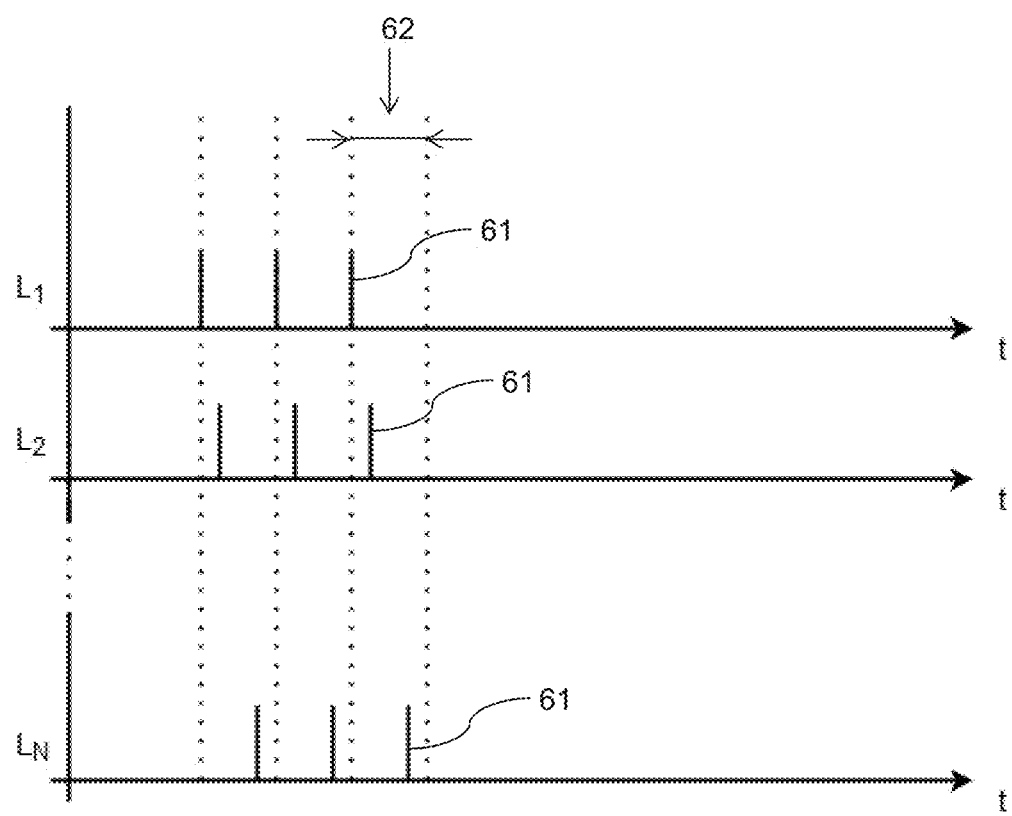
FIG. 6B illustrates an operation mode when impulses are generated by the plurality of magnetic field generating devices at plurality of different times within a pulse.

The treatment by the magnetic stimulation device may be in different operation modes. One operation mode may generate a plurality of impulses 61 at one time within the pulse 62 as illustrated in FIG. 6A. Another operation mode may generate a plurality of the impulses 61 at different times within the pulse 62 as illustrated in FIG. 6B. Both operation modes may be combined.

Figure 7:
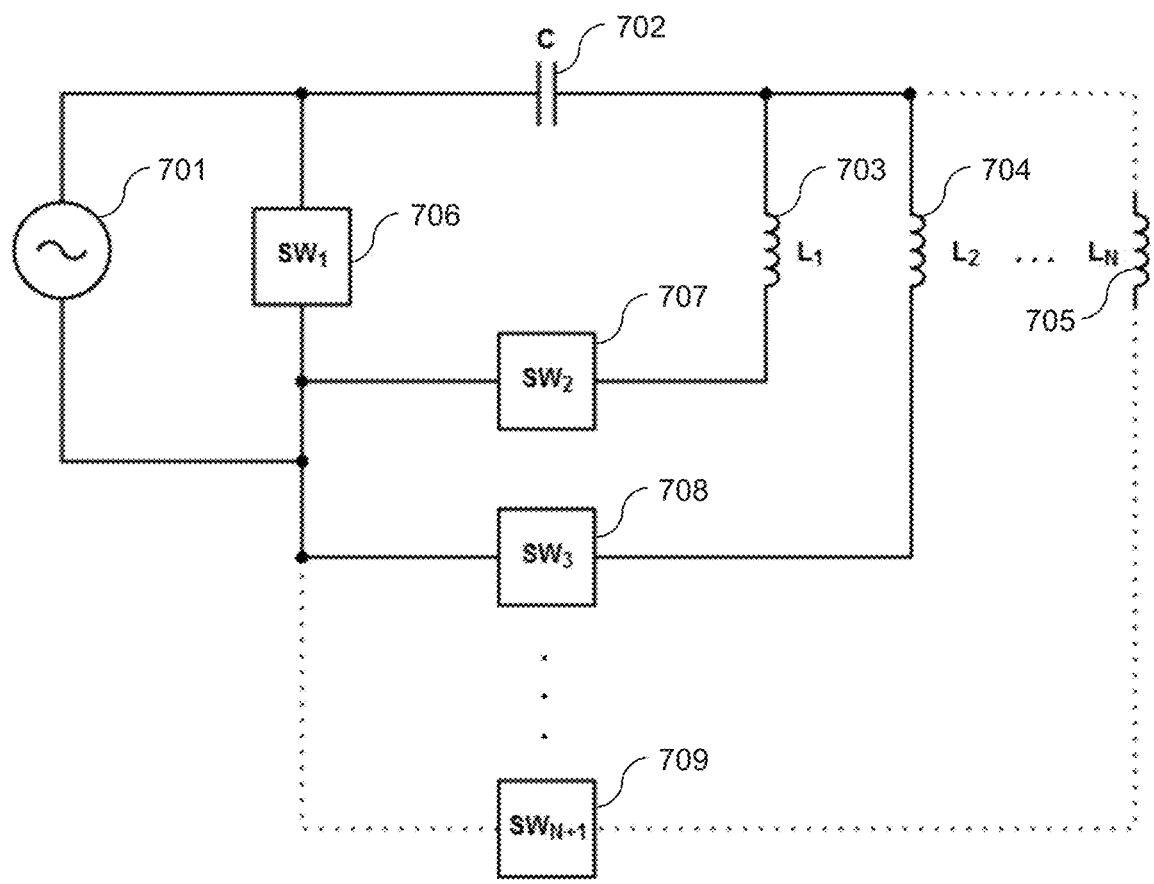
FIG. 7 illustrates an exemplary embodiment of a magnetic stimulation device including a plurality of magnetic field generating devices generating time-dependent impulses.

The magnetic stimulation device may generate a plurality of the impulses 61 by the magnetic field generation devices $L_1, L_2, \ldots L_N$ at one time within the pulse 62. This operation mode is illustrated in FIG. 6A. As shown in FIG. 7, a magnetic stimulation device may include at least one energy source 701, one energy storage device 702, N magnetic field generating devices 703-705 and N+1 switching devices 706-709, wherein N is positive integer greater than 1. This exemplary embodiment includes a minimum of hardware components. The value of inductance of each magnetic field generating device may be constant, however in an alternative embodiment different values of inductance may be used.

The switching devices 707-709 may be switched separately, with the magnetic field generated by separate magnetic field generating devices.

In an alternative embodiment any switching device may be switched in combination with at least one other switching device.

The active magnetic field generating devices are the magnetic field generating device in the closed loop of the electric circuit. For example if the number of active magnetic field generating devices is 2 and the inductances of the magnetic field generating devices are the same, then the value of magnetic flux density for each magnetic field generating device is one-half of the magnetic flux density which would be reached by one active magnetic field generating device with the same parameters and conditions, e.g. inductance, resistance, frequency, voltage. The total equivalent inductance of the magnetic stimulation device may be changed by switching a plurality of switching devices into a closed electric circuit. Therefore the impulse duration may be adjusted by adjusting the inductance. The value of total equivalent inductance (Ltotal) may be determined by Equation 4.

$$1/L_{total} = 1/L_1 + 1/L_2 + \ldots + 1/L_N$$

The magnetic stimulation device may generate a plurality of impulses 61 generated by the magnetic field generation devices $L_1, L_2, \ldots L_N$ at different times within the pulse 62. This operation mode is illustrated in FIG. 6B. This operation mode may multiply the repetition rate perceived by the patient, e.g. when the number of magnetic field generation device is 3 and the repetition rate of each magnetic field generating device is 100 Hz, then the patient may perceive the repetition rate 300 Hz. In an alternative example, this operation mode may be used for treatments of high repetition rate when the magnetic stimulation devices are switched to reach such repetition rates which may be sufficiently cooled.

Figure 8:
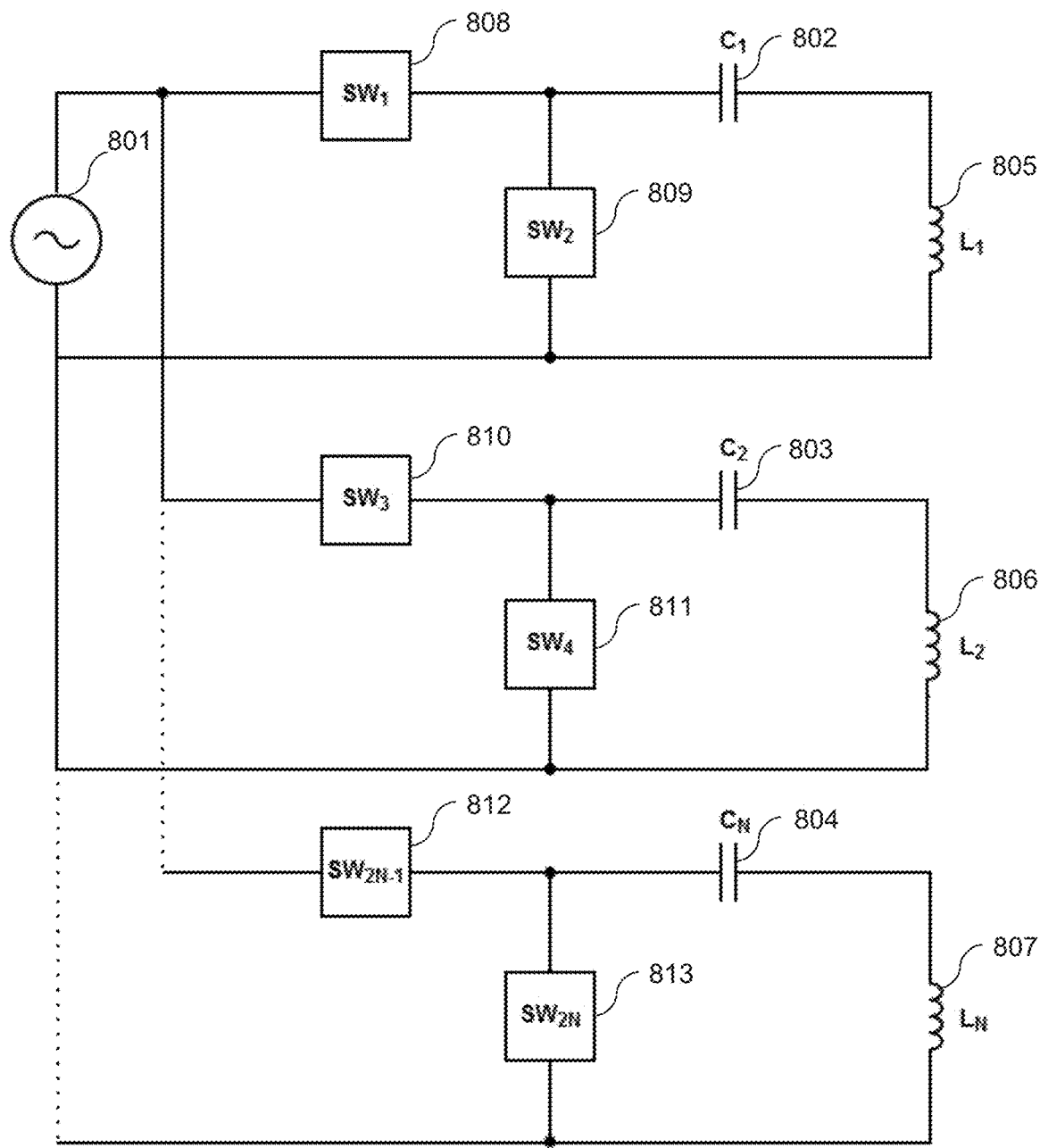
FIG. 8 illustrates an exemplary embodiment of a magnetic stimulation device including a plurality of magnetic field generating devices generating time-independent impulses.

In the example of FIG. 8 a magnetic stimulation device includes at least one energy source 801, N energy storage devices 802-804, N magnetic field generating devices 805-807 and 2×N switching devices 808-813, wherein N is positive integer greater than 1. The at least one energy storage device 802-804 may be selectively charged by the energy source 801 by selectively switching the switching devices 808, 810, 812 and the impulses may be selectively generated by selectively switching the switching devices 809, 811, 813.

The benefit of this exemplary embodiment is the time independency of the impulses generated by the separate magnetic field generating devices. However, the switching devices may be synchronized to generate the impulses at one fixed time within the pulse or both operation modes may be combined using this embodiment. Another benefit of this embodiment is the possibility of providing various treatments by a plurality of magnetic field generating devices. Various treatments may provide various effects for the patient, e.g. stimulation, such as myostimulation, pain alleviation or myorelaxation.

Figure 9:
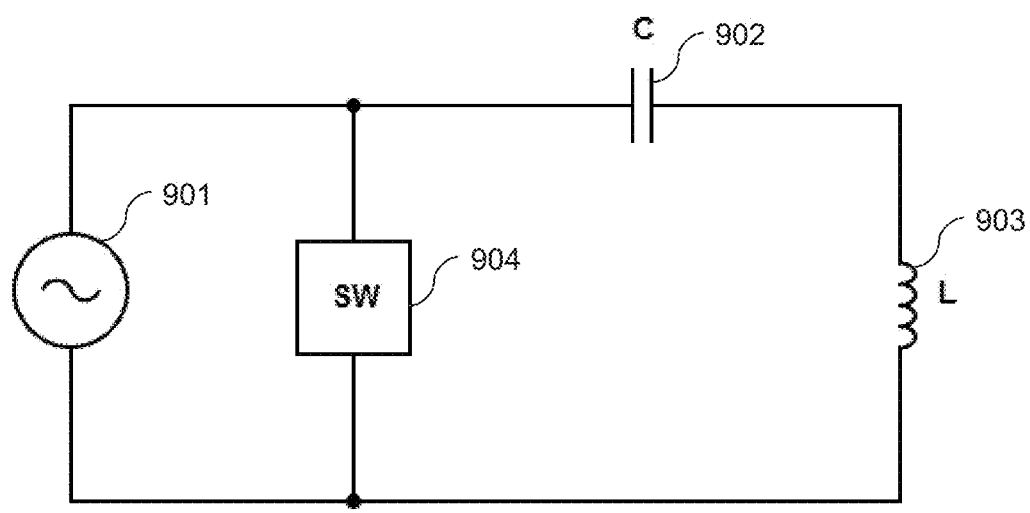
FIG. 9 illustrates an exemplary embodiment of a magnetic stimulation device including a plurality of magnetic field generating devices generating time-independent impulses.

FIG. 9 illustrates an example where the magnetic stimulation device includes N energy sources 901, N energy storage devices 902, N magnetic field generating devices 903 and N switching devices 904, wherein N is positive integer greater than 1. The at least one energy storage device 902 may be selectively charged by the energy source 901 and the impulses may be selectively generated by selectively switching the switching devices 904.

The impulses generated by the separate magnetic field generating devices are time independent. However, the switching devices may be synchronized to generate the impulses at one time within the pulse or both operation modes may be combined.

The inductance of magnetic field generating devices in each embodiment may vary. The capacitance of the energy storage devices in each embodiment may vary as well. The impulse duration may be variable and/or the magnetic flux density generated by different magnetic field generating devices may vary as well.

A magnetic treatment device may include at least one energy source and/or connection to the energy source, at least one switching device, at least one energy storage device, e.g. a capacitor, and at least one magnetic field generating device e.g. a coil.

The treatment device and/or the applicator, preferably a hand-held applicator, may include a human machine interface including inputting and/or outputting interface, e.g. graphical user interface. The outputting interface may include audio output, e.g. a speaker or beeping element; visual output, e.g. a display or color changing element; or any combination. The outputting interface may provide a notification for the operator and/or the patient in a human perceptible form such as beep, flashing light, color change or mechanical signal. Inputting interface may include at least one input element, e.g. touch member such as touchscreen, keyboard or control member for adjusting the treatment or microphone for providing the information from operator. The operator may adjust e.g. a treatment protocol or may adjust treatment parameters following the patient's needs. A communication link between the human machine interface and control unit of the treatment device may be established.

The treatment parameters may be constant during the treatment. Alternatively the treatment may vary during the treatment. The treatment may be modulated. The treatment parameters may be adjusted by the operator following the patient's needs.

Repetition rate and/or magnetic flux density may vary during the treatment protocol. Further the magnetic stimulation signal may include several periods of stimulation signal of different repetition rates, therefore the modulation of the signal is in repetition rate domain. The stimulation signal may include several periods of stimulation signal of different magnetic flux densities, therefore the modulation of the signal is in magnetic flux density domain. In yet another approach the envelope of the stimulation signal may be modulated by combinations of repetition rate domain, magnetic flux density domain or impulse duration domain.

Various envelopes of the stimulation signal and waveform, e.g. pulse, sinusoidal, rectangular, square, triangular, saw-tooth, trapezoidal, exponential etc. for the purpose of muscle stimulation may also be used, and is not limited to recited shapes of stimulation signals.

The plurality of magnetic field generating devices may be used for treating at least two cooperating muscle groups. In an exemplary application one muscle may be treated to achieve myostimulation effect and other muscle may be treated to achieve myorelaxation effect, analgesic effect may be alternatively induced. Alternatively at least two different muscles of muscle layers may be stimulated by with the same effect.

The applicator including a coil which is preferably flat for magnet therapy is placed proximate to the patient's body. The magnetic flux is applied into the biological structure. The electric current is induced and stimulates the neuromuscular plate. Due to the stimulation at least a partial muscle contraction is caused.

The applicator of magnetic stimulation signal is placed proximate to the patient's body. As used here, proximate to includes both contactless and in actual contact with the skin of the patient. The muscles are selectively stimulated by the stimulation signal and the magnetic flux density of the stimulation may be adjusted following the patient's need.

The applicator for magnet treatment is placed proximate to the patient's body. The magnetic flux density is applied into the target biological structure. Electric current is induced and stimulates the neuromuscular plate and/or the nerve innervating the at least one muscle fibre. The stimulation causes at least a partial muscle contraction.

The appropriate position may be found by firing at least two pulses, preferably at least 10 pulses, more preferably at least 50 pulses, most preferably at least 100 pulses or up to 500 pulses.

The applicator may be designed to treat large area such as entire body parts, e.g. a thigh or an abdomen. This applicator may treat shallow muscles and/or muscle groups; adipose cells; skin and/or skin surface; or it may be used in dermatology for treating dermatologic issues such as psoriasis.

Alternatively the applicator may be designed to provide a focused treatment. This applicator may be used e.g. for detecting a trigger point based on the lower magnetic flux density which induces at least partial muscle contraction. In the preferred embodiment the treatment device may include a feedback device for detecting the muscle response, e.g. by detecting induced dynamic forces caused by the at least partial muscle contraction, alternatively EMG may be used. In still another embodiment the at least partial muscle contraction may be determined visually.

The feedback information may be provided by determining an active response for stimulation, e.g. at least partial muscle contraction or change in biological structure characteristic. The at least partial muscle contraction may cause dynamic forces which may be determined by at least one sensor preferably placed beneath the patient, more preferably a plurality of sensors may be used as well. Alternatively at least one sensor may be within the applicator, e.g. for determining skin temperature or for determining the active response of the target biological structure. Following the feedback information the magnetic stimulation device may adjust the position and/or orientation of the magnetic field generating device with respect to the patient to improve the effectiveness of the treatment.

The feedback information system may use at least one contactless sensor for determining the movement caused by the at least partial muscle contraction. In exemplary embodiment the sensor may be proximity sensor e.g. capacitive or optical. Hence the feedback may be provided contactless.

Another contactless feedback information system may include a video sensor to determine the at least partial muscle contraction. The video signal may be processed by the calculation algorithm and/or method to evaluate the at least partial muscle contraction.

The information from feedback information system may be used for improving the effectiveness of the treatment via a human machine interface providing the patient with the feedback information in human perceptible form, such as audio output, e.g. a speaker or beeping element; visual output, e.g. a display, flashing light or color changing element; electric signal; mechanic signal or any combination. The video output may include a graphical processing, e.g. a game controlled via feedback information such as biofeedback application. The graphical user interface may provide instruction to the patient to improve the treatment, e.g. contraction of correct muscles. The output in human perceptible form may be adjusted by the operator following the patient's needs, e.g. a plurality difficulty levels may be set.

The applicator may be a loop-coil. The biological structure may be inserted to the area inside the loop-coil. The loop-coil applicator may provide a substantially homogenous magnetic flux density inside the coil.

The device can be used for treatment/successive treatments in continual, interrupted or various duty cycle regime. The duty cycle may be higher than 10%, which means interrupted regime with the ratio up to 1 active to 9 passive time units.

The present method stimulates the biological structure by pulsed magnetic field. The peak to peak magnetic flux density on the coil surface is at least 0.2 T, 0.4 T, 1.5 T, 2 T, or at least 3 T and with magnetic flux density up to 7 T at repetition rates exceeding 50 Hz, 100 Hz, 250 Hz, 400 Hz or 625 Hz with treatment/successive treatments lasting several seconds or longer, for example, for at least 5, 10, 30, 60, 120, or 240 seconds, or longer. The pulse width is in the range of tens to hundreds of microseconds, e.g. 200, 400, 500 or 625 µs. The duty cycle of the stimulation may be at least 1:50, more preferably at least 1:40, even more preferably at least 1:20, most preferably at least 1:8 or up to 1:4.

The pulse width is in the range of tens to hundreds of µs, preferably in the range of 100 to 600 µs, most preferably in the range of 250 to 350 µs.

Repetition rate of the magnetic impulses may reach up to 700 Hz, more preferably up to 500 Hz, most preferably in the range of 1 to 300 Hz, e.g. 5, 30, 70, 120, 140 or 180 Hz.

The impulse duration is in the range of 10 to 700 µs, more preferably in the range of 30 to 500 µs, even more preferably 50 to 250 µs, most preferably in the range of 60-90 µs.

The impulse duration may be in the range of hundreds of µs to tens of ms, 200 µs to 50 ms, more preferably in the range of 300 µs to 10 ms, most preferably in the range of 500 µs to 2 ms.

The impulse frequencies for the magnet treatment may be in the range of hundreds of Hz to hundreds of kHz, more preferably in the range of ones of kHz to tens of kHz, most preferably up to 10 kHz. However the repetition rate of the magnetic impulses may reach up to 700 Hz, more preferably up to 500 Hz, most preferably in the range of 1 to 300 Hz. The magnetic flux density of the magnet treatment is at least 0.1 T, more preferably at least 0.5 T, even more preferably at least 1 T, even more preferably at least 1.5 T, most preferably at least 2 T, or up to 7 Tesla on the coil surface.

Figure 10:
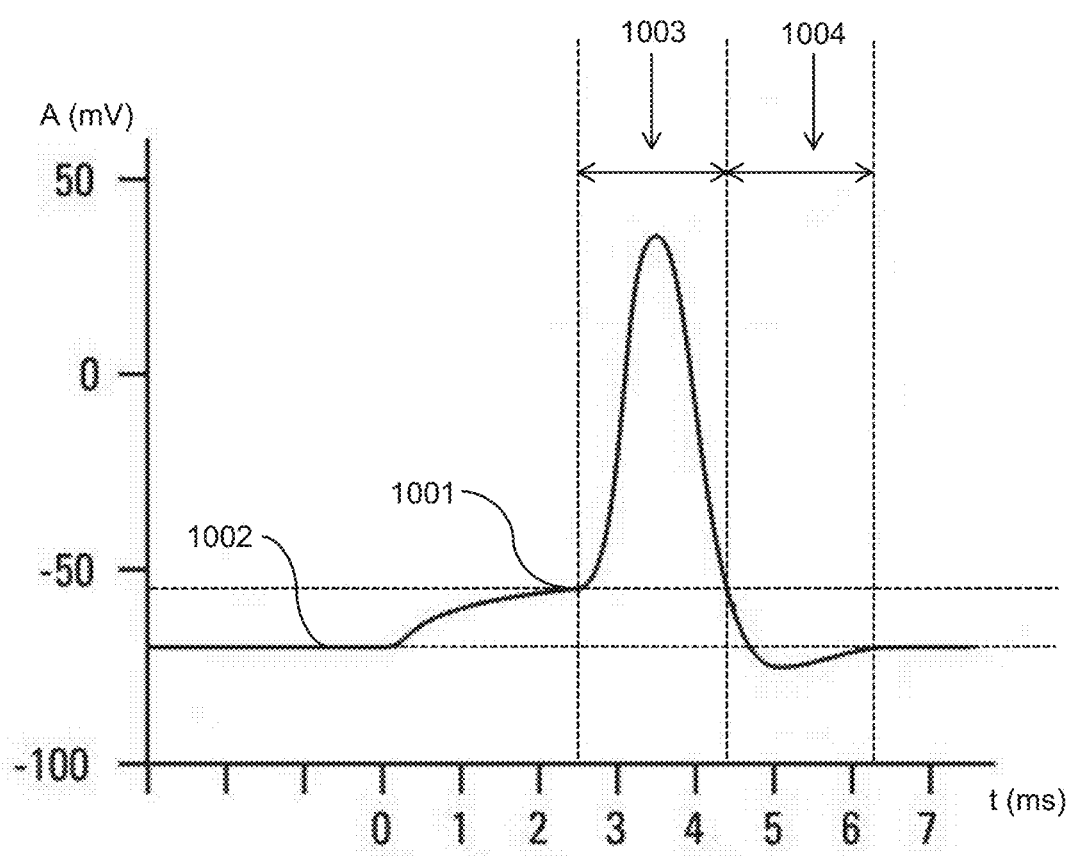
FIG. 10 illustrates a curve of action potential of a biological structure.

Referring to FIG. 10, the stimulation of the biological structure, a cell, is explained by a curve 1001 of an action potential. The action potential of the cell rapidly increases after the stimulus (induced by pulsed magnetic field) and reaches the threshold 1002—so called depolarization. After the reaching the maximal amplitude value, the membrane permeability changes and repolarization occurs. The negative value is reached in relation to resting potential 1003. Afterwards the potential recharges back to the value of resting potential 1003'. The time period from the threshold 1002 to the return of potential to the threshold 1002' (which equals threshold value 1002) is called absolute refractory period 1004. The cell is not able to be stimulated any more during the absolute refractory period 1004, even by very strong stimulus. The time period from the end of absolute refractory period 1004 to resting potential 1003' is called relative refractory period 1005. The cell is able to be stimulated only by the intensive over-threshold stimulus during the relative refractory period 1005. Over-threshold stimulus is a stimulus of higher magnetic flux density than the value of threshold stimulus. The absolute refractory period 1004 is the same time duration for all the cells, however, the relative refractory period 1005 varies following the cell type.

Figure 11:
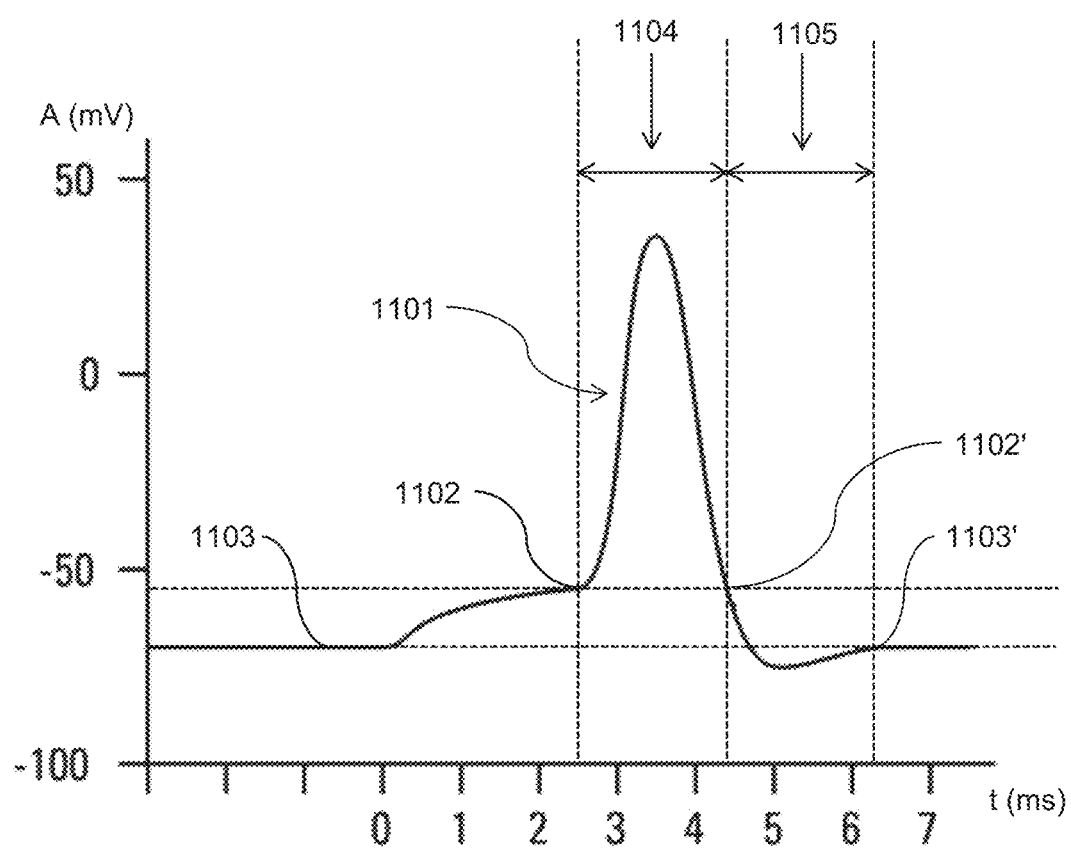
FIG. 11 illustrates a curve of action potential of a biological structure.

Referring to FIG. 11, the stimulation of the biological structure, a cell, is explained by a curve 1101 of an action potential. The action potential of the cell rapidly increases after the stimulus (induced by pulsed magnetic field) and reaches the threshold 1102—so called depolarization. After the reaching the maximal amplitude value, the membrane permeability changes and repolarization occurs. The negative value is reached in relation to resting potential 1103. Afterwards the potential recharges back to the value of resting potential 1103'. The time period from the threshold 1102 to the return of potential to the threshold 1102' (which equals threshold value 1102) is called absolute refractory period 1104. The cell is not able to be stimulated any more during the absolute refractory period 1104, even by very strong stimulus. The time period from the end of absolute refractory period 1104 to resting potential 1103' is called relative refractory period 1105. The cell is able to be stimulated only by the intensive over-threshold stimulus during the relative refractory period 1105. Over-threshold stimulus is a stimulus of higher magnetic flux density than the value of threshold stimulus. The absolute refractory period 1104 is the same time duration for all the cells, however, the relative refractory period 1105 varies following the cell type.

The present methods may be used for muscle stimulation and exercising, e.g. for treatment of pelvic floor muscles, incontinence, etc. Incontinence is a disability of mainly older patients to restrain evacuations of urine or faeces. Incontinence is currently treated by exercising pelvic floor muscles or by utilizing vaginal or rectal probes using direct current therapy, or using urologic chairs using stimulation by pulsed magnetic field. However, urologic chairs achieve low magnetic flux density at high repetition rate. Efficacy of urological chairs is low because the values of stimulation parameters, repetition rate and magnetic flux density, are insufficient. Therefore the therapy is relatively time consuming and uncomfortable for the patient.

Another field of application may be treatment of erectile dysfunction. A synergic effect may also be myorelaxation.

The present methods may be used for various stimulation of any other muscle or muscle group or any other biological structure, especially for the deep muscles, e.g. psoas major muscle, and the diaphragm. The method may stimulate other biological structures, e.g. selective stimulation of the particular muscle groups for improving their functionality or for generating a contraction pattern from the muscle group for improving the efficiency of the movement or generating the muscle memory.

According to another aspect of this invention the method may be used for magnetic field stimulation by pulsed magnetic field at repetition rates above 50 Hz, 100 Hz, 150 Hz, or 200 Hz are favourable mainly for treatment of denervated muscle. Denervated muscle lacks the ability of conscious contraction due to a lesion or nerve degradation caused by e.g. polio or trauma, so that the signals from the central neural system are not received. The muscle loses the ability of contraction and flexibility and it atrophies. Effects of muscle atrophy are visible just after three weeks of inactivity.

The stimulation of denervated muscle is based on the adaptability of health motor unit for the raising magnetic flux density. Denervated muscle lacks an ability of adaptation to raise induced electric stimulus as in a normal healthy muscle. Hence the denervated muscle is stimulated by low magnetic flux density.

Figure 12:
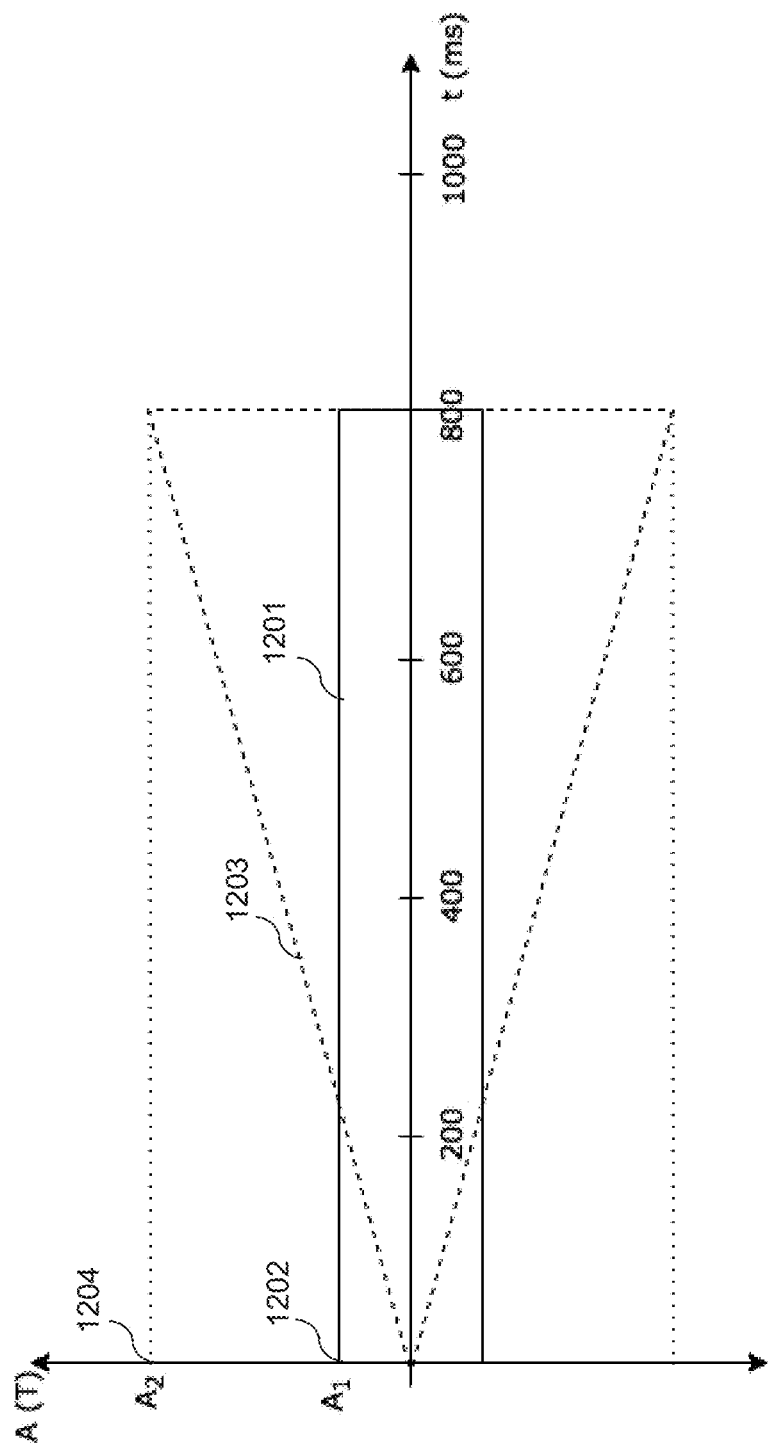
FIG. 12 illustrates a threshold value corresponding to different envelopes of the stimulation signal.

FIG. 12 illustrates the different shapes of the envelope of the stimulation signal and corresponding different threshold values of a healthy muscle. When the healthy muscle is stimulated by a rectangular envelope 1201 of stimulation signal the muscle contraction occurs at magnetic flux density $A_1$ 1202. When the healthy muscle is stimulated by increasing envelope 1203 of stimulation signal the muscle contraction occurs at magnetic flux density value $A_2$ 1204. However, when the denervated muscle is stimulated by increasing envelope 1203 of stimulation signal the denervated muscle contraction occurs at magnetic flux densities below $A_2$ 1204. Magnetic flux density value $A_2$ 1204 is a multiplication of magnetic flux density value $A_1$ 1202, wherein the multiplication coefficient is positive number greater than 1.

Figure 13A:
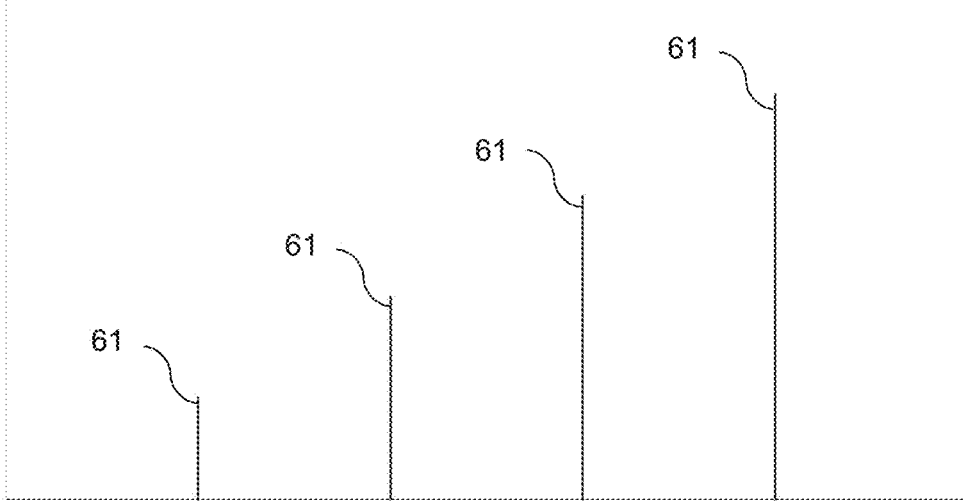
FIGS. 13a and 13b illustrate a detail of a stimulation signal with increasing envelope.

The stimulation results in an at least partial contraction of denervated muscle and the contraction of healthy muscle is eliminated or minimized. FIGS. 13-15 describes generation of various types of envelopes. The envelope may be generated on the basis that the biological structure, e.g. a nerve or at least one muscle fiber, is not able to distinct single pulses during the stimulation at higher repetition rates, e.g. exceeding 100 Hz, more preferably at least 150 Hz, even more preferably at least 200 Hz, most preferably at least 250 Hz, or up to 700 Hz. The lower value of repetition rate is limited by the time duration of the absolute refractory period. Generally, at least two pulses are necessary to create a simple shape of the envelope, e.g. rectangular or trapezoid. However, the more complex envelope shape is the more pulses are needed. The induced energy (IE) stimulating the target neural structure is a function of repetition rate, magnetic flux density and/or impulse duration. The envelope may consist of several impulses 61 called train. The number of pulses in one train varies in range of at least 2 pulses to thousands of pulses. The repetition frequency of envelope is given by the envelope period, i.e. the envelope may include time with no stimulation as well. The envelope may consist of stimulation signals with various burst frequencies, e.g. 5, 10, 20, 50, or more Hz. The envelope may be generated by several modulation approaches.

The stimulation signal may consist of several impulses 61 called burst and a time period with no stimulation. The number of pulses in one burst varies in range of at least 2 pulses to thousands of pulses. The envelope may consist of stimulation signals with various burst frequencies, e.g. 5, 10, 20, 50, or more Hz. The above defined method may be used for therapy, mainly for treatment of denervated muscle. Further the envelope may consist of several periods of stimulation signal of different repetition rates. Therefore the modulation of the signal is in repetition rate domain. In yet another approach the envelope may be modulated by combination of repetition rate domain and magnetic flux density domain.

Figure 13B:
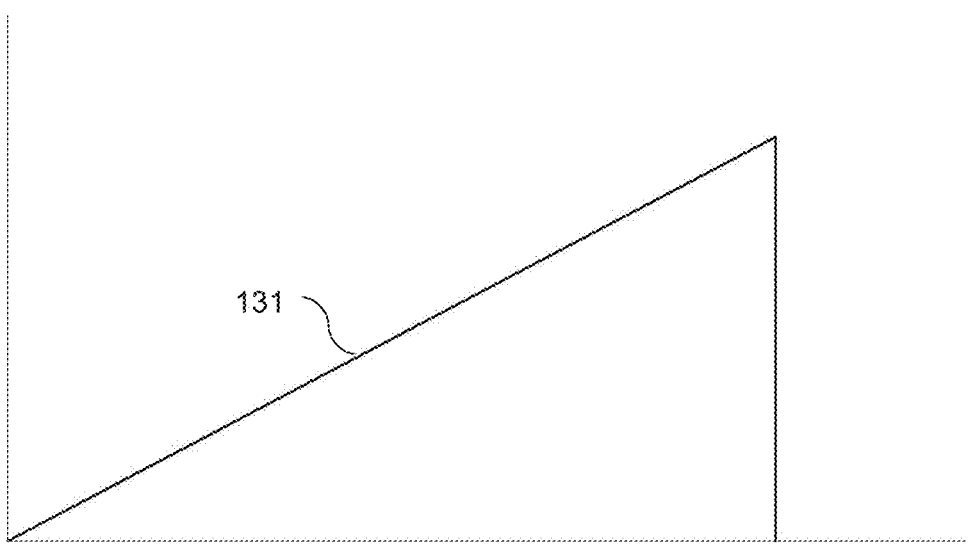
Figure 14A:
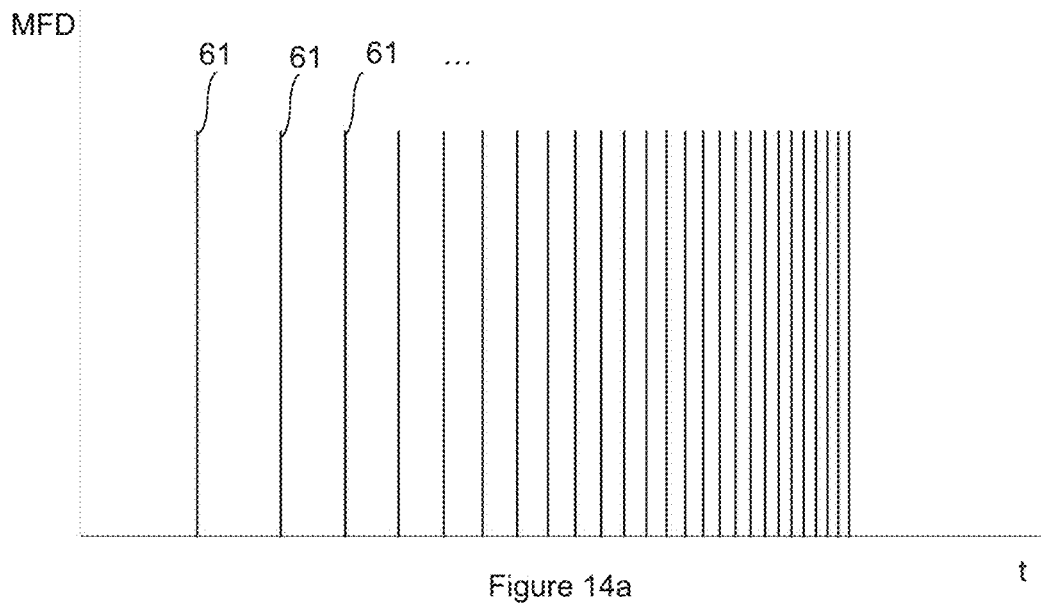
FIGS. 14a and 14b illustrate a detail of a stimulation signal with increasing envelope.
Figure 14B:
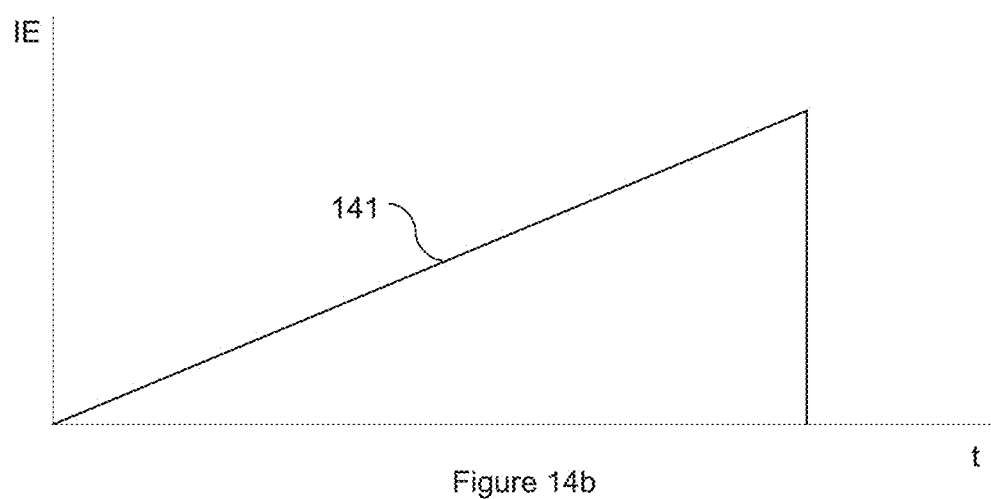

Envelope may be generated by time-varying magnetic field of varying peak magnetic flux density hence the process is called magnetic flux density modulation (MFDM). The principle of MFDM is described in FIGS. 13a and 13b. The repetition rate of the time-varying magnetic field is constant hence the period of the pulse is constant. The impulse duration remains constant as well. However, the magnetic flux density of each impulse 61 varies with respect to the preceding impulse 61, as in FIG. 13a. Therefore each impulse magnetic flux density is different from magnetic flux density of the preceding impulse. The principle is explained by triangular shaped envelope 131 as shown in FIG. 13b.

Alternatively the envelope may be generated in repetition rate domain hence the process is called repetition rate modulation (RRM). The principle of RRM is described in FIGS. 14a and 14b. The magnetic flux density of each impulse 61 remains constants. The impulse duration remains constant as well. Therefore the induced energy for one pulse is constant. However, the repetition rate varies hence the time duration of each pulse varies with respect to the preceding pulse, see FIG. 14a. The actual value of induced energy corresponds to the actual repetition rate of the time-varying magnetic field. When the repetition rate increases the value of induced energy increases or vice versa. The principle is explained by triangular shaped envelope 141, see FIG. 14b.

Figure 15A:
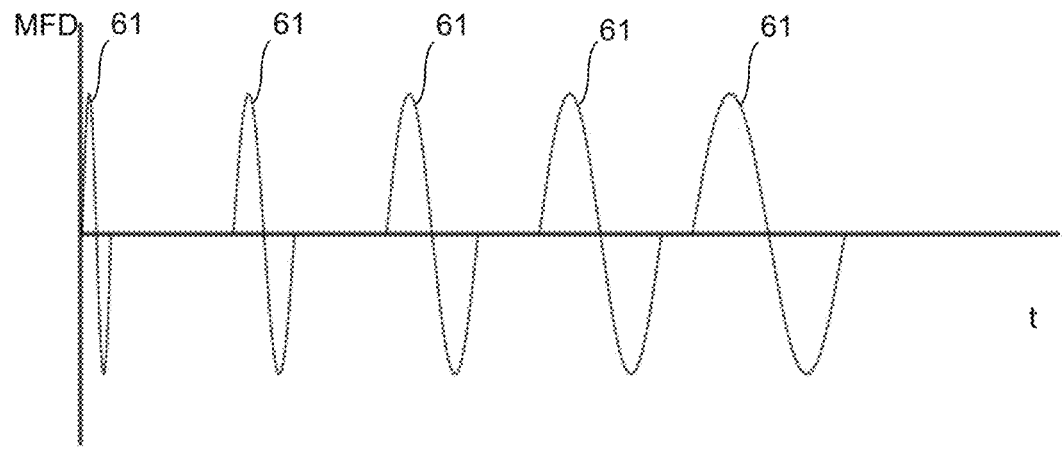
FIGS. 15a and 15b illustrate a detail of a stimulation signal with increasing envelope.
Figure 15B:
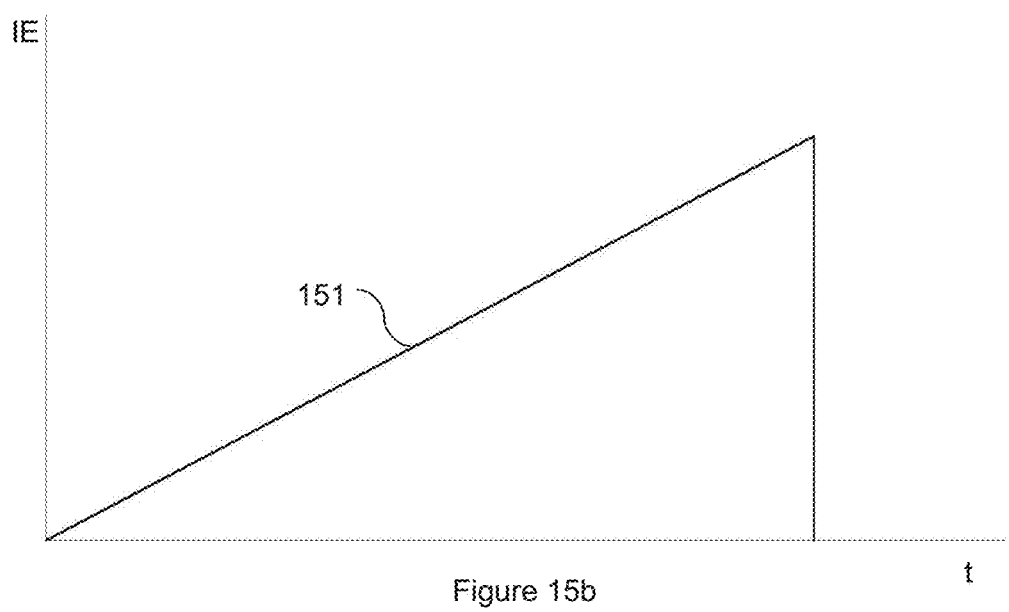

According to still another aspect of the application, envelope may be generated in impulse duration domain. The principle of impulse duration modulation is shown in FIGS. 15a and 15b where the magnetic flux density and the repetition rate of time-varying magnetic field remains constant. However, the impulse 61 duration of each pulse varies as shown FIG. 15a. The principle is explained by triangular shaped envelope 151 in FIG. 15b.

The modulation approaches are not limited by exemplary waveform. Therefore the envelope may be rectangular, square, saw-tooth, trapezoidal, sinusoidal, exponential etc. Person skilled in the art of neurology and/or physiotherapy may modulate various envelopes and/or envelopes combination.

The application is not limited to use the only single modulation approach. In the preferred application any combination of the upper mentioned approaches may be used.

In an alternative application the neural structure may be stimulated by rectangular or increasing shaped envelope as well.

According to another aspect of the application in neural system diagnostics, the neural structure may be stimulated by single pulses or rectangular shaped envelope, and by increasing shaped envelope. Both envelopes are used for determination of minimal magnetic flux density value sufficient to induce at least partial muscle contraction. The envelope duration may last 1 second. After the determination of both magnetic flux densities values, the level of muscle denervation may be calculated.

An essential principle of magnet therapy used for biological structure stimulation is the influence of the magnetic field on the cell. The cell membrane is polarized due to the induced electric current. One of fundamental phenomenon of electric current in biological tissue may be an action potential occurrence, a transfer of neural excitation and/or a partial or full muscle contraction may be induced. Additionally, the effect of the generated action potential may modulate a painful stimulus transmission, providing a pain management effect.

According to still another application of the invention, the neural structure stimulation by time-varying magnetic field may be used for pain management. In general, the method is focused on neural structure stimulation by time-varying magnetic field of repetition rate at least 100 Hz and/or magnetic flux density sufficient to induce and/or modulate an action potential in a stimulated neural structure.

According to one approach of the aspect of the application in pain management, the neural structure may be stimulated by an envelope created by higher repetition values e.g. exceeding 100 Hz, more preferably at least 150 Hz, even more preferably at least 200 Hz, most preferably at least 250 Hz, or up to 700 Hz. The envelope may be generated with predefined repetition frequency and/or shape.

According to another aspect of the application in pain management, the neural structure may be stimulated by time-varying magnetic field at repetition rate in the range of 80 to 120 Hz, more preferably 90 to 110 Hz, even more preferably 95 to 105 Hz, most preferably around 100 Hz, with magnetic flux density inducing at least below-sensory-threshold stimulus or more preferably at least sensory-threshold stimulus following the application and indication. The method may stimulate the large diameter neural fibers. In general, time-varying magnetic field of repetition rate around 100 Hz with magnetic flux density inducing at least sensory-threshold stimulus is used preferably for pain relief effect.

According to another approach of the aspect of the application in pain management, the neural structure may be stimulated by a time-varying magnetic field to induce electric current of random repetition rate fluctuation around a predefined repetition rate. In the preferred application the repetition rate fluctuates at least 5%, more preferably at least 15%, most preferably at least 30% or up to 50%, the magnetic flux density is sufficient to induce at least sensory-threshold stimulus, more preferably at least over-sensory-threshold stimulus of the neural structure. The neural structure is not able to adapt for the stimulation by time-varying magnetic field since the repetition rate varies. Additionally, the magnetic flux density may be adjusted during the time.

According to still another aspect of the application in pain management, the neural structure may be stimulated by time-varying magnetic field for alleviating the pain via spinal cord and/or spinal nerve stimulation. The aspect of the application may be based on the pattern theory of pain perception. The time-varying magnetic field may be delivered to the target area of backbone and/or spine. Specifically, the method exploits benefits and pain alleviating effect of stimulation with repetition rate at least 125 Hz, more preferably at least 135 Hz, most preferably around 145 Hz or up to 170 Hz. The magnetic flux density is sufficient to induce at least motor-threshold stimulus, more preferably below-noxious-threshold stimulus. Additionally, during the application at least partial muscle contraction may occur hence the local perfusion may increase. Still another benefit of the presented aspect may be myorelaxative effect, long lasting analgesic effect which may be used e.g. for alleviating pain after injuries, in orthopaedics, rheumatology, migraine, headache, neck pain, lumbago, pain of upper or lower extremities and improving the perfusion of itself. Furthermore, various pain syndromes may be treated by the present method.

According to still another aspect of the application in pain management, the neural structure may be stimulated by time-varying magnetic field at repetition rate of at least 160 Hz, more preferably at least 170 Hz, most preferably around 180 Hz, or up to 250 Hz. The present method may be based on gate-control theory of pain. In the preferred application the impulse duration lasts 500 µs at repetition rate around 180 Hz. Optimal magnetic flux density is sufficient to induce at least motor-threshold stimulus, more preferably below-noxious-threshold stimulus. The magnetic flux density may be adjusted following the patient's needs based on the sensitivity of a patient and the depth of the stimulated neural structure. However, the minimal magnetic flux density exceeds 0.1 T, more preferably 0.5 T, even more preferably 1 T, most preferably up to 7 T to induce the at least one action potential. Benefit of the present method is myorelaxative effect. According to one approach of the aspect of the application in myorelaxation, the neural structure may be stimulated by time-varying magnetic field at repetition rate in the range of 30 to 150 Hz, more preferably in the range of 50 to 100 Hz. The time-varying magnetic field is preferably modulated to prevent the neural structure to adapt the magnetic stimulation. The magnetic flux density is sufficient to induce at least over-sensory-threshold stimulus, more preferably motor-threshold, even more preferably over-motor-threshold stimulus According to still another approach of the aspect of the application in pain management, the neural structure may be stimulated by trains 1601 of several pulses 1602 and time with no stimulation after the train 1601. The group of several pulses 1601 and the time with no stimulation is called burst 1604. Therefore one burst 1604 consists of the only one train 1601 and time with no stimulation 1603. The train 1601 preferably consists of at least 2 pulses, more preferably 5 pulses, even more preferably tens pulses or up to hundreds pulses; repetition rate of the pulses 1602 is at least 100 Hz. The burst repetition rate may vary following the patient's needs. In the preferred application the burst repetition rate vary from 1 to 10 Hz. The number of pulses 1602 in train 1601 and/or the time with no stimulation may vary following the patient needs.

Figure 16:
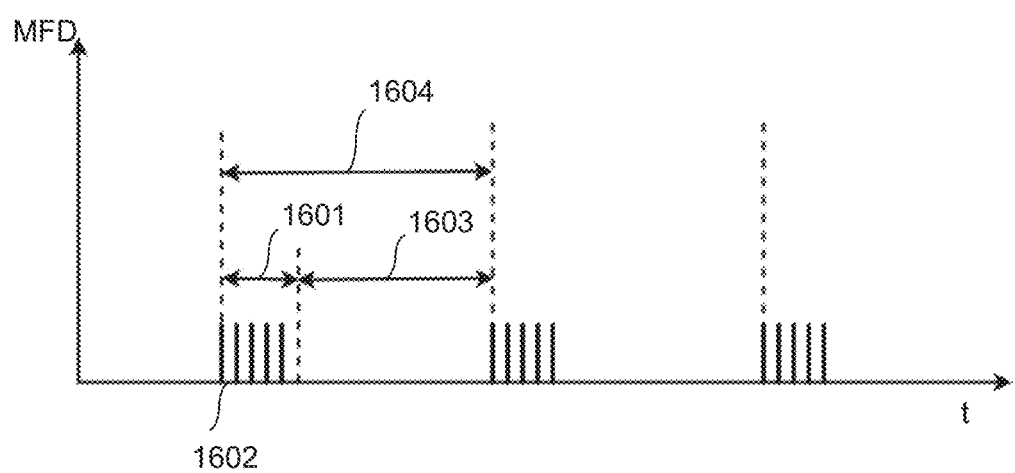
FIG. 16 illustrated a stimulation by exemplary clusters.

FIG. 16 shows an example of application of the stimulation by time-varying magnetic field with a repetition rate of 125 Hz in clusters 1601 consisting of 5 pulses 1602, with a burst 1604 repetition rate 10 Hz. Total time duration of one burst is 100 ms. Total stimulation time of one cluster 1601 is 40 ms, hence the time with no stimulation 1603 is 60 ms. The most important advantage of this approach is analgesic effect and almost no adaptation of the neural structure to the stimulation. The approach may be used e.g. for alleviating the acute pain.

Magnetic stimulation at high repetition rates according to proposed invention is further applicable for the effect of myorelaxation. The repetition rate of at least 100 Hz, 110 Hz, 120 Hz, or 130 Hz may be used for the purpose of the muscle stimulation.

One of the myorelaxation approaches is non-paralyzed muscle adaptation to high repetition rate of stimuli. The magnetic flux density is sufficient to induce current in the biological structure causing motoric intensity or over-motoric intensity at the beginning of the application and it becomes below-motoric intensity after several minutes at constant magnetic flux density since the non-paralyzed muscle can accommodate for the stimulus of constant repetition rate. The impulse time duration is in at least tens of µs, more preferably at least 250 µs or 500 µs. The time duration of a pulse is at least 1 ms, 2.5 ms or 5.5 ms. A repetition rate of pulses around 180 Hz is highly effective. A temporary reflex adjustment of hypertonic muscles or muscle groups is achieved by the application of magnetic stimulation thereafter myorelaxation is provided.

Further application of magnet therapeutic method using sufficient magnetic flux density at high repetition rates over 100 Hz is focused especially on spastic muscle and its trigger point. The method proposes stimulation of muscle hypertonia of the overloaded muscle fibres to relieve a local spasm (the hypertonia in stimulated muscle fibre is relieved). The method affects the muscle insertion as well. The method may even affect the whole muscle group for specific movement.

The stimulation by pulsed magnetic field is divided into two separate periods. The neuromuscular plate is stimulated by pulsed magnetic field during the first period. The magnetic flux density is sufficient to induce at least motoric intensity of electric current to cause at least partial muscle contraction in the stimulated biological structure. The muscle is activated by isometric contraction and sedation follows. The most reactive fibres are selectively inhibited. During the second period the repetition rate is increased to at least 100 Hz, 150 Hz, or 200 Hz. The muscle is relaxed due to high repletion rate. The method is used for high-quality relaxation of at least one muscle fibre.

The method may be used also in sport medicine for stretching of athletes before a performance and muscle relaxation after the performance, thereafter it significantly contributes to muscle regeneration. Further applications are treating for muscle imbalance or muscle relaxation caused by overload, pain relief or elimination and preparation the muscle for physical activity.

The present method may also be used for functional joint blockade treatment. A joint may include muscular structure providing the movement of the joint, joint itself including synovial fluid. Functional joint blockade may be caused by spastic muscles in the vicinity of the joint whose secondary effect is pain. The most common functional joint blockades are in the backbone. These can cause vertebrogenic problems, headache and backbone pain, migraine, perfusion ailment resulting to dizziness, backbone sharp pain directing to limbs, visual insufficiency, tinnitus, toothache or earache etc. The scoliosis, sacral pain (even after fractures), weakness of pelvic floor muscles and incontinence, urine retention or constipation or functional sterility may also be treated by treatment of functional joint blockade.

For the purpose of functional blockade treatment and joint movability improvement the preferred repetition rates may be at least 50 Hz, 60 Hz, 70 Hz or 100 Hz, magnetic flux density at least 0.2 T, 0.4 T, 0.5 T, or at least 1 T and up to 7 T.

Formerly the functional joint blockades were treated by manual positioning, traction, mobilization of the soft tissues, reflex therapy or even pharmacologically. The present method achieves at least partial muscle contraction in the vicinity of the joint, e.g. backbone, by stimulation of neuromuscular plate by pulsed magnetic field at low repetition rate and high magnetic flux density providing at least partial muscle contraction. The joint contact surfaces are moved and the joint is moved due to at least partial muscle contractions of muscles in the vicinity of the joint, e.g. the muscles in the vicinity of the backbone are represented by rotators which causes local microrotations of the backbone. The functional joint blockade is unblocked via muscle mobilization by mechanical approach.

Still another approach of the present method is affecting the rheological properties of synovial fluid by pulsed magnetic field. The total effect of this method may be synergic. Although the method is explained on example of backbone functional joint blockade, the application of the method is not limited to the backbone. A person skilled in anatomy or physical therapy is able to apply the method for any other joint provided by sufficient amount of neuromuscular structures in vicinity. The present method may be preferably used in combination with analgesic methods. It is very convenient to use the present method in combination with method providing myorelaxation since the functional joint blockade is caused by spastic biological structures in vicinity.

All the described methods of stimulation provide trophotropic, anti-oedematous or placebo effect which contributes to the patient's health state and comfort. Local metabolism may be increased as well.

The values of magnetic flux density and repetition rate are cited in several preferred applications since the perception of the stimulation is subjective. Nevertheless the magnetic flux density and repetition rates are not limited by the recited values. A person skilled in physical therapy is able to repeat and apply the therapy methods adjusting the magnetic flux density or repetition rate following the patient's needs.

A person skilled in the physical therapy is able to use various envelopes of the stimulation signal and waveform, e.g. pulse, sinusoidal, rectangular, square, triangular, sawtooth, trapezoidal, exponential etc. for the purpose of muscle stimulation. The invention is not limited to recited shapes of stimulation signals.

Stimulation signal of biological structure by pulsed magnetic field following the recited methods may be but not limited to continuous, pulsed, randomized, burst. The pulse may be but not limited to symmetric, asymmetric, most preferably biphasic. As used here, proximate to includes in actual contact with the skin of the patient.

In the methods described above, the patient is seated on a patient supporting means maintaining the patient in sufficiently seated position such as a chair or the patient is in sufficiently horizontal position such as supine, prone or lateral position on suitable patient supporting means, e.g. a treatment table or a bed. One or more applicators providing the magnetic stimulation are positioned adjacent to the patient, or in contact with the patient's skin. Generally, the patient's head, torso and limbs are unrestricted, i.e. the patient is free to move and no part of the patient is secured, e.g. strapped, to the patient supporting means. The applicator or applicators are generally placed near the patient, but may not be attached to the patient, so that no part of the treatment apparatus, i.e. one or more applicators and the patient supporting means is attached to the patient and does not restrain or guide a movement of any part of the patient. The magnetic stimulation typically does not cause the patient to move continuously, although some movement may occur via muscle contraction, during certain treatments.

The methods described above do not involve exertion or voluntary contraction of muscle. Rather, the patient is idle and in a relaxed state. In some applications the methods may be used to treat any healthy tissue, and the methods may be used with only magnetic stimulation alone, without any other form of stimulation.

As used here muscle means a single muscle or a group of muscles. Actively moving means physically moving any part of the patient via external apparatus exerting physical force on the patient.

The present method is not limited to be used independently. For enhancing the result the method may be used in combination with other conventional non-invasive and/or invasive aesthetic medicine method.

Skin is composed of three basic elements: epidermis, dermis and hypodermis or so called subcutis. The outer and also the thinnest layer of skin is the epidermis. The dermis consists of collagen, elastic tissue and reticular fibers. The hypodermis is the lowest layer of the skin and contains hair follicle roots, lymphatic vessels, collagen tissue, nerves and also fat forming a subcutaneous white adipose tissue (SWAT). The adipose cells create lobules which are bounded by connective tissue, fibrous septae (retinaculum cutis).

Another part of adipose tissue, so called visceral fat, is located in the peritoneal cavity and forms visceral white adipose tissue (VWAT) located between parietal peritoneum and visceral peritoneum, closely below muscle fibers adjoining the hypodermis layer.

A method of treating a biological structure uses a combination of non-invasive methods for enhancing human appearance. The invention utilizes electromagnetic radiation. Methods may be used for targeted remodeling adipose tissue, focused treatment of cellulite, body contouring, skin tightening or skin rejuvenation. The invention relates to focused heating of the target tissue by electromagnetic waves, whereas the effect of focused heating of the target tissue is amplified by the effect of a pulsed magnetic field treatment.

The present invention discloses the advanced approaches in aesthetic applications, e.g. for cellulite treatment and/or body shaping. Combined methods of treatment by electromagnetic field and treatment by magnetic field are used. The electromagnetic field may include treatment by radiofrequency, infrared or optical waves. The magnet treatment may be provided by permanent magnets, electromagnetic devices generating a static magnetic field or time-varying magnetic devices. In the preferred application the treatment by a pulsed magnetic field and radiofrequency treatment may be combined. However the application is not limited by the recited combination so the combined method may include magnet treatment and any treatment by electromagnetic field, e.g. light treatment, IR treatment or treatment by radiofrequency waves, e.g. microwaves, short waves or long waves.

The energy source for the magnetic and/or light treatment device may be preferably external, e.g. a plug. Alternatively the energy source may be incorporated in the device, e.g. a battery.

Magnet treatment in combination with radiofrequency treatment may be represented by two independent treatment devices, e.g. one treating the target structure by radiofrequency waves and the second treating the target structure by magnetic field. Both devices may have a separate applicator for treating the target structure, or one applicator may be used by at least two devices, i.e. the applicator may be modular for a plurality of devices.

The aesthetic treatment device may include at least one HF frequency generator for providing energy for radiofrequency treatment and for providing energy for magnet treatment. In an alternative embodiment, the device may include at least one HF frequency generator for providing energy for radiofrequency treatment and at least one other independent frequency generator for providing energy for magnet treatment. The device may include plurality of applicators for providing separate radiofrequency or magnet treatments to the patient.

In alternative embodiment the applicator may provide a combination of radiofrequency and magnet treatment. In one embodiment, the applicator may include at least one radiofrequency electrode for providing radiofrequency treatment and at least one coil for providing magnet treatment. In another embodiment, the applicator may include at least one electrode for providing radiofrequency treatment and at least one coil providing magnet treatment, wherein the at least one RF source provides energy for both at least one electrode and at least one coil.

In still another embodiment the at least one RF source may provide the energy for the at least one coil providing magnet treatment wherein the at least one coil may be used as the at least one electrode. The essence is the far different stimulation frequencies which are used for RF treatment and magnet treatment. The coil in the high frequency field is similar to the electrode. This enables the coil to be the electrode for radiofrequency treatment. In the preferred embodiment a flat coil may be used as the electrode.

The frequencies for the radiofrequency treatment may be in the range of ones of MHz to hundreds of GHz, more preferably in the range of 13 MHz to 3 GHz, most preferably around 13.56 or 40.68 or 27.12 MHz or 2.45 GHz. The term "around" should be interpreted as in the range of 5% of the recited value.

Alternatively the RF treatment may be in the range of hundreds kHz to ones MHz, more preferably in the range of 250 kHz to 1 MHz, even more preferably in the range of 400 to 600 kHz, most preferably in the range of 450 to 550 kHz. Such a RF treatment may provide a heating of the target biological structure, e.g. at least one muscle fiber, muscle or a tendon, to provide relaxation effect.

The combination of the recited method may improve currently used applications in various aspects and the effect of the treatments may be significantly enhanced. The application of a radiofrequency electromagnetic field is combined with application of a magnetic field applied before, simultaneously or after the radiofrequency treatment. The magnetic field may be generated by a permanent magnet or electromagnet. The magnetic field may be constant in time or in the preferred application the magnetic field may be time-varying, more preferably a pulsed magnetic field may be used. The application of a magnetic field induces many benefits for radiofrequency treatment, such as applications inducing at least partial muscle contraction, myorelaxation effect or analgesic effect. The perfusion or metabolism may be improved as well.

The at least partial muscle contraction may induce enhanced effects on adipose tissue reduction by catabolism of the adipose tissue and burning energy from adipose tissue. The total adipose tissue reduction effect is enhanced by radiofrequency treatment.

Additionally, the at least partial muscle contraction may improve a blood flow and/or perfusion in the treated area. The improved blood flow may be caused by activation of muscle pump and/or by the muscle necessity of more oxygen due to the at least partial contraction. Due to increased blood flow and/or local perfusion, the risk of overheated muscle is limited or even eliminated. Further the homogeneity of the thermal field induced by thermal effect of radiofrequency treatment may be significantly enhanced and/or the temperatures may be well-balanced/compensated in the target treatment area. Still another benefit is prevention of creation any hot spot caused by steep thermal gradient.

Further the at least partial muscle contraction may improve the movement of lymphatic vessel and the lymph flow may be improved.

Due to improved blood flow, perfusion and/or lymph flow the metabolism may be improved. Additionally, the effect of radiofrequency treatment may be enhanced by improved metabolism, e.g. cellulite treatment, body shaping and/or contouring, skin tightening or skin rejuvenation. Further benefit may be reducing or eliminating the risk of panniculitis or local skin inflammation since any clustering of the treated adipocytes may be prevented by the improved metabolism. The improved blood and/or lymph flow may contribute the removing of the adipocytes. The removing of the adipocytes may be promoted by higher number of cells phagocytosing the adipocytes as well. Synergic effects of magnet and RF treatment significantly improves metabolism. Therefore the possibility of adverse event occurrence is limited and treatment results induced by the present invention are reached in shorter time period.

In the preferred application the RF and/or magnetic field may be modulated. In the most preferred application both stimulation signals are modulated. The magnetic stimulation may be modulated in the magnetic flux density domain, repetition rate domain, or impulse duration domain, to provide different treatment effects and to prevent adaptation of the target biological structure. The radiofrequency treatment may be modulated in the frequency domain, intensity domain and/or time domain to reach the most complexity and/or efficiency of the target treated biological structure. The modulation in the time domain may be changing the active and passive periods of stimulation, e.g. the radiofrequency treatment may include period with no stimulation, i.e. the radiofrequency treatment is not continual but the treatment is provided in pulses. The periods of no stimulation may vary and may be adjusted by the operator. Due to modulation during the treatment, different target biological structures may be treated in the different depth.

The application may be contact or the preferred application of the invention the treatment may be applied contactless. Contactless application may avoid all biocompatibility factors which may occur during contact treatment. In the most preferred application the treatment may be provided by self-operated device. Hence the continual surveillance and/or control by the operator is not essential for correct and/or safe operation of the treatment device. Self-operated treatment may be provided by a hand-held applicator or the applicator may be fixed to stand-alone device. The self-operated treatment may be also enabled using various types of sensors in communication with the device for monitoring the treatment and/or the patient. The at least one sensor may be e.g. reactive sensor, electrochemical sensor, biosensor, biochemical sensor, temperature sensor, sorption sensor, pH sensor, voltage sensor, sensor for measuring distance of applicator from the patient surface and/or from the treated area, position sensor, motion detector, photo sensor, camera, sound detector, current sensor, sensor for measuring of specific human/animal tissue and/or any suitable sensors measuring biological parameters and/or combination thereof such as sensor for measuring dermal tensile forces, sensor for measuring the activity of the muscle, muscle contraction forces, tissue impedance or skin elasticity.

Further the homogeneity of the treatment may be improved by several approaches. A first approach may be represented by a moveable applicator providing the dynamic treatment to a larger target area. The dynamic treatment improves the homogeneity of applied treatment energy and additionally due to larger area the effect is uniform and/or well balanced. Static positioning of the applicator may be used as well. Another approach of improving homogeneity may be represented by using a bolus. The bolus may provide improved transmittance of the electromagnetic energy to the treated biological structures. Additionally, the bolus may prevent occurrence of hot spots within the treated area; the bolus may provide constant temperature to the target treated surface area; or the bolus may increase the homogeneity of the radiofrequency waves application by providing a homogenous medium for electromagnetic waves propagation not being influenced by the interface of the target treated area and an air. The bolus may profile the electromagnetic field to enhance the effect of the treatment. In still another approach an air gap may be between the applicator and the patient.

The treatment by magnetic and/or electromagnetic field may be in continuous or discrete modes. In one application the magnetic treatment may be applied in continual mode with no pauses and the electromagnetic treatment may be applied in pulsed mode to provide improved adipose tissue reduction caused by natural process and by the increased temperature. In another application the electromagnetic treatment may be applied continuously with no pauses and the magnetic treatment may be applied in pulsed mode to provide improved thermal reduction of adipose tissue and by improved metabolism due to improved blood flow. Both modes may be combined in various treatment sequences.

In the preferred application the treatment is started at the moment when the target biological structure reaches the predetermined temperature. The temperature in the target tissue may be up to 80° C., more preferably in the range of 37 to 60° C., even more preferably in the range of 40 to 45° C. The temperature may be adjusted based on the intended use, e.g. adipose tissue reduction, collagen production or muscle contraction. In an alternative application the intended use may be coagulation and/or ablation. The temperature in the target biological structure may be measured by invasive method, e.g. using an invasive probe; or by contact method, e.g. using thermocouple sensor; or by contactless method, e.g. using infrared sensor or camera. The temperature of the target biological structure may be determined by a mathematic method. The sensor for measuring the temperature in the target biological structure may be attached to the applicator.

A benefit of the application of magnet treatment and electromagnetic treatment may be causing an analgesic effect of the application and providing a possibility of treating a patient with higher sensitivity for thermal effects induced by electromagnetic treatment, i.e. patients with any predisposition inducing increased thermal sensitivity. The analgesic effect may be induced by magnet treatment by suitable repetition rates and it may be induced immediately during the magnet treatment. The analgesic effect may last up to several hours after magnet treatment. The magnetic flux density of the magnetic stimulation may preferably reach at least motor-threshold intensity inducing at least partial muscle contraction therefore the homogeneity of the thermal field is significantly enhanced.

In one aspect of the invention, the treatment by magnetic field may be applied to the target structure before the radiofrequency treatment to prepare the target structure for following treatment by radiofrequency field. The effect of magnet treatment is to induce at least partial muscle contraction or to stimulate a muscle structure to increase a muscular tonus of the target structure. Both effects may provide a massage effect for the structure within the proximity of the target structure hence the blood and/or lymph circulation may be improved to promote local metabolism. The temperature may be locally increased by the improved blood flow and the target structure may accept the following radiofrequency treatment at significantly higher quality. Additionally, the collagen and/or elastin fibers may be remodeled or restored and/or its neogenesis may be improved to provide a younger, smoother and enhanced skin appearance.

Additionally, previous application may improve acceptability of the electromagnetic field by increasing the temperature of the skin and the transmittance of the electromagnetic field may be improved due to less value of skin impedance. Further the radiofrequency may penetrate deeper target structures relative to treatment without a preceding magnet treatment of the target structure and/or area.

Another benefit may be releasing the adipose tissue in the muscle by muscle contraction and/or by temperature increase causing better liquidity of adipose tissue. Still another benefit of the at least partial muscle contraction may be mechanical breaking large adipose tissue bulks into smaller bulks which may be easier metabolism of the adipose tissue and/or the smaller adipose tissue bulks may be removed faster by the lymphatic and/or blood flow. Due to improved metabolism and/or circulation the cellulite may be treated in a short time and the visual effect on skin appearance may be significantly enhanced.

In another aspect of the invention, the treatment by magnetic field may be applied to the target structure simultaneously with the radiofrequency treatment to improve effects of the electromagnetic treatment inducing heat in the target structure.

The simultaneous application of magnet treatment and radiofrequency treatment may be in two modes: a first mode may generate the magnet impulses while radiofrequency treatment is active or another mode may generate radiofrequency treatment while the magnet treatment is not in an active stimulation period, i.e. the period of magnet treatment and radiofrequency treatment alternates. Both modes amplify the resulting effect of the treatment. Therefore the results are achieved in significantly shorter time than the same results achieved by separate applications of the radio frequency and magnet treatments.

The simultaneous method of magnet treatment and radiofrequency treatment of the target tissue may increase the peak magnetic component of the entire treatment resulting in improved heating of the target structure including containing higher water volume, e.g. skin. Due to increased temperature of skin, the production and/or remodeling of collagen and/or elastin fibers may be improved and the skin may be provided with a younger, smoother and enhanced appearance. The effect of overheating the muscle is reduced by the improved blood flow.

In still another aspect of the invention, the treatment by magnetic field may be applied to the target structure after the treatment by electromagnetic field to enhance and/or contribute to the effects of radiofrequency treatment by influencing the target structure by magnetic field.

The magnetic field may treat the target structure to cause at least partial muscle contraction proximate to the target structure to improve blood flow and provide homogenous temperature distribution at high quality after creating a temperature distribution at lower quality by radiofrequency treatment.

The present device and methods of its operation are related to treatment of a patient by magnetic and/or electromagnetic treatment. The electromagnetic treatment may be particularly radiofrequency treatment. The application of the magnetic and/or electromagnetic treatment may be provided by at least one energy delivery element. The device may be used for treatment or focused remodeling of subcutaneous tissue by reducing number and/or value of lipid-rich cells, cellulite treatment, body shaping and/or contouring, muscle toning, skin tightening, collagen treatment, skin rejuvenation, wrinkle removing, reducing stretchmarks, breast lifting, lip enhancement, treatment of vascular or pigmented lesions of the skin or hair removing.

The essential principle for this device is a fact that the energy delivery element, e.g. a magnetic field generating device such as a flat coil which may be preferably circular shaped, may administer the same function as an electrode if it is provided by the high-frequency signal. Hence the coil may be used to generate a radiofrequency treatment. The reason is that the frequency spectra of low-frequency signal used for generating the magnetic field is far different from frequency spectra of high-frequency signal used for generating the electromagnetic field. The signals from at least one or more preferably two generators may be provided successively, with some overlay or simultaneously due to difference of the frequency spectra. The frequency spectra of high-frequency signal used for generating the electromagnetic field may be in the range of ones of kHz to hundreds of GHz, more preferably in the range of 500 kHz to 3 GHz, most preferably above 1 MHz around 3.4 or 6.7 or 13.56 or 40.68 or 27.12 MHz or 434 MHz or 915 MHz or 2.45 GHz. The frequency spectra of low-frequency signal used for generating the magnetic field impulses may be in the range of 1 to 100 kHz, more preferably in the range of 1.25 to 10 kHz, even more preferably in the range of 2 to 5 kHz, most preferably in the range of 3 to 4 kHz. The low-frequency signal is used for generating impulses of time-varying magnetic field. The repetition rate of the pulses may reach up to 700 Hz, more preferably up to 500 Hz, most preferably in the range of 1 to 300 Hz. The magnetic flux density of the magnet treatment is at least 0.1 T, more preferably at least 0.5 T, even more preferably at least 1 T, even more preferably at least 1.5 T, most preferably at least 2 T, or up to 7 T on the surface of the energy delivery element. The energy delivery element may be integrated within an applicator, such as patient support for maintaining the patient in sufficiently sitting or recumbent position, e.g. a chair or a bed. The energy delivery element may be moveable within the patient support. Alternatively the applicator may be moveable, e.g. it may be attached to an articulated arm or it may be preferably hand-held.

Figure 17:
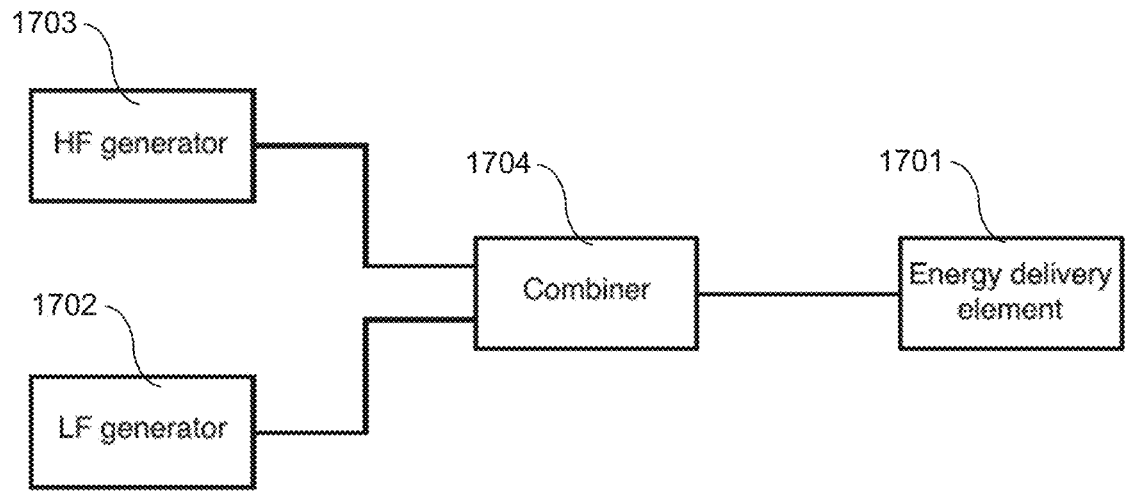
FIG. 17 illustrates a general principle of a treatment device.

FIG. 17 illustrates a general design of a treatment device. The treatment device may include at least one energy delivery element 1701, e.g. a coil, preferably a flat coil; a low-frequency generator 1702 for generating a signal for generating a magnetic field by the energy delivery element 1701. The low-frequency generator may be a connection of a switching device and an energy storage device. The switching device may be in serial connection with the energy storage device, preferably a parallel connection may be used. The treatment device further includes at least one high-frequency generator 1703 for generating a signal for generating an electromagnetic field. According to alternative embodiment only one generator providing low and high frequency may be used. Additionally a combiner 1704 for transmitting the signals to the energy delivery element 1701 may optionally but not necessarily be used. The combiner 1704 may transmit the signals from generators 1702, 1703 to the energy delivery element 1701. Furthermore the combiner may protect the high-frequency generator 1703 from the signal generated by the low-frequency generator 1702 or vice versa. Hence the combiner may prevent the signal from low-frequency generator to affect the high-frequency generator. The combiner may include at least one filtering device, e.g. capacitive and/or inductive coupling, high-pass, low-pass, band-pass or band-stop such as notch filter; at least one switching device, e.g. a switch, a diode, MOSFET, JFET, IGBT, BJT or a thyristor; or any combination thereof. Alternatively the combiner may include a relay. In an exemplary embodiment the combiner 1704 may include at least one coil and/or at least one capacitor, preferably a plurality of coils and/or a plurality of capacitors may be used as well.

The side of the energy delivery element closer to the patient may be covered by a layer of insulating material such as ceramic or epoxy coating, or bolus. The insulating material may provide electrical insulation of the patient and mechanical protection of the energy delivery element.

In an alternative embodiment the treatment device may include a plurality of HF generators and/or a plurality of LF generators.

In an alternative embodiment the treatment device may include a human machine interface for the patient. The patient may control the power in the treatment hence the patient may control e.g. temperature of the target biological structure or strength of the at least partial muscle contraction. Furthermore the patient may interrupt the treatment before any discomfort feeling may occur.

Figure 18:
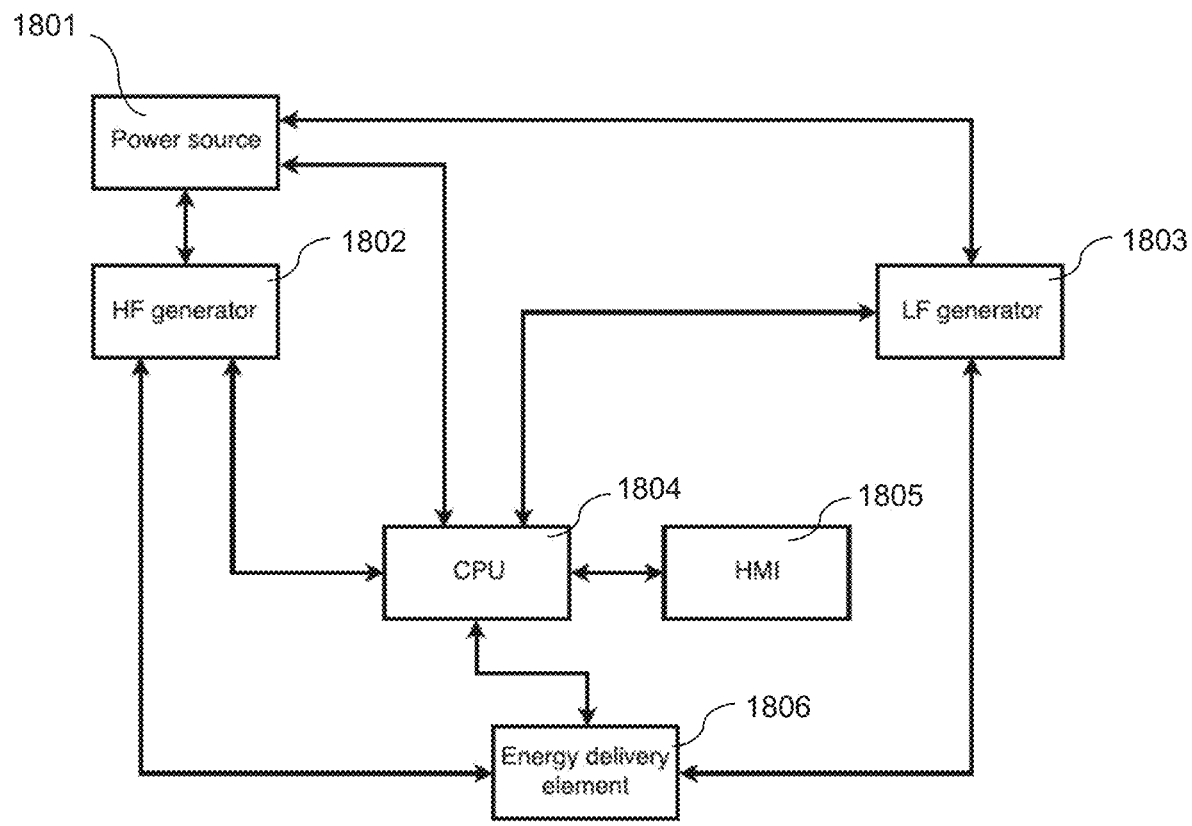
FIG. 18 illustrates a block diagram of treatment device including one energy delivery element.

FIG. 18 illustrates the treatment device which may include a connection to a power supply, a power source 1801, high-frequency generator 1802, low-frequency generator 1803, control unit 1804, human machine interface 1805 and at least one energy delivery element 1806. According to alternative embodiment only one generator providing low and high frequency may be used. The arrows illustrate the direction of communication.

The power supply may provide energy for the treatment device via the power source 1801. The power supply may be external, e.g. a plug, or it may be integrally included within the treatment device, e.g. a battery. The power source 1801 may communicate with generators 1802, 1803. The power source 1801 may provide energy to electric components of the treatment device, particularly to generators 1802, 1803 or to control unit 1804. The power source 1801 may communicate with control unit 1804 which may provide information about power necessary for the treatment. The power source 1801 may adjust the power for generators 1802, 1803 following the information from control unit 1804 or alternatively based on direct information from generator 1802 or generator 1803.

The control unit 1804 may communicate with LF generator. LF generator may provide LF signal to energy delivery element 1806 to generate magnetic treatment. The LF generator 1803 may provide information referred to treatment process to the control unit 1804, e.g. energy loss from one impulse. In an exemplary embodiment the control unit 1804 may send instruction to power source 1801 to provide the LF generator 1803 by the energy amount equaling the energy loss. Alternatively the control unit 8 may control recharge of the LF generator.

The energy delivery element 1806 may include at least one sensor, e.g. a temperature sensor. The energy delivery element may provide information to control unit 1804, HF generator 1802 and/or to LF generator 1803.

The control unit 1804 may communicate with HF generator 1802 to provide instructions for HF generator 1802. HF generator may provide HF signal for energy delivery element 1806 to generate RF treatment. The HF generator 1802 may provide information referred to treatment process to the control unit 1804, e.g. temperature of the energy delivery element 1806. In one exemplary embodiment RF energy transfer may be optimized prior to the treatment. In an exemplary embodiment the HF generator 1802 may include an internal power source for adjusting energy for energy delivery element 1806. Alternatively, more than one energy delivery element 1806 may be used. When using two or more energy delivery elements, the at least one energy delivery element may deliver magnetic field, the at least one energy delivery element may deliver electromagnetic field (e.g. radiofrequency field); in still another embodiment each energy delivery element may provide both magnetic field and electromagnetic field (e.g. radiofrequency field) for magnetic and electromagnetic treatment.

The control unit 1804 may be in communication with human machine interface 1805. The human machine interface 1805 may include outputting interface for providing information for the operator and/or the patient. The outputting interface may include audio output, e.g. a speaker; visual output, e.g. a display or any combination. The outputting interface may provide a notification for the operator and/or the patient in a human perceptible form such as beep, flashing light, color change or mechanical signal.

The human machine interface 1805 may include at least one input element, e.g. touch member such as touchscreen, keyboard, control member for adjusting the treatment, for providing the information from operator. The operator may adjust e.g. a treatment protocol or may adjust treatment parameters following the patient's need.

In an alternative embodiment the treatment device may include at least two control units. One control unit may administer HF generator. Second control unit may administer LF generator. In this exemplary embodiment a communication link between both control units may be established.

Figure 19A:
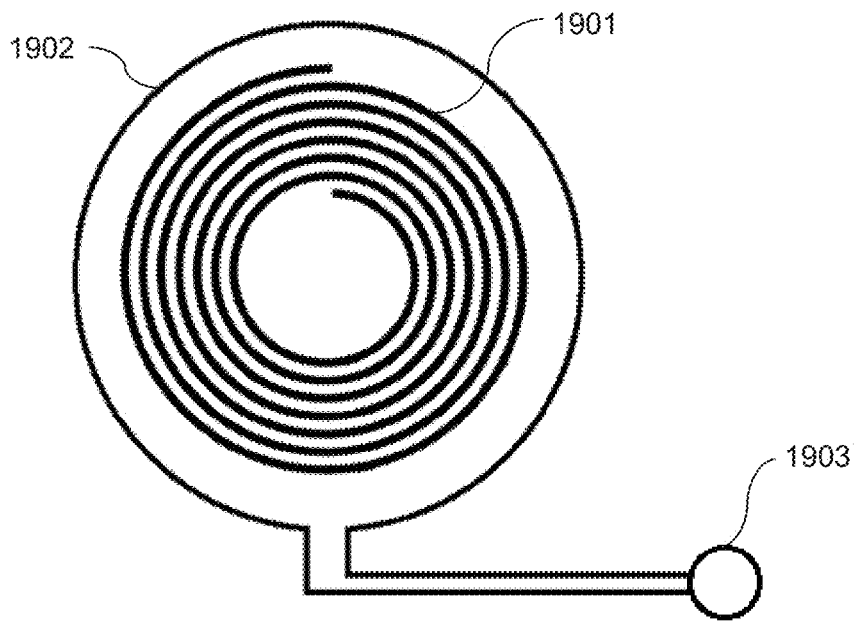
FIGS. 19a and 19b illustrate an energy delivery element used as a power supply for at least one electric component.
Figure 19B:
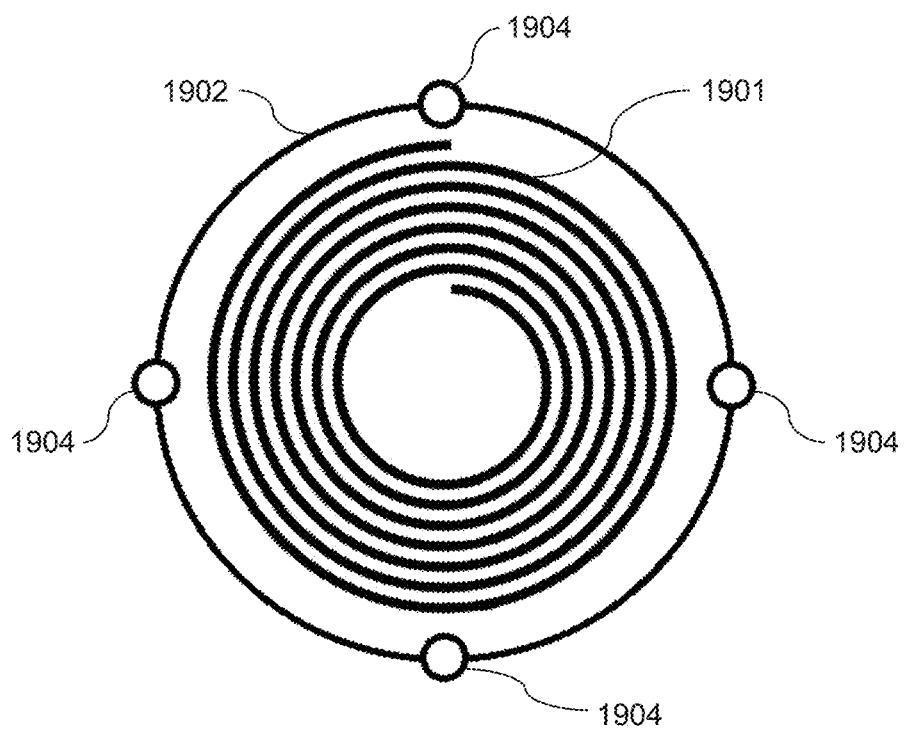

The energy delivery element may be used as an energy source for another part and/or electric member of the treatment device. The energy delivery element may be used as a part of transformer or antenna. In an exemplary embodiment illustrated in FIG. 19a the energy delivery element 1901 may be surrounded by a loop of conductor 1902 for inducing a voltage for proving power for the other electric member 1903. The loop may induce the voltage in order of tens Volts, e.g. 50 V. The induced voltage may be used for powering of electric member, e.g. a cooling device such as fan, blower or pump used for moving a cooling media, or Peltier cooler; or any electric member providing an additional treatment such as LED. FIG. 19b illustrates an exemplary embodiment of using induced voltage for powering a plurality of light sources providing optical treatment. The energy delivery element 1901 may be encircled by a loop of conductor 1902 for inducing a voltage to provide energy for the plurality of LED 1904 providing optical treatment for the patient. Alternatively at least one LED may be used for generating a light from visible spectra to be used for targeting the treatment. The power loss of the coil may be up to ones of Watts, more preferably up to 5 W, most preferably around 1 W.

Figure 20:
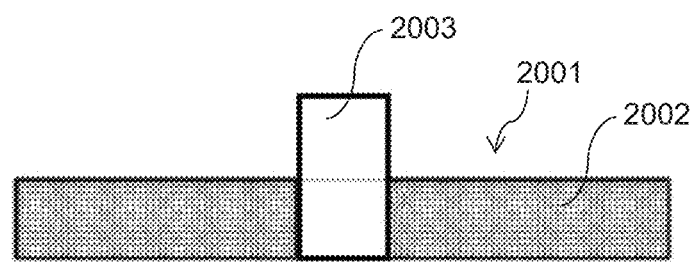
FIG. 20 illustrates an energy delivery element including a magnetic core.

FIG. 20 illustrates a cross section of an exemplary embodiment of energy delivery element 2001, particularly a flat coil comprising a plurality of insulated wires 2002. The coil may be wound around a magnetic core 2003 which may be protruded out from the coil up to several centimeters, more preferably in the range of 0.1 to 10 cm, even more preferably in the range of 0.5 to 7 cm, most preferably in the range of 1 to 5 cm. In an alternative embodiment the magnetic core may be around the coil. The magnetic field may be profiled, saturated and/or delivered to closer proximity of the patient by the protruding magnetic core.

In an exemplary embodiment the treatment device may include one energy delivery element. The energy delivery element, e.g. a flat coil, may be used for providing magnetic treatment and RF treatment. The energy delivery element may be provided by high-frequency and by low-frequency signal. The RF treatment may be unipolar. The high-frequency electromagnetic field may be radiated to the target biological structure. The applicator may be moveable to increase the homogeneity of the treatment. The scanning movement may be preferably used. Alternatively the movement of the applicator may follow a predetermined pattern corresponding to a treated body part. The movement of the applicator may be manual and/or automatically provided by a manipulating device, e.g. robotic arm or scanning mechanism.

The radiofrequency treatment may be applied by the energy delivery element to the target biological structure in three modes. One mode may be simultaneous application of RF treatment and magnetic treatment. Another mode may be separate RF treatment and magnetic treatment, RF and/or magnetic treatment may be applied in various sequences or it may alternate. Still another mode may be application of RF and magnetic treatment with some overlay. In an exemplary application the RF treatment may be applied prior a magnetic treatment. In another exemplary application the RF treatment may be applied after magnetic treatment.

In an alternative embodiment the treatment device may include a reference electrode to provide a monopolar application of RF treatment by the energy delivery element.

Figure 21A:
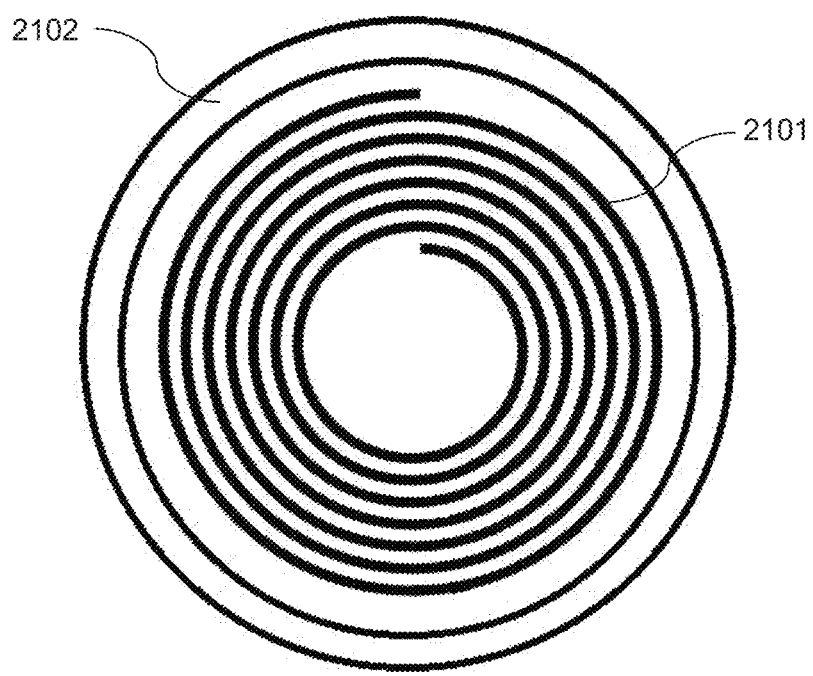
FIGS. 21a and 21b illustrate an energy delivery element encircled by at least one electrode.
Figure 21B:
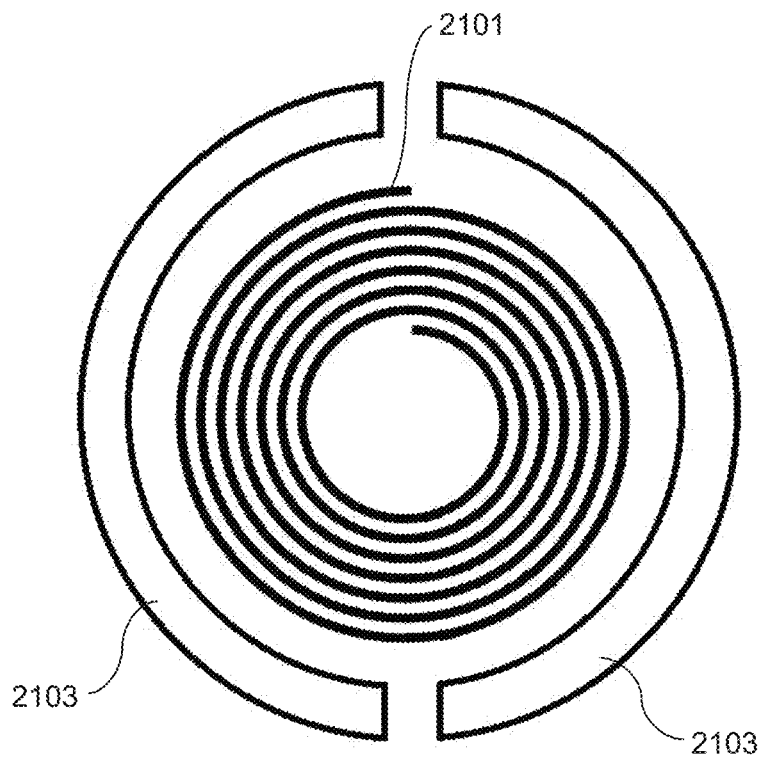

FIG. 21a illustrates an exemplary embodiment of the magnetic field generating device 2101 powered by LF generator which is encircled by an electrode 2102 for providing RF treatment. In an alternative embodiment illustrated in FIG. 21b the magnetic field generating device 2101 powered by LF generator may be encircled by a plurality of electrodes 2103 powered by HF generator to provide RF treatment. In this particular exemplary embodiment two electrodes are semicircular shaped. Still another exemplary embodiment including the magnetic field generating device powered by LF generator encircled by a plurality of round-shaped electrodes powered by at least one HF generator to provide RF treatment. Alternatively the plurality of electrodes may be powered by a plurality of HF generators. These exemplary embodiments may exclude combiner. The separation of the HF and LF signals may be provided by mechanical layout of the energy delivery elements, e.g. magnetic field generating device or electrode.

The treatment may be provided by contactless application. Alternatively the treatment may be administered in contact way or by indirect contact way by using a bolus/spacing object. The spacing object may be preferably transparent for high power magnetic field and it may include inner space filled with at least one substance. The spacing object may provide optimal distribution RF field used for treatment it may provide a cooling of the skin which it contacts.

Figure 22A:
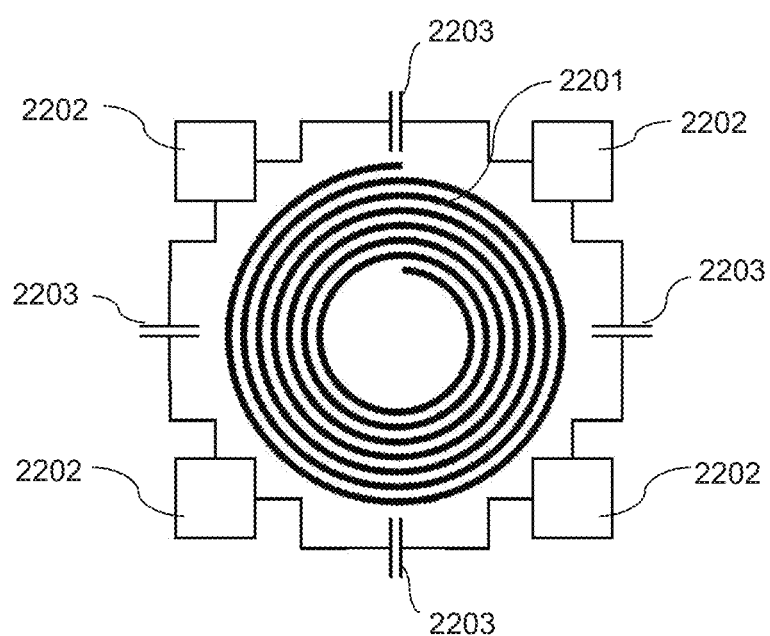
FIGS. 22a and 22b illustrate exemplary embodiments connected by coil or capacitor.

The at least two electrodes may be connected by at least one capacitor which may provide a capacitive connection between the electrodes. FIG. 22a illustrates an exemplary embodiment of the magnetic field generating device 49 powered by LF generator. The magnetic field generating device 2201 may be encircled by a plurality of electrodes 2202 which are powered by one HF generator. The electrodes may be of various shapes, e.g. angular such as square or rectangle; or round such as circular or oval. The plurality of electrodes 2202 may be connected by a plurality of capacitors 2203. The at least one capacitor provides a capacitive coupling between electrodes hence the plurality of electrodes may provide a treatment as a plurality of unipolar electrodes. On the other hand the electrodes may not be influenced by a magnetic field generated by magnetic field generating device.

Figure 22B:
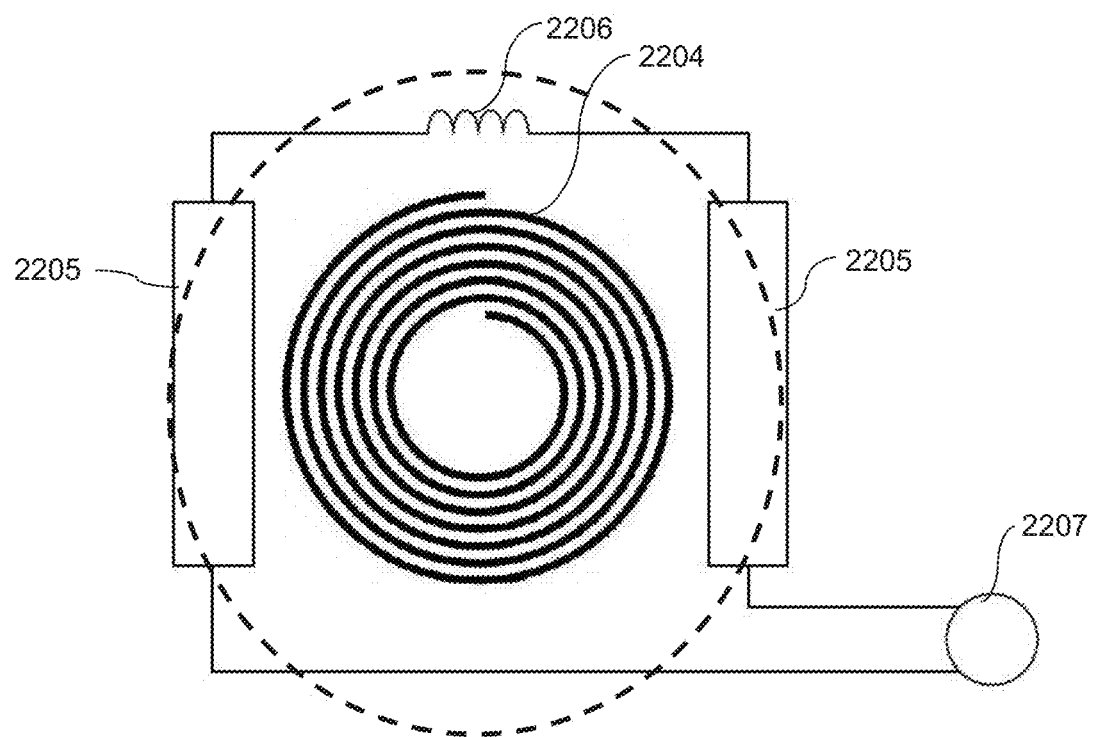

The at least two electrodes may be connected by at least one inductive member, e.g. a coil. FIG. 22b illustrates an exemplary embodiment of the magnetic field generating device 2204 powered by LF generator which is encircled by two electrodes 2205 which are powered by one HF generator. The electrodes 2205 may be connected by a coil 2206 which may provide separation of the electrodes 2205 powered by HF generator hence the RF treatment may be bipolar. On the other hand the coil 2206 provides connection of the electrodes 2205 for magnetic field generated by magnetic field generating device 2204 hence the coil and the electrodes 2205 may cause the same effect as a conductor loop (dotted line) around the magnetic field generating device 2204. The voltage induced in the loop may be use for powering of electric member 2207 as mentioned above.

Figure 23A:
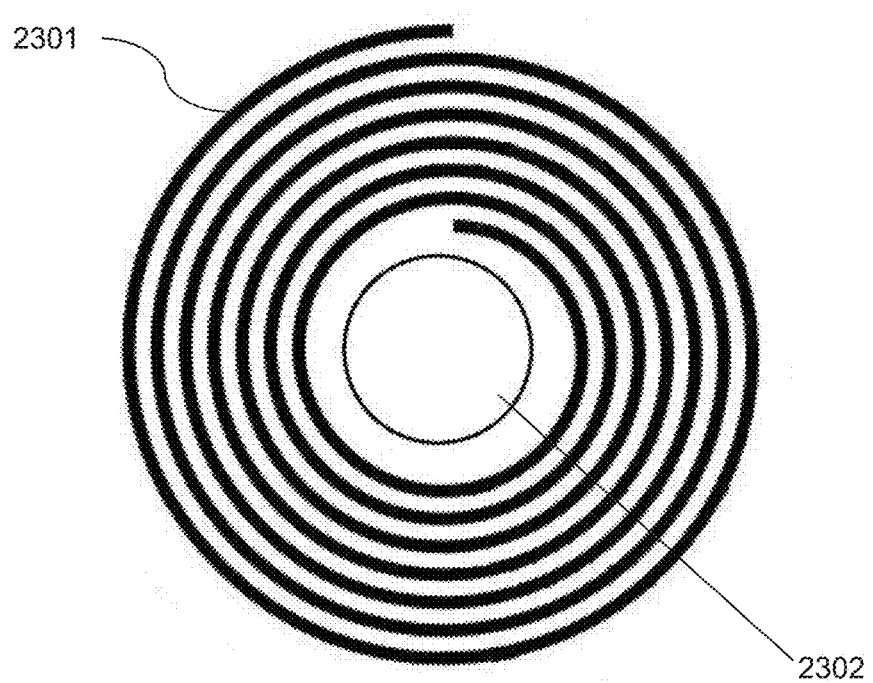
FIGS. 23a and 23b illustrate at least one electrode encircled by an energy delivery element.
Figure 23B:
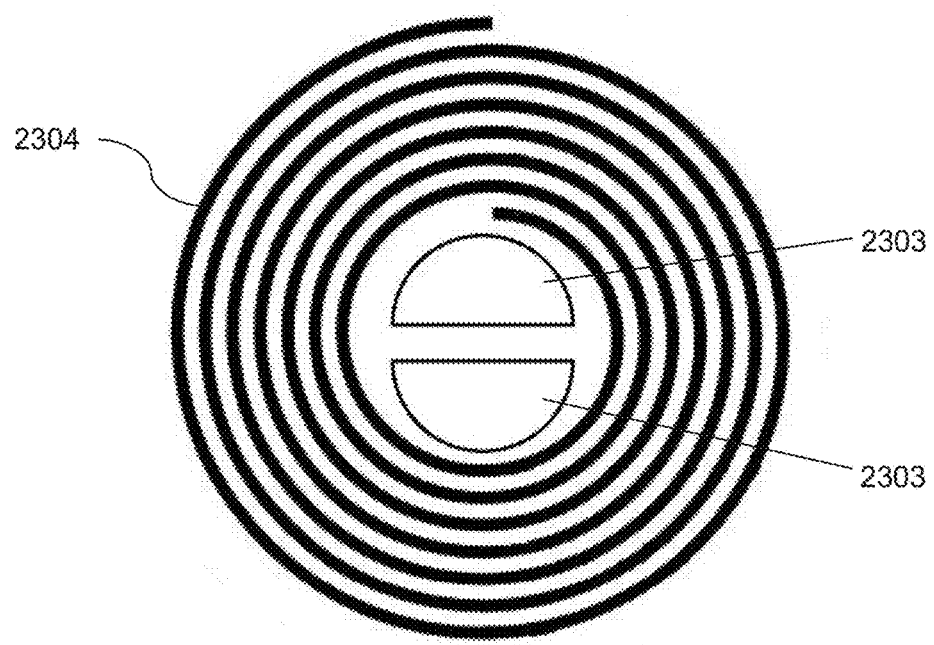

FIG. 23a illustrates an exemplary embodiment of the energy delivery element 2301 powered by LF generator. The energy delivery element 2301 may be winded around an electrode 2302 providing RF treatment. Preferably the energy delivery element may be winded around a plurality of electrodes. FIG. 23b illustrates an exemplary embodiment of the treatment device including two electrodes 2303 in the energy delivery element 2304 which is powered by LF generator. Alternatively at least two electrodes within the energy delivery element may be connected by an energy storage device. The energy storage device may be designed to be of low resistance value when high-frequency signal (frequency of RF signal) is provided and/or to be of high resistance when the low-frequency signal (frequency of magnetic signal) is provided. In the preferred embodiment the energy storage device may conduct as short-circuit when powered by high-frequency signal and as infinite resistor when power by low-frequency signal.

The treatment device may include a mathematic method including at least one of calculation and/or statistic method for monitoring correctness of the treatment and/or for monitoring the heat produced by the treatment device. The mathematic method may monitor at least one characteristic quantity of at least one operation parameter. The mathematic method may be used for determining heat generated by the energy delivery element. The generated heat may be used for additional heating biological structures in proximity. Alternatively, the energy delivery element may be less cooled to reach higher temperature for improved heating of the patient.

The applicator may be statically positioned to a pre-defined position to treat the target biological structure. Alternatively the applicator may be moveable during the treatment to treat larger area of the patient compared to treatment in static position. The RF energy transfer may be optimized prior to the treatment if the applicator is statically positioned and/or the treatment is provided in contact way. However, the continual optimizing of the energy transfer may be preferred for providing optimal and/or highly effective treatment to shorten the treatment duration, to improve the treatment effect and/or to achieve the desired results in shorter time period. Moreover the continual energy transfer optimizing may eliminate incorrect energy transfer caused by patient movement, e.g. caused by breath, and/or change of physiological conditions, e.g. caused by sweat, improved blood perfusion or increased temperature.

The treatment device may include a plurality of energy delivery elements, e.g. two, three, four or more. However, the even number of energy delivery elements may be used in the preferred embodiment. The at least two magnetic field device may provide a bipolar RF treatment, alternatively monopolar treatment may be provided as well. The bipolar treatment may provide homogenized temperature distribution in the target biological structure.

Figure 24:
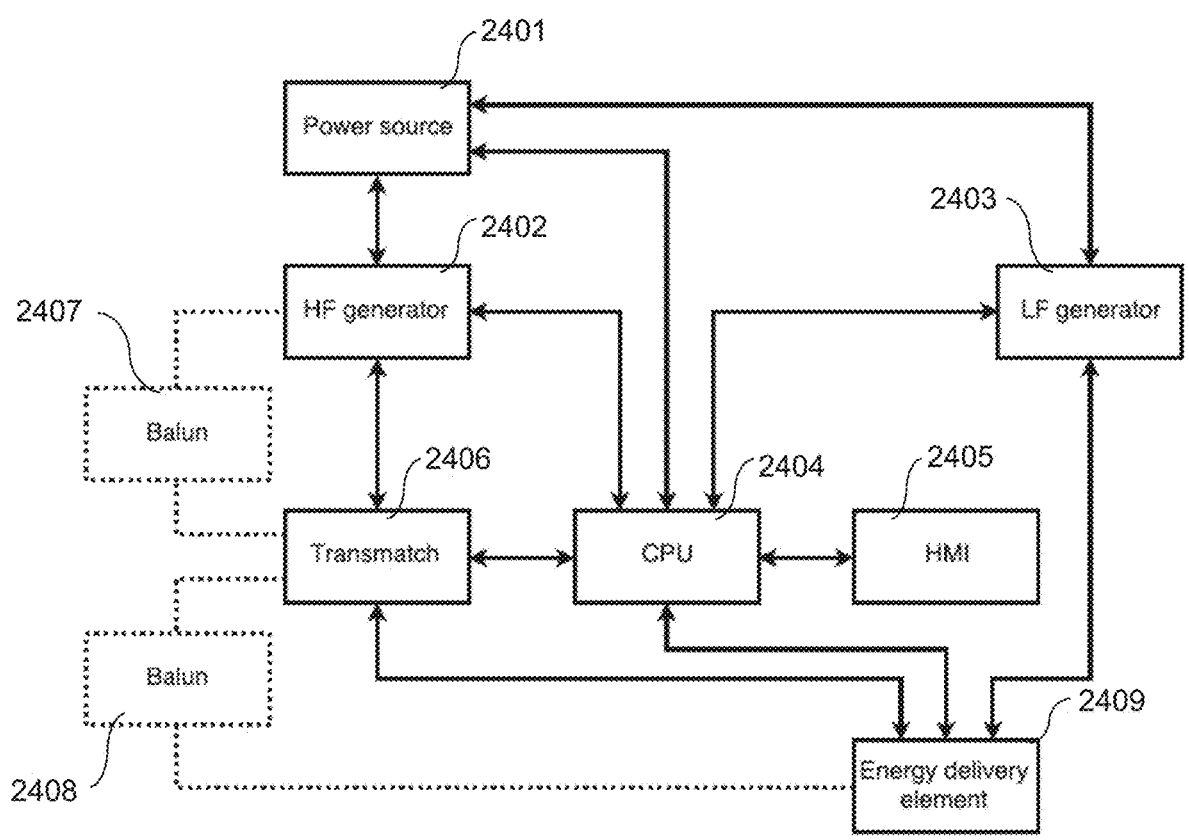
FIG. 24 illustrates a block diagram of treatment device including transmatch.

FIG. 24 illustrates the treatment device which may include a connection to a power supply, a power source 2401, high-frequency generator 2402, low-frequency generator 2403, control unit 2404, human machine interface 2405, transmatch 2406, balun 2407 and at least one energy delivery element 2409. The components illustrated by dotted line may be optional and may be excluded from the treatment device. According to alternative embodiment only one generator providing low and high frequency may be used. The arrows illustrate the direction of possible communication.

Transmatch may optimize the energy transfer to the patient. A function of balun is to transform unbalanced signal to balanced signal.

The power supply may provide energy for the treatment device via the power source 2401. The power supply may be external, e.g. a plug, or it may be integrally included within the treatment device, e.g. a battery. The power source 2401 may provide energy to electric components of the treatment device, particularly to both generators 2402, 2403 or to control unit 2404. The power source 2401 may communicate with control unit 2404 which may provide information about power necessary for the treatment. The power source 2401 may adjust the power for generators 2402, 2403 following the information from control unit 2404 or alternatively based on direct information from generator 2402 or generator 2403.

The control unit 2404 may communicate with LF generator 2402. LF generator 2402 may provide LF signal to at least one energy delivery element 2409 to generate magnetic treatment. The LF generator 2403 may provide information referred to treatment process to the control unit 2404, e.g. energy loss from one impulse. In an exemplary embodiment the control unit 2404 may send instruction to power source 2401 to provide the LF generator 2402 by the energy amount equaling the energy loss. Alternatively the control unit 2404 may control recharge of the LF generator.

The energy delivery element 2409 may include at least one sensor, e.g. a temperature sensor. The energy delivery element may provide information to control unit 2404, HF generator 2402 and/or to LF generator 2403.

The control unit 2404 may communicate with HF generator 2402 to provide instructions for HF generator 2402. HF generator 2402 may provide HF signal for at least one energy delivery element 2409 to generate RF treatment. The HF signal may be transferred via transmatch 2406. The HF generator 2402 may provide information referred to treatment process to the control unit 2404, e.g. temperature of the at least one energy delivery element 2409 and/or information provided by transmatch 2406. In exemplary embodiment RF energy transfer may be optimized prior to the treatment. However, the continual optimizing of the energy transfer may be preferred for providing optimal and/or highly effective treatment to shorten the treatment duration, to improve the treatment effect and/or to achieve the desired results in shorter time period. Moreover the continual energy transfer optimizing may eliminate incorrect energy transfer caused by patient movement, e.g. caused by breath, and/or change of physiological conditions, e.g. caused by sweat, improved blood perfusion or increased temperature. In an exemplary embodiment the HF generator 2402 may include an internal power source for adjusting energy for at least one energy delivery element 2409.

Alternatively, more than one energy delivery element 2409 may be used. When using two or more energy delivery elements, the at least one energy delivery element may deliver magnetic field, the at least one energy delivery element may deliver electromagnetic field (e.g. radiofrequency field); in still another embodiment each energy delivery element may provide both magnetic field and electromagnetic field (e.g. radiofrequency field) for magnetic and electromagnetic treatment.

The control unit 2404 may be in communication with human machine interface 2405. The human machine interface 2405 may include outputting interface for providing information for the operator and/or the patient. The outputting interface may include audio output, e.g. a speaker; visual output, e.g. a display or any combination. The outputting interface may provide a notification for the operator and/or the patient in a human perceptible form such as beep, flashing light, color change or mechanical signal.

The human machine interface 2405 may include at least one input element, e.g. touch member such as touchscreen, keyboard, control member for adjusting the treatment, for providing the information from operator. The operator may adjust e.g. a treatment protocol or may adjust treatment parameters following the patient's need.

The control unit 2404 may be in communication with transmatch 2406. The control unit 2404 may control the function of transmatch 2406. Transmatch 2406 may be provided by instructions from control unit 2404 to optimize the energy transfer to the patient. The transmatch 2406 may include an energy source to be able to adjust the energy provided to the at least one energy delivery element 2409.

In an alternative embodiment the transmatch 2406 may be excluded from the treatment device. The embodiment may be used for contact treatment or alternatively for contactless treatment. The energy transfer may be optimized prior the treatment.

In an alternative exemplary embodiment the transmatch may be the energy delivery element. The energy transfer may be optimized by adjusting e.g. transformation ratio.

The treatment device may include balun in various locations. In one exemplary embodiment unbalanced signal from HF generator 2402 may be transformed in the balun 2407 to balanced signal which further continues to transmatch 2406 and further to at least one energy delivery element 2409.

In an alternative exemplary embodiment the balun 2408 may be located in the transmatch 2406 or between transmatch and 33 and energy delivery element.

In alternative embodiment the balun may be excluded.

Figure 25A:
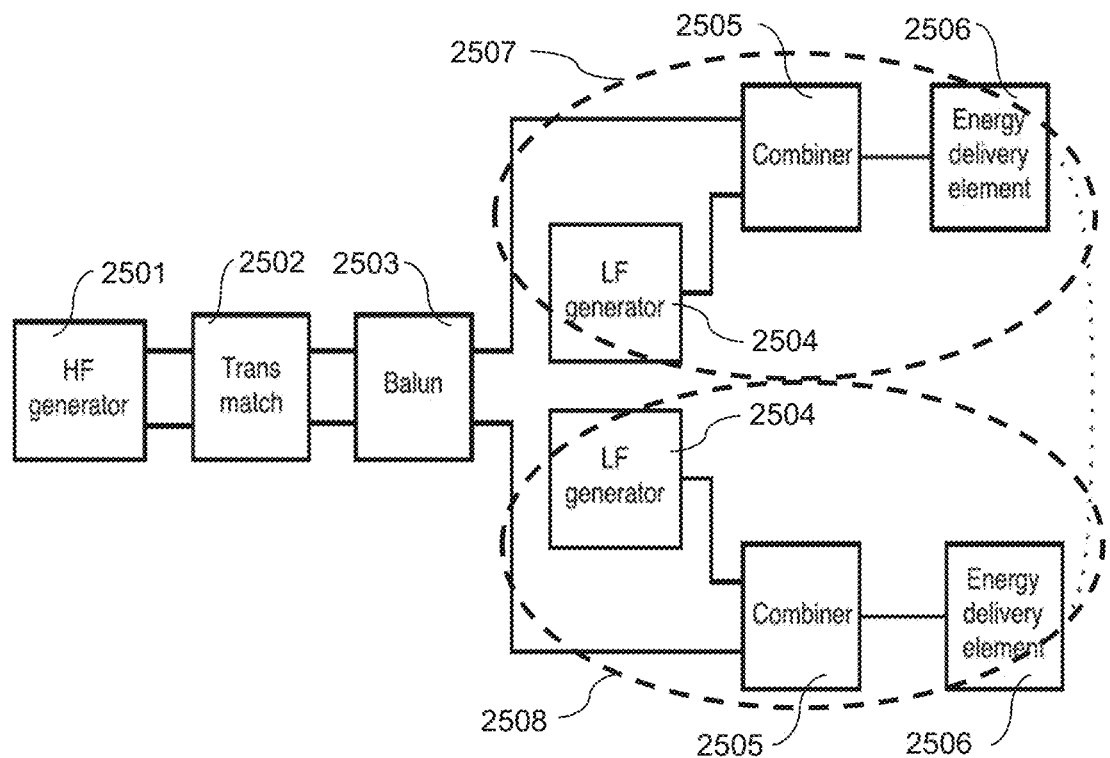
FIGS. 25a and 25b illustrate a block diagram of exemplary embodiments including a plurality of energy delivery elements.

FIG. 25a illustrates an exemplary embodiment of the treatment device using a plurality of energy delivery elements. In this particular exemplary embodiment, two energy delivery elements may provide both magnetic field and electromagnetic field (e.g. radiofrequency field) for magnetic and electromagnetic treatment. The treatment device includes high frequency generator 2501, transmatch 2502, balun 2503, low frequency generator 2504, combiner 2505, at least two energy delivery elements 2506.

The HF generator 2501 may provide HF signal to transmatch 2502 which may adjust the HF signal to optimize the energy transfer between the treatment device and the patient. The optimized HF signal may be directed to balun 2503 and to combiner 2505. In an alternative embodiment the balun 2503 may be incorporated in transmatch 2502 or may be between HF generator 2501 and transmatch 2502.

The at least one LF generator 2504 may provide LF signal to at least one combiner 2505. The combiner 2505 may provide both signals, from HF generator 2501 and from LF generator 2504, to energy delivery element 2506. The energy delivery element 2506 may provide energy to treat the target biological structure. In the particular embodiment the energy transfer (illustrated by dotted line) is defined by position of the energy delivery elements 2506. The energy transfer may be capacitive and/or inductive.

In the exemplary embodiment illustrated in FIG. 25a the treatment device includes two loops 2507, 2508 each including HF signal, LF signal, energy delivery element. In an alternative embodiment the treatment device may include one common LF generator for both loops 2507, 2508. According to alternative embodiment only one generator providing low and high frequency may be used.

The HF generator 2501 may provide HF signal to transmatch 2502 which may adjust the HF signal to optimize the energy transfer between the treatment device and the patient. The optimized HF signal may be directed to combiner 2505. LF generator 2504 may provide LF signal to combiner 2505. The combiner 2505 may provide both signals, from HF generator 2501 and from LF generator 2504, via balun 2503 to energy delivery element 2506. The energy delivery element 2506 may provide energy to treat the target biological structure. In the particular embodiment the energy transfer (illustrated by dotted line) is defined by position of the energy delivery elements 2506. The energy transfer may be capacitive and/or inductive.

In an alternative embodiment the exemplary treatment device may include one LF generator. According to alternative embodiment only one generator providing low and high frequency may be used.

Alternatively, the transmatch may be a incorporated in balun. The energy transfer may be optimized by e.g. adjusting transformation ratio.

Figure 25B:
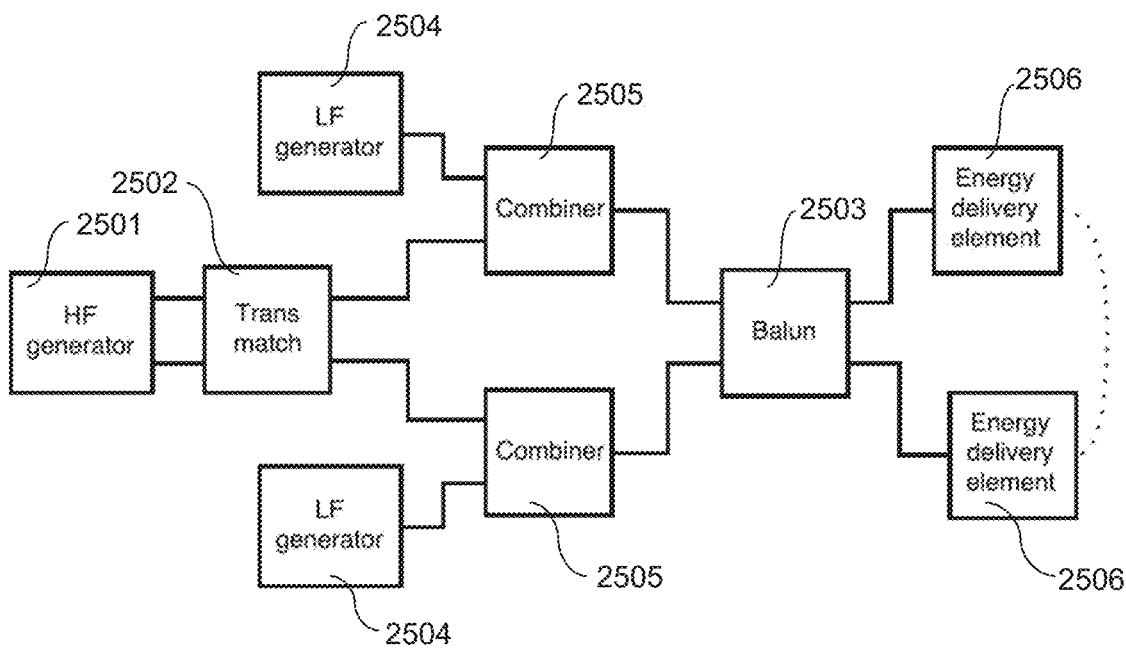

In still another exemplary embodiment with respect to FIG. 25a and FIG. 25b the combiners may be coupled. The coupling may be capacitive and/or inductive. Alternatively one combiner may be used. In another alternative embodiment the combiner may be excluded. The separation of the signals may be provided by mechanical layout of the energy delivery elements as described above.

The plurality of energy delivery elements may be positioned independently to each other to provide a treatment for the patient following the patient's needs. The position of the energy delivery element may be placed by the operator. The plurality of energy delivery elements may be in a plurality of applicators, e.g. each applicator includes at least one energy delivery element.

Figure 26A:
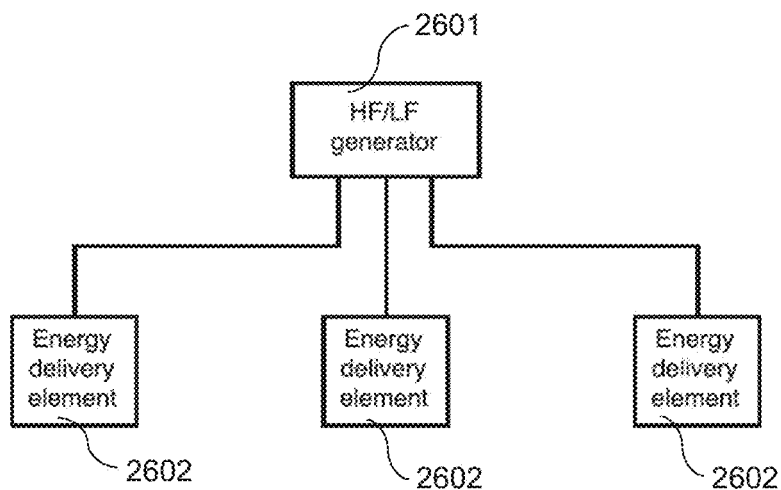
FIGS. 26a and 26b illustrate exemplary embodiments including a plurality of energy delivery elements with phase shift.
Figure 26B:
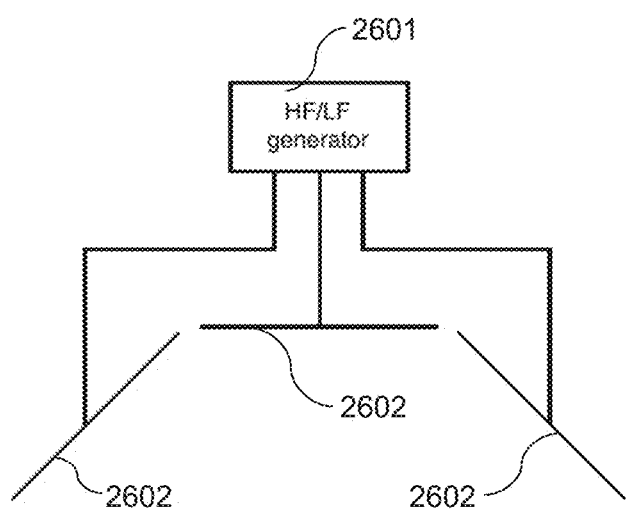

Alternatively the plurality of energy delivery elements may be positioned dependent to each other, preferably in a predefined pattern. The position of the plurality of the energy delivering elements may provide a treatment characterized by a phase shift. FIG. 26a illustrates an exemplary embodiment of the treatment with phase shift. The treatment device includes HF/LF generator 2601 for providing a signal for a plurality of energy delivery elements 2602. The signal for each energy delivery element may be phase shifted with respect to each other to generate a specific treatment profile which may be adjusted following the patient's needs. FIG. 26b illustrates an exemplary application. The HF/LF generator 2601 provides the signal for three energy delivery elements 2602 which may be preferably flat coils. The energy delivery elements are oriented with respect to each other. The HF signal may be provided to the energy delivery elements phase shifted to create a specific profile of the treatment. The phase shift may be e.g. 60°. The phase shift may be adjusted by the operator and/or by the patient following the patient's needs. In another alternative embodiment the phase shift may be dependent on the number of energy delivery elements.

The treatment device may include a plurality of applicators. Each applicator may include at least one energy delivery element. The applicator may be moveable during the treatment, the energy delivery element may be movable within the at least one applicator as well.

Alternatively the plurality of energy delivery elements may be positioned within one applicator having form of mechanical holder. The shape of the applicator having form of mechanical holder may be adjustable, e.g. the applicator may include at least one moveable part. In a preferred embodiment the applicator having form of mechanical holder may provide spatial arrangement of the energy delivery elements in one axis, two axes or three axes and/or provide tilting and/or rotation. The applicator having form of mechanical holder may provide fixation of the at least one energy delivery element in one position. The moveable parts may be connected by sliding mechanism and/or by a joint mechanism. The at least one part of the applicator may include at least one energy delivery element. The applicator may be adjustable following the treated area and/or biological structure.

The static position of the at least one applicator may be provided by a positioning member. The positioning member may be e.g. an arm or an adjustable flexible belt. The positioning member may include a buckle for adjusting the length of the belt. The applicator may be placed within predefined locations of the belt. Alternatively the applicator may be shaped to be moveable along the positioning member, e.g. the shape of the applicator may be preferably concave, e.g. V-shaped or U-shaped. The positioning member may be inserted itself into the concavity of the applicator. The position of the applicator may be adjusted by limited movement along the positioning member because the positioning member may be used as guiding member. However, the applicator may not be fixed to a particular static position. The position of the applicator may be dynamically adjusted during the treatment following the patient's needs. The position of the applicator may be adjusted manually by the operator, or automatically by the treatment device. In one exemplary embodiment a plurality of applicators may be used for treating larger body part, e.g. buttocks, abdomen or thigh.

Alternatively, the at least one energy delivery element, e.g. a coil, may be positioned below the at least one electrode. The energy delivery element may be positioned in between the electrode and the patient.

The at least one energy delivery element may influence at least one another energy delivery element while using the plurality of energy delivery elements. The correct treatment may be controlled via the mathematic method used for monitoring the at least one characteristic quantity of the operation parameter. The mutual positon of the energy delivery elements may be evaluated by the mathematic method as well. Hence the mathematic method may prevent providing the patient with incorrect treatment caused by incorrect position and/or orientation of at least two energy delivery elements. Furthermore the mathematic method may prevent the treatment device from affecting any conductive parts by the generated treatment, e.g. an additional heat may be generated.

The mathematic method may be further used for determining temperature and/or heat generated by at least one energy delivery element. Hence the mathematic method may be used for controlling a cooling of the energy delivery element, e.g. flow of the cooling media may be regulated. The heat generated by the energy delivery element may be further used for heating the patient.

The present device and method use a combination of non-invasive, preferably contactless, applications of different methods for enhancing human appearance. Particularly, the present invention uses a combined treatment by time-varying magnetic field and optical waves.

The treatment is defined by application of electromagnetic waves of wavelength in the range of 635 to 1100 nm, with maximal power flux density up to 100 W/cm². Alternatively, in the case of pulse light, the power flux density may be up to 100 W/cm² with light pulses lasting up to 300 ms, however, preferably in the range of 1 to 20 ms. Optical treatment may be used for inducing heat generation within the adipose cells over physiological temperature.

The treatment by optical waves may be combined with application of magnetic treatment inducing at least partial muscle contraction.

The presented methods enable aesthetic applications providing significant reduction of number and/or volume of adipose cells and cause circumferential reduction i.e. a reduction of the size of the treated body area. Furthermore, the treatment method induces at least partial muscle contraction to provide muscle toning, muscle shaping, body contouring, body shaping or skin tightening effect. Additionally, strong muscle contractions at high repetition rate may cause mechanical movement of all the layers in proximity of the contracted muscle. The method therefore may cause remodeling and/or neogenesis of the collagen and elastin fibers.

Optical treatment may selectively heat the target biological structure. Hence optical treatment may remove and/or remodel adipose tissue. Before/after, with some overlap or simultaneously the magnetic treatment of the target biological structure may induce at least partial muscle contraction within the target biological structure to remodel the adipose tissue by natural adipose tissue catabolism. Adipose tissue catabolism may be caused by apoptosis and/or necrosis of the adipocytes. The muscle contraction caused by induced eddy current is equivalent to a natural contraction. The adipose tissue may be reduced in natural way. Additionally, the muscle may be toned and/or shaped in a natural way. Therefore the effect resulting in body shaping and/or contouring may be significantly improved.

The present methods provide advanced approaches in aesthetic applications. Combined methods of treatment by optical treatment and treatment by magnetic field are used. The optical treatment may include treatment by optical waves. The magnet treatment may be provided by permanent magnets, electromagnetic devices generating a static magnetic field or preferably by magnetic devices generating time-varying magnetic field. In the preferred application the method may combine treatment by a pulsed magnetic field and optical treatment. The application is not limited by the recited combination so the combined method may include magnetic treatment and any treatment by electromagnetic field such as radiofrequency waves, e.g. microwaves, short waves or long waves.

The basic parts of the optical irradiation system include a hardware panel and an optical waves generating device or multiple optical waves generating devices. The optical waves generating device may be arranged in an array. The optical waves generating devices may be attached to each other or alternatively be individually mounted on dedicated supports. A scanning system may also be one of the options.

At least one optical wave generating device and a magnetic field generating device are provided. An optical treatment device may include at least one energy source and/or connection to the energy source, a hardware panel for controlling the optical treatment device and an optical waves generating device. Non limiting examples of optical waves generating device that may be used include light emitting diodes, lasers, laser diodes, different types of lamps and filtered lamps or combinations thereof. The treatment device may include at least one optical waves generating device, more preferably a plurality of optical waves generating devices of wavelength from ultraviolet, visible and infrared spectrum ranges. The wavelength may be in the range of 190 to 13000 nm, preferably in the range of 290 to 3000 nm, more preferably in the range of 400 to 1500 nm, even more preferably in the range of 550 to 1450 nm, particularly wavelengths about 915, 1064, 1208 and 1715 nm may be used.

The plurality of optical waves generating devices may generate optical waves simultaneously. The plurality of generated optical waves may interfere. Alternatively the plurality of optical waves generating devices may generate a plurality of independent optical waves at different times, preferably in sequences. The plurality of optical waves generating devices may be arranged in a predefined pattern within an applicator, e.g. in an array or a matrix.

The optical treatment applicator may be preferably external (e.g. hand-held). Alternatively, the optical treatment applicator may be an integral part of the optical treatment device (e.g. chair/bed implemented). Additionally, optical delivery elements, such as optical waveguides, light tubes or optical gel, may be used.

The magnetic treatment applicator may be an integral part of the treatment device, or it may be preferably external part of the treatment device (e.g. hand-held), alternatively the magnetic treatment applicator may be an integral part of the magnetic treatment device (e.g. chair/bed implemented).

According to one embodiment the magnetic treatment and optical treatment may be provided by at least two separate devices, i.e. at least one device for administering the magnetic treatment and at least one device for administering the optical treatment. The optical treatment may be applied to target biological structure prior, after or with some overlay with magnetic treatment. Alternatively optical treatment may be applied simultaneously with magnetic treatment. The time consequences of the treatment are described below.

Figure 27:
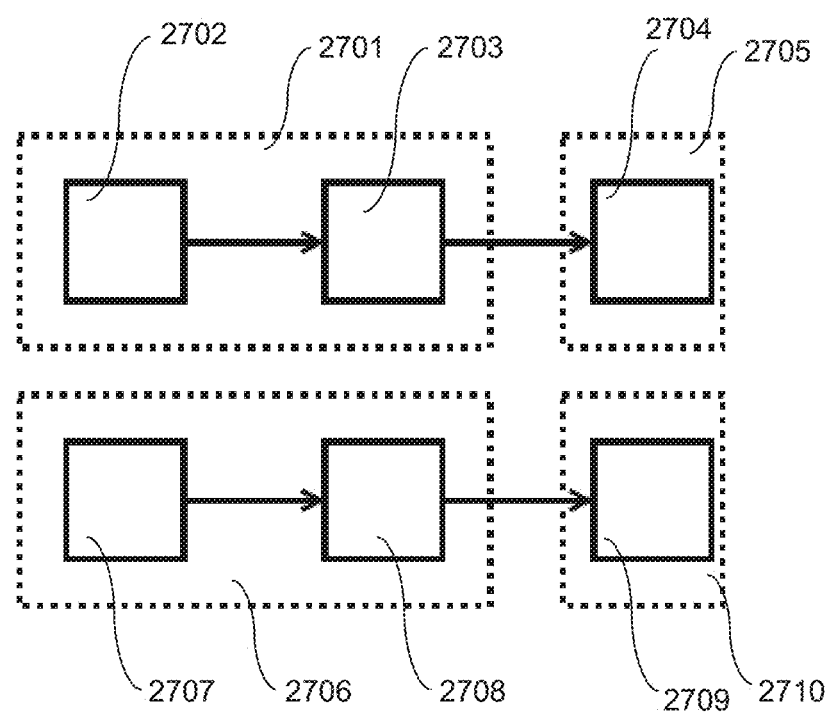
FIG. 27 illustrates a combined treatment administered by two separate devices.

FIG. 27 illustrates an exemplary embodiment providing combined treatment by magnetic field and optical treatment. The optical treatment is administered by optical treatment device 2701 (dotted line) including a connection to an energy source 2702 and a hardware panel 2703 for controlling the optical treatment. The hardware panel 2703 is connected with optical waves generating device 2704 within an optical treatment applicator 2705 (dotted line). The magnetic treatment is administered by magnetic treatment device 2706 (dotted line) including a connection to an energy source 2707 and a hardware panel 2708 for controlling the treatment by magnetic field. The hardware panel 2708 is connected with magnetic field generating device 2709 within a magnetic treatment applicator 2710 (dotted line).

In an alternative embodiment the at least one optical waves generating device may be in the treatment device. The optical waves may be delivered to the applicator and/or to the target biological structure by a waveguide.

Figure 28A:
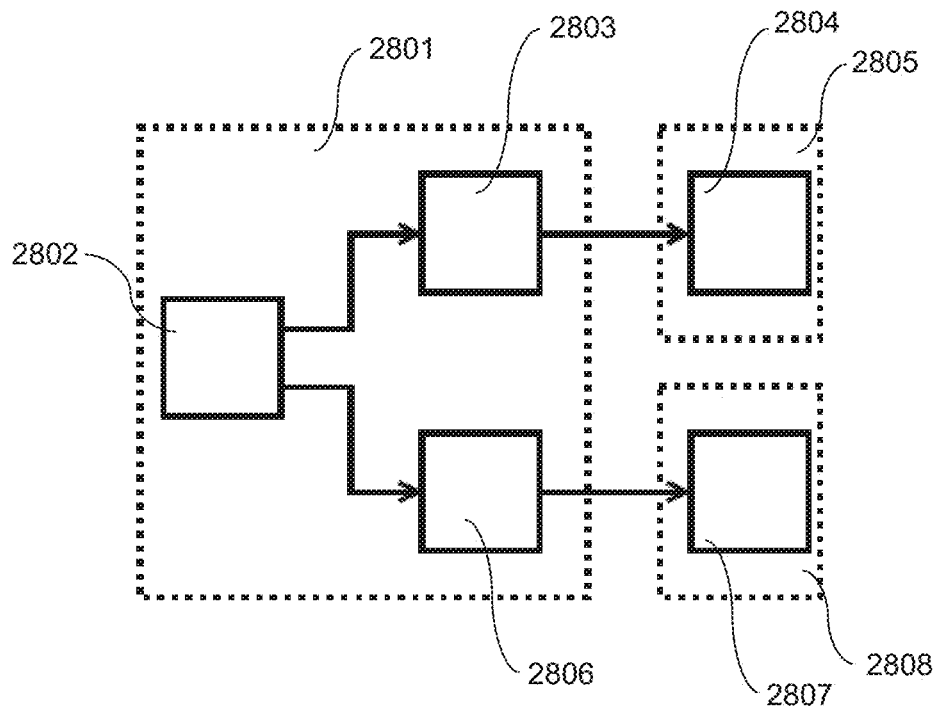
FIGS. 28a and 28b illustrate a combined treatment administered by one device including a plurality of applicators comprising magnetic field generating device or optical waves generating device.
Figure 28B:
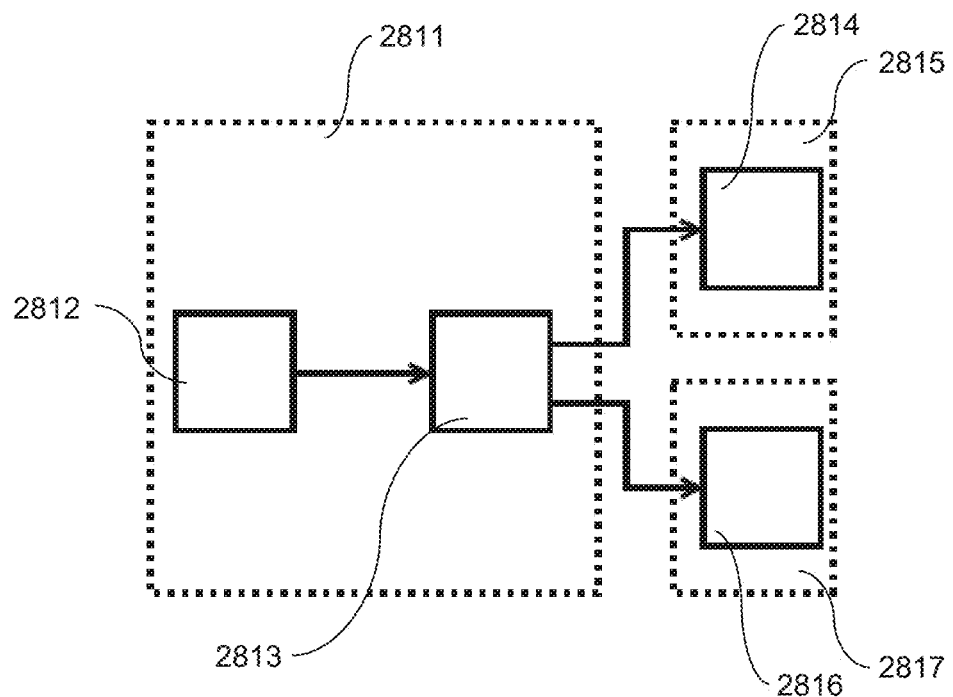
Figure 29A:
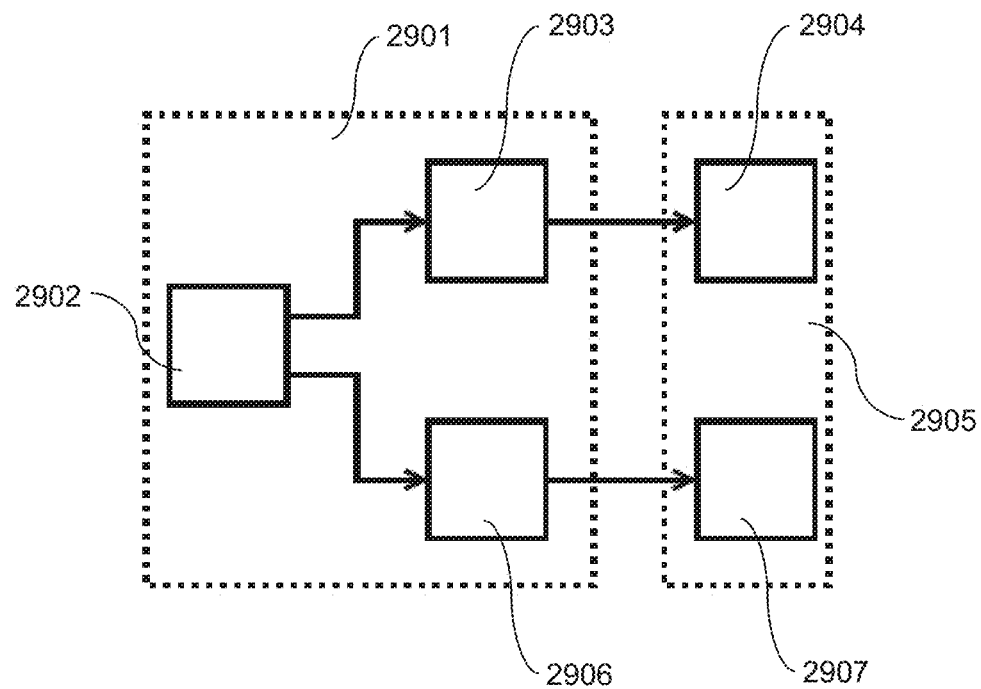
FIGS. 29a and 29b illustrate a combined treatment by one device including one applicator comprising at least one magnetic field generating device and at least one optical waves generating device.
Figure 29B:
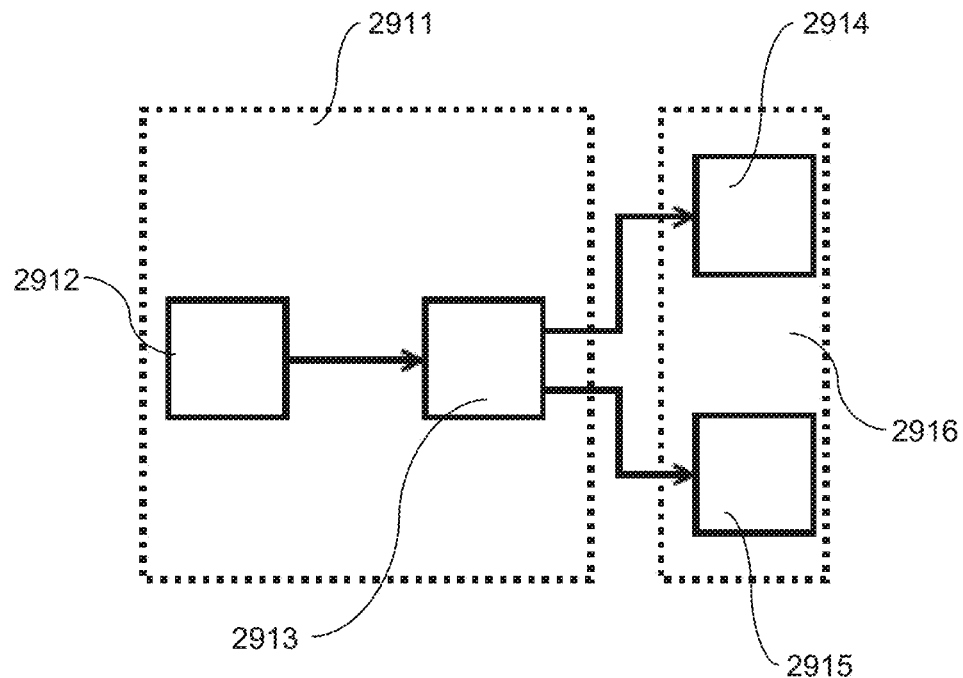

According to another embodiment the magnetic treatment and optical treatment may be provided by one device. The combined treatment provided by one device may be administered by at least one applicator. FIGS. 28a and 28b illustrate exemplary embodiments providing the combined treatment by two applicators providing different types of treatment, i.e. magnetic and optical treatment, to the target biological structure. FIGS. 29a and 29b illustrate exemplary embodiments providing the combined treatment by one applicator providing magnetic and/or optical treatment to the target biological structure.

FIG. 28a illustrates one exemplary embodiment of a combined treatment device providing magnetic and/or optical treatment by at least two applicators. The combined treatment device 2801 (dotted line) includes a connection to an energy source 2802 providing energy for a magnetic treatment and for an optical treatment. The optical treatment is controlled by a hardware panel for optical treatment 2803 which controls an optical waves generating device 2804 within an optical treatment applicator 2805 (dotted line). The magnetic treatment is controlled by a hardware panel for magnetic treatment 2806 which controls a magnetic field generating device 2807 within a magnetic treatment applicator 2808 (dotted line).

In an alternative embodiment the at least one optical waves generating device may be in the treatment device. The optical waves may be delivered to the applicator and/or to the target biological structure by a waveguide.

FIG. 28b illustrates another exemplary embodiment of a treatment device providing magnetic and/or optical treatment by at least two applicators. The combined treatment device 2811 (dotted line) includes a connection to an energy source 2812 providing energy for the magnetic treatment and/or for the optical treatment. Optical and/or magnetic treatments are controlled by a hardware panel 2813. The hardware panel 2813 controls an optical waves generating device 2814 within an optical treatment applicator 2815 (dotted line). Further the hardware panel 2813 controls a magnetic field generating device 2816 within a magnetic treatment applicator 2817 (dotted line).

In an alternative embodiment the optical waves generating devices may be in the treatment device. The optical waves may be delivered to the applicator and/or to the target biological structure by a waveguide.

FIG. 29a illustrates still another exemplary embodiment of a treatment device providing magnetic and/or optical treatment by at least one applicator. The combined treatment device 2901 (dotted line) includes a connection to an energy source 2902 providing energy for the magnetic treatment and/or for the optical treatment. The optical treatment is controlled by a hardware panel for optical treatment 2903 which controls an optical waves generating device 2904 within an applicator 2905 (dotted line). The magnetic treatment is controlled by a hardware panel for magnetic treatment 2906 which controls a magnetic field generating device 2907 within the applicator 2905 (dotted line). The applicator provides combined treatment.

In an alternative embodiment the optical waves generating devices may be in the treatment device. The optical waves may be delivered to the applicator and/or to the target biological structure by a waveguide.

FIG. 29b illustrates still another exemplary embodiment of a treatment device providing magnetic and/or optical treatment by at least one applicator. The combined treatment device 2911 (dotted line) includes a connection to an energy source 2912 providing energy for the magnetic treatment and/or for the optical treatment. Optical and/or magnetic treatment is controlled by a hardware panel 2913. The hardware panel 2913 controls an optical waves generating device 2914 and magnetic field generating device 2915 within an applicator 2916 (dotted line).

In an alternative embodiment the at least one optical waves generating device may be in the treatment device. The optical waves may be delivered to the applicator and/or to the target biological structure by a waveguide.

Figure 30A:
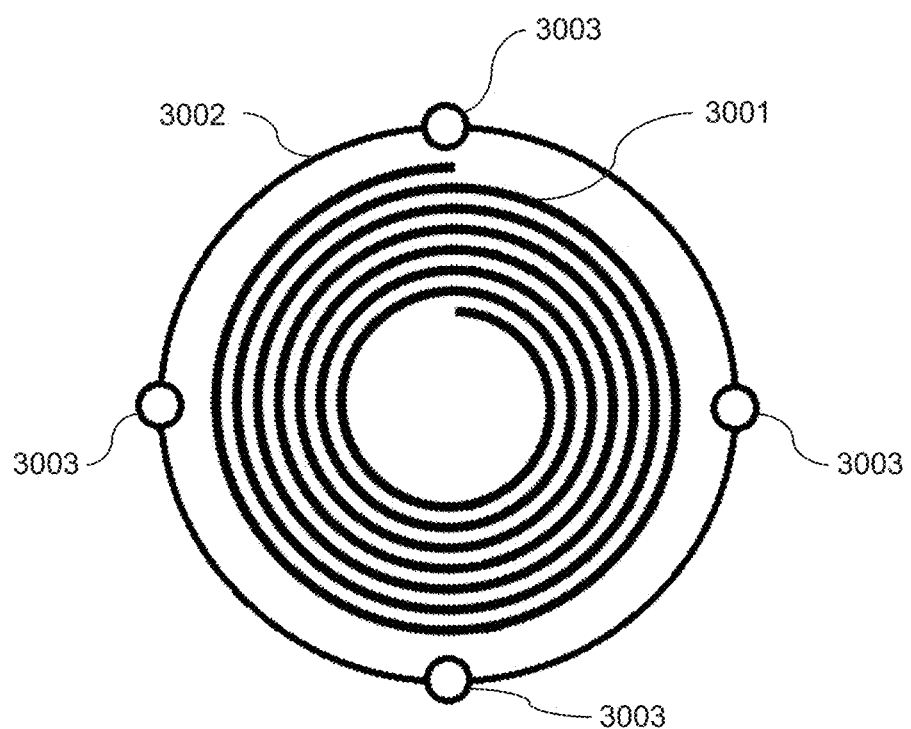
FIGS. 30a and 30b illustrate a combined treatment with optical waves generating device powered by magnetic field generated by magnetic field generating device.
Figure 30B:
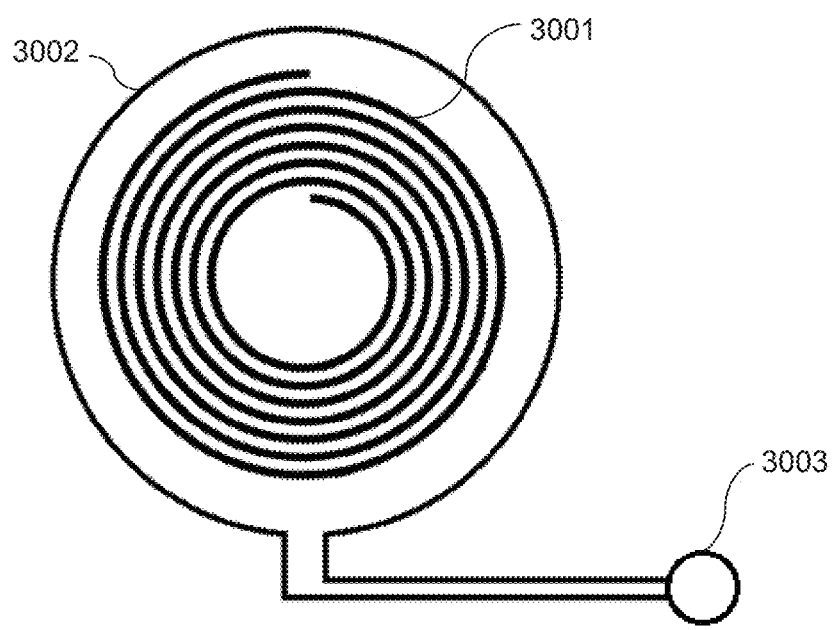

According to still another embodiment the magnetic field generating device may be used as an energy source for providing energy to another part of the treatment device, e.g. an optical waves generating device such as light-emitting diode (LED). FIGS. 30a and 30b illustrate exemplary embodiments of the magnetic field generating device which may be used as power supply. The magnetic field generating device 3001 may be surrounded by a conductor loop 3002. The time-varying magnetic field generated by magnetic field generating device 3001 induces eddy currents in the conductor loop 3002 within proximity of the magnetic field generating device 3001. The induced current in the conductor loop 3002 may be used for providing energy to another powered part of the treatment device, particularly in the applicator, or another treatment device, such as at least one optical waves generating device. FIG. 30a illustrates an exemplary embodiment of magnetic field generating device 3001 surrounded by a conductor loop 3002. The conductor loop 3002 may be connected to a plurality of optical waves generating devices 3003. FIG. 30b illustrates another exemplary embodiment of the magnetic field generating device 3001 surrounded by the conductor loop 3002. The conductor loop 3002 provides the energy to the optical waves generating device 3003. The optical waves generating device may be distanced from the conductor loop and may be external to the applicator including the magnetic field generating device 3001 and the conductor loop 3002.

Biocompatibility issues or hot spot generation may be overcome by transmitting electromagnetic energy into the target biological structure without physical contact with the patient. Contactless application of magnetic and/or optical treatments may provide sufficient passive cooling of the biological structure by circulating air.

In some indications, it may be advantageous to treat deeper adipose tissue by magnetic field simultaneously with the treatment of more superficial layers of the skin by optical waves.

An air gap or bolus material with high air permeability may be placed between the skin and the applicator. The material may be preferably transparent to the optical waves. This arrangement uses the human thermoregulatory system for cooling and avoids the need of artificial cooling of the skin. Optionally, the skin may be cooled via a stream of chilled or ambient temperature air. The human thermoregulatory system enables perspiration and other body fluids to evaporate and cool the surrounding skin. The application of electromagnetic waves is contactless. Therefore sweat accumulation and/or hot spot creation are avoided. Use of cooling fluids or gels is not necessary but may be optionally used. Cost of the treatment is reduced and patient comfort is improved. The applicator may be in direct or indirect contact with patient's skin. A bolus device may be used for providing indirect contact of the applicator with the target biological structure. A bolus may be filled with a material, preferably a fluid, influencing the propagation of the electromagnetic waves and/or homogenizing the temperature distribution of the patient's skin. Alternatively the bolus may deliver the electromagnetic waves to the target biological structure, e.g. a waveguide.

Cooling may be provided by positioning an air moving device proximate to the skin. The air moving device may be attached to or implemented into the applicator. Air moving device may be any kind of fan, ventilator or blower. The blower may include an air tube connected to air source for moving air through the air tube to the patient's skin. The air source may alternatively be cooled to provide cooled air. Alternatively, air suction may be also used as an active cooling method.

One or more applicators may move in the vicinity of the patient's body. The movement may be provided in various speed and/or acceleration. It may be moved in at least one direction, e.g. longitudinal, vertical, transversal or different axis and/or by rotational movement around any direction. Plurality of applicators may move in synchronized, randomized and/or independent manner. At least one applicator of the plurality of applicator may be static.

The homogeneity of treatment may be provided by the movement of the applicator. In one exemplary embodiment the applicator may move over and/or in different angle to the patient by rotational movement. In another exemplary embodiment the applicator may move in the vicinity of patient's skin. In still another exemplary embodiment the applicator may move to focus the treatment.

The movement of at least one applicator may provide a treatment pattern. The pattern may be, e.g. linear, wavy, circular, elliptical, zigzag, polygonal, oval, irregular and/or any combination thereof. In one exemplary application the at least one applicator may be positioned to the vicinity of thighs and the effect of treatment may be limited to these parts. In another exemplary application the at least one applicator may be positioned over the patient's abdomen to treat e.g. adipose cells.

The movement of the applicator may also provide a treatment to large body part, e.g. buttocks, abdomen or thigh.

The sensor may be connected with the hardware panel for controlling the optical treatment to adjust the power flux density applied to the biological structure to maintain the temperature of the target biological structure within treatment range. The temperature sensor also prevents the patient from any thermic damage.

Optical treatment may be used for remodeling, reducing the volume and/or number of adipose cells, body contouring or tightening skin, skin rejuvenation, wrinkles and/or stretch mark reduction, mole mark removal, tattoo removal, enhanced skin tightening, hair removal, treatment of vascular lesions, acne treatment, sweating reduction and other appearance improving and/or pain relief treatment without contacting the skin. The treatment may optionally be performed simultaneously or consecutively during the same session.

The commonly targeted skin chromophores are hemoglobin, melanin, carbon or tattoo ink. Alternatively water may absorb the optical waves. Each chromophore has unique absorption spectrum. The wavelength of the optical wave should match one of the absorption peaks of the targeted chromophore. The lasers or laser diodes work usually in pulse regime in these applications. The optical energy absorbed by the chromophore is converted to thermal energy thereby destroying the targeted cells. Selection of the best adapted wavelength, power and pulse duration allows achieving optimal effect on targeted biological structure with minimal effect on surrounding tissue.

The application of optical treatment may be improved by application of exogenous chromophores to the target biological structure. The exogenous chromophores may be applied in form of topical lotion, or may be delivered to the target biological structure by micro-invasive or invasive way such as injected.

According to the parameters of the optical waves used, different layers of the skin and different biological structures may be selectively treated. Various wavelengths, powers, pulse durations and repetition rates of electromagnetic radiation are applicable to provide the advantage of vast variability of penetration and absorption parameters. The operator may also adjust the optimum treatment time for each wavelength and the time sequences of treatments by different wavelengths, while some of them may overlap in time. In this way, a tailor-made solution for each patient and each indication is available. The treatment may be highly selective to reduce or avoid damage of the surrounding tissues.

Combinations of a plurality of optical waves generating devices allow performing the treatment of plurality of target biological structures at the same time and/or treating the same target tissue simultaneously by different means, which optimizes the doses of radiation applied. This diversification may also eliminate the risk of overheating, as the optical treatment with parameters leading to no or negligible thermic effect may be used. As a result, the risk of heat damage may be considerably reduced.

If the patient has more imperfections to be treated situated in the same body areas, it is also possible to treat them simultaneously by different types of electromagnetic waves. Each of the electromagnetic waves may be adjusted to optimum parameters for the target biological structure imperfection treatment. Thus the time of patient and of the operator is reduced, reducing the treatment cost.

The optical waves thermal effect may lead to temperature increase in the dermal and the sub dermal tissues also affects the triple-helix structure of collagen fibers contained in such tissues. This may result in remodeling and rejuvenation of collagen, increase of skin density and dermal thickening based on neocollagenesis. Skin tightening may also be achieved. In one aspect, the present methods selectively treat deep human tissue containing low volume of water, such as adipose tissue. Optical energy is provided to the skin by optical waves generating device. Remodeling and reducing the volume and/or number of adipocytes or skin tightening in the targeted areas may change the overall appearance of the body. Therefore it may be used for body contouring, body shaping and cellulite treatment.

Optical energy may be provided to the skin by at least one optical waves generating device in pulse or continuous mode. Optical energy is provided through the skin to the underlying dermal and/or subdermal tissue, without contacting the skin. The radiant energy may be converted inside the target tissue to heat. The radiant energy enables treating of the adipose tissue and/or collagen tissue, accelerating apoptosis and/or cell lysis (e.g. adipose cell), based on amount of energy transmitted to target biological structure. At the same time the triple helix structure of collagen fibers may result in remodeling and/or rejuvenation of collagen, increase of skin density and dermal thickening based on neocollagenesis. In an alternative embodiment the radiant energy enables treating of target tissue resulting e.g. in neocollagenesis without adipose tissue reduction. Target tissue may be remodeled and/or reduced and body contouring and/or skin tightening effect may occur.

Cooling may also be used to modify and to optimally adjust the depth of optical radiation penetration. Light penetration may be enhanced if cooling is used before phototherapy. The effects of heating in terms of light penetration are the opposite.

Optical treatment may treat the same or different skin layers as the magnetic treatment. As mentioned above, optical treatment may also be used for multiple rejuvenation and appearance enhancing applications. Another important indication is drug-free and addiction-free pain relief in many conditions.

Non-limiting examples of optical therapies that may be preferably used in combination with the treatment by magnetic field according to the present invention are: low level light therapy (LLLT), photodynamic therapy (PDT), high power laser therapy (HPLT) or intense pulsed light (IPL). However, the scope of the invention is not limited only to these particular optical irradiation methods. Other electromagnetic waves may be used, e.g. a radiofrequency treatment. The power flux density of the optical wave therapy may be in the range to 0.1-100 W/cm$^2$, more preferably in the range to 0.5-50 W/cm$^2$, most preferably 0.5-20 W/cm$^2$.

Low-level light therapy is one of the methods of non-invasive rejuvenation with no or a very small thermal effect. LLLT may be effective throughout the visible, infrared and near ultraviolet spectrum ranges. The term low level refers the fact that the levels of energy or power densities are low compared to other forms of light treatment such as by lasers, which are applicable for cutting, thermal coagulation or thermal damage, such as ablation. Treatment energies in LLLT are limited to 0.1-20 or a few J/cm$^2$ and/or by a power of 1 mW to 500 mW per optical waves generating device. The depth of penetration of the low level light radiation depends on parameters of the optical waves generating device such as wavelength, operating mode, which may be pulse or continuous, the power output, the probe design and the treatment technique. The depth of penetration where the light still has therapeutic effects should match the depth of the desired zone to be treated. The penetration depth is lower than in HPTL, up to several tens of mm approximately. Due to the low levels of absorbed energy, the treated and surrounding biological structures are not heated and are not damaged. Although many wavelengths may be used, it is advantageous to use at least one beam in the visible spectrum so that the area of application on the patient's body may be easily determined by the operator.

LLLT uses either coherent optical waves generating devices such as lasers or laser diodes or non-coherent light sources including incandescent lamps, gas filled lamps, filtered lamps optimized for a particular wavelength, light-emitting diodes, etc. A combination of any types of optical waves generating devices may be also used, as well as a plurality of optical waves generating devices of the same type.

The photons emitted by the low level optical waves generating devices used in LLLT therapy may be absorbed by endogenous mitochondrial chromophores in skin. Consequently, many processes may be activated, e.g. electron transport, increased adenosine triphosphate (ATP) production, enhanced blood micro-circulation, collagen production increase, dermal matrix remodeling etc. LLLT may thus successfully treat a multitude of conditions that require stimulation of healing, acute/chronic pain relief or restoration of function. LLLT has beneficial effects on wrinkles, scars including acne scars, stimulating the scalp in hair treatment, healing of burns, skin tightening, anti-oedematous effects, regeneration after sport etc. Inflammatory skin diseases such as psoriasis or acne may be also treated by the proposed treatment. In pigmentation disorders such as vitiligo, LLLT may increase pigmentation by stimulating melanocyte proliferation.

LLLT may influence also reduction of number and/or volume of adipose cells. It is believed that the incident optical waves produce transient pores in adipose cells, allowing lipids to leak out into the interstitial space of adipose tissue. If the parameters are appropriate, the pores close upon cessation of the energy application and the cell membrane returns to contiguity. The adipose cells are not destroyed, but temporary opening within the cell's membrane induced by the optical waves may provide a pathway for lipid to exit the cell and in the end also the patient's body. It may leads to the reduction of number and/or volume of adipose cells. This adipose cell number and/or volume reduction may restore proper adipose cells function thereby acting as an anti-diabetes mechanism.

It is advantageous to combine LLLT and magnetic treatment for safe and efficient target biological structure treatment.

While in LLLT the light is absorbed by endogenous cellular chromophores, PDT may be based on introduction of exogenous photosensitizers into the cells which are then irradiated with wavelengths of visible or near infra-red light. Photosensitizer drugs may become activated by one or several types of optical waves. The optimal type of optical waves depends on the target biological structure and the absorption peak of the particular chromophore drug used. PDT optical waves generating devices include laser, intense pulsed light, light-emitting diodes or many visible lights including natural sunlight, etc.

Unlike LLLT HPLT has pronounced thermal effects on the skin. HPLT lasers having an output of 500 mW or greater may be used for this treatment, with energy densities greater than 10 J/cm$^2$. High power allows extremely high penetration of the optical waves, in order of ten centimeters or even more, ensuring that the right dose actually reaches the target biological structure localized deep in the tissue. Laser may be precisely adjusted due to its monochromacy and coherency. Therefore its propagation and targeted biological structure may be finely pre-defined. Research shows that biological structures treated by HPLT are stimulated to increase production of adenosine triphosphate (ATP). Similarly to LLLT, the biological responses to increased ATP production may include reduction of inflammation, reducing scars, increased cell metabolism, improved vascular activity, and accelerated healing. It may improve regeneration after sport. Significant improvements of many post-traumatic pathologies or osteoarthritis have been noted, as well as temporary relief of stiffness and muscle spasms. It is important to note that HPLT also may provide the patients with drug-free and addiction-free acute and/or chronic mediation of pain, by decreasing inflammation and/or swelling and by increasing the release of endorphins and enkephalins. Moreover, if a pulse regime is applied, the wavelength-specific photomechanical wave generated in the tissue may stimulate free nerve endings, thus blocking pain pathways in the nervous systems and bringing immediate pain relief.

High power lasers, laser diodes or intense pulse light sources (IPL) may be also used for treating pigmented targets in the skin by selective photothermolysis. Such high power lasers reaching sufficient power density to vaporize illuminated cells may be gas lasers such as $CO_2$ or excimer laser, solid-state lasers such as rubin, Nd:YAG or Er:YAG laser, semiconductor lasers, dye lasers such as Rhodamin 6G laser etc.

IPL may be used also for other skin treatments with therapeutic or rejuvenating effects, sharing some similarities with high power laser treatment. In both cases, optical waves are used to destroy the target. But unlike lasers that use a single wavelength of light which typically matches only one chromophore, and hence only one condition, IPL uses a broad spectrum of wavelengths. When used with filters, it may be adapted to treat various conditions. This may be achieved when the IPL operator selects the appropriate filter that matches a specific chromophore. Such filter may be represented by an optical material filtering e.g. 480 nm, 530 nm, 560 nm, 640 nm or 690 nm.

The optical energy flux density of the IPL treatment may be in the range of 1 and 50 $J/cm^2$, preferably in the range of 2 to 40 $J/cm^2$, more preferably at least 5 J/cm2, or up to 100 $J/cm^2$. The optical waves may be applied continually or in pulses. Pulse width is time duration that the target is exposed to the optical waves, it is measured in milliseconds. Pulse width is shorter than thermal relaxation time of the target, i.e. the pulse width is long enough to allow heating of the target but also short enough that the target is able to cool so that there is no heat buildup in surrounding skin and tissue. The pulse width may be in the range of 1 to 300 ms, preferably in the range of 5 to 50 ms, most preferably up to 30 ms.

Optical waves may penetrate the skin and increase the temperature of adipose cells and thermally damage the adipose cells. Hence the optical treatment may be used for reducing number and/or volume of adipose cells, remodeling treated body parts, or improving the skin appearance. The target biological structure, e.g. adipose cells, may be exposed to increased temperature. The temperature may be in the range of 37.5 to 60° C., more preferably in the range of 40 to 50° C., most preferably in the range of 42 to 47° C., or up 80° C. The damaged adipose cells may be removed by blood and/or lymphatic system to be metabolized. The heat generated in the target biological structure may induce a production of growth factors and/or fibroblasts which may improve collagen neogenesis and/or new vein formation to support the newly generated collagen formations.

Optimal wavelength should include low absorption within the skin, i.e. low absorption of water and/or melanin, and high absorption within the adipose cells. The optical waves may be in visible or in IR spectrum such as near-IR spectrum, e.g. in the range of 600 to 1500 nm in a plurality of applicable bands e.g. in the range of 635 to 680 nm, particularly 658 nm; or in the range of 780 to 980 nm, particularly 800 nm or 940 nm; or in the range of 1050 to 1100 nm, particularly 1060 nm due to relatively high penetration through the skin. Alternatively the optical waves may be in the range of 1300 to 1450 nm, particularly 1320 and 1440 nm may be applicable.

The optical treatment may last up to 120 minutes, preferably in the range of 1 to 60 minutes, more preferably in the range of 20 to 40 minutes. The treatment time may be dependent on BMI of the patient. The power flux density of the optical treatment may be up to 50 $W/cm^2$, preferably up to 25 $W/cm^2$, more preferably in the range of 1 to 15 $W/cm^2$, most preferably in the range of 2 to 10 $W/cm^2$ such as at least 5 W/cm2. In the preferred application power modulation may be used.

Optionally, active cooling may be included. However, in many cases, auto thermoregulation by sweating is sufficient. The active cooling may be administered in continual mode or in pulsed mode to maintain the skin temperature within physiologic temperature, i.e. around or below 37° C.

Alternatively, optical treatment by high power optical waves generating device may be used for treatment of incontinence or menorrhagia. One exemplary application may be inserting the optical wave generating device into the body cavity, e.g. a vagina, and treating the target biological structure by selectively heating. A suitable probe may be used for inserting the optical waves generating device. The target biological structure may be tightened due to increased temperature and/or improved collagenesis. Alternatively the optical wave generating device may be external to the body cavity and the optical waves may be delivered to target tissue by optical delivery element.

An exemplary application of application combined treatment by optical waves and magnetic treatment may be application to enhancing appearance of genitalia, e.g. external female genitalia such as labia minora, labia majora and/or clitoris. Furthermore collagenesis may be improved in vagina hence it may be smoother and/or firmer. Therefore the combined treatment may enhance physical pleasure during coitus.

Optimal wavelength of the optical waves may be in the range of 400 to 600 nm, particularly around 500 nm. Energy density may be up to 25 $J/cm^2$, more preferably up to 10 $J/cm^2$, most preferably in the range of 1 to 8 $J/cm^2$. Treatment may be administered in continual or preferably in pulsed mode.

Alternatively, the application of optical waves may provide disinfection effect. Such application may include application of UV light, e.g. UV-B and/or UV-C light. The wavelength of the optical waves may be in the range of 200 to 300 nm, most preferably in the range of 250 to 270 nm. The optical radiation may destroy the DNA of microorganisms such as bacteria, or virus. The nucleic acid in DNA may form a covalent bond (such as thymine dimer) preventing unzipping process during reproduction cycle. Hence the replication ability of the microorganism is disabled and the microorganism may die and the infection may be treated. The power density may be up to 300 mW/cm2, preferably up to 200 mW/cm2, or in the range of 1 to 50 mW/cm2, more preferably in the range of 5 to 25 mW/cm2 In one exemplary application the UV light may be in external flow-chamber to provide disinfected air to the treated area.

Similar application of optical waves may be used for cleaning the skin of the patient.

The treatment by a combination of magnetic field and optical waves significantly improves the treatment effect. Most preferably, the optical waves include wavelengths ranging from 405 to 1500 nm. At least one optical waves generating device and at least one magnetic field generating device may be used.

The methods described are more gentle and efficient in adipose cells treatment or skin tightening since the target biological structure is treated by magnetic and/or by electromagnetic field.

The application of magnetic and optical treatment may be used for treatment of pelvic floor area disorders, e.g. gynaecologic and/or urologic issues such as incontinence. The magnetic treatment may be targeted to the area of pelvic floor to treat pelvic floor muscles. The repetition rate of the magnetic pulses may be in the range of 1 to 150 Hz, preferably up to 100 Hz, more preferably in the range of 5 to 70 Hz, e.g. at least 30 Hz. The optical treatment may selectively raise a temperature in the vagina to provide tightening effect. Alternatively the optical treatment may provide biostimulation effect to promote neocollagenesis.

The tightening effect may be also promoted by at least partial muscle contraction. Hence the treatment of incontinence may be provided by different energy types. The collagenesis may be improved by application of magnetic treatment improving local metabolism by improved blood flow and/or at least partial muscle contraction.

Another application of magnetic and optical treatment may be used for treating a pain. The pain relieving effect may be combined and significantly improved due to different applied energies and different approaches of relieving the pain. The pain relief is drug-free and may last up to several hours after the treatment. The pain relieving may be applied for treatment of chronic and/or acute pain. Alternatively, the pain relieving effect caused by magnetic and/or optical treatment may be used for improving acceptability of optical treatment provided by high power density optical radiation, e.g. high power laser or IPL.

Still another application of magnetic and optical treatment may be used for causing relaxing effect. High efficient relaxation may be caused by combined influence optical and magnetic treatment on the biological structure.

Still another application of magnetic and optical treatment may be used for treating the adipose cells. The adipose cells may be heated by the optical treatment above 37.5° C., more preferably above 40° C., most preferably in the range of 40 and 50° C., or up to 60° C. The temperature increase may induce apoptosis and/or necrosis of the adipose cells. The apoptosis of the adipose cells may be preferred effect due to reduced risk of inflammation and/or panniculitis occurrence. The temperature increase may also liquefy the adipose tissue. The magnetic treatment may contribute the optical treatment by inducing the at least partial muscle contraction which may improve the local blood and/or lymph circulation and/or local metabolism. Hence the death adipose cells may be removed faster from the human body. The apoptosis of the adipose cells may be also contributed by the influence of the magnetic treatment to metabolism of Ca ions as was described before. The optical waves may be in visible or in IR spectrum such as near-IR spectrum, e.g. in the range of 600 to 1500 nm in a plurality of applicable bands e.g. in the range of 635 to 680 nm, particularly 658 nm; or in the range of 780 to 980 nm, particularly 800 nm or 940 nm; or in the range of 1050 to 1100 nm, particularly 1060 nm due to relatively high penetration through the skin. Alternatively the optical waves may be in the range of 1300 to 1450 nm, particularly 1320 and 1440 nm may be applicable.

The optical treatment may last up to 120 minutes, preferably in the range of 1 to 60 minutes, more preferably in the range of 20 to 40 minutes. The treatment time may be dependent on BMI of the patient. The power flux density of the optical treatment may be up to 50 W/cm$^2$, preferably up to 25 W/cm2, more preferably in the range of 1 to 15 W/cm$^2$, most preferably in the range of 2 to 10 W/cm$^2$ such as at least 5 W/cm$^2$. In the preferred application power modulation may be used.

Still another application of magnetic and optical treatment may be used for treating the cellulite. As was mentioned above the adipose cells may be influenced by apoptosis and/or necrosis. Alternatively the adipose cells may be liquefied. The adipose cells metabolism may be contributed by the at least partial muscle contraction. Furthermore the application of optical treatment may heat the fibrous septae of the cellulite. The heated septae may be straightened by the at least partial muscle contraction caused by the magnetic treatment. Further the at least partial muscle contraction may remove the water from the cellulite tissue to reduce the cellulite. Therefore more significant results may be achieved in shorter time periods. The above mentioned methods may be combined hence the enhanced effect may be induced. Hence the results may be achieved in shorted time period and may be more significant.

Still another application of magnetic and optical treatment may be used for enhancing body shape and/or improving muscle tonus to enhance visual appearance of the body part. According to one application, the muscle may be treated by the optical treatment to increase the temperature of the muscle. Afterwards the heated muscle may be treated by magnetic treatment. The magnetic treatment may achieve more significant results due to increased temperature of the muscle. The muscle may be toned and/or strengthened more effectively. The toned and/or strengthened muscle may induce body shaping effect to enhance visual appearance of the treated body part. Moreover the results may be achieved without hours spent by exercising of the muscle which may achieve unpredictable results within different body parts. The effectiveness of the magnetic treatment may be enhanced by preheating of the muscle by optical treatment. Magnetic treatment may be provided at repetition rate of at least 0.1 Hz, more preferably at least 5 Hz, even more preferably at least 20 Hz, most preferably at least 50 Hz, or up to 700 Hz. The magnetic treatment may be preferably modulated.

Still another application of magnetic and optical treatment may be used for focused treating of specific muscle structures, e.g. buttocks. The demand for enhancing visual appearance of the buttocks has rapidly increased during last few years. The combined treatment may enhance the visual appearance of the buttocks by thermal effect caused by optical treatment and/or by muscle exercising effect by focus magnetic treatment. The magnetic treatment may be selectively focus to enhancing the visual appearance of the buttocks by shredding and/or toning of the buttock muscles such as gluteus maximus, medius and/or minimus.

Alternatively, the combined focused treatment may be used for causing breast lifting effect by preheating effect of the Cooper's ligament and following magnetic treatment with increased effectiveness. The treatment may lift the breasts up.

Still another application of magnetic and optical treatment may be used for skin rejuvenation. The optical treatment may be applied to cause micro-damages within the skin to promote the increase production and/or regeneration of collagen fibers. It may induce the enhanced visual appearance of the skin which may look well-toned, smoother and/or firmer. The optical treatment may be contributed by magnetic treatment causing at least partial muscle contraction which may induce the increase local metabolism and/or blood circulation. Hence the sufficiency of nutrients may be delivered to the target biological structure to promote its regeneration and/or production process.

Still another application of magnetic and optical treatment may be used for treating the wrinkles. The optical treatment may remove the wrinkles by resurfacing of the skin. Different wavelength may promote the growth of collagen and/or elastin fibers to provide the skin younger, firmer and/or smoother appearance. The optical treatment may be contributed by magnetic treatment causing at least partial muscle contraction which may induce the increase local metabolism and/or blood circulation. Hence the sufficiency of nutrients may be delivered to the target biological structure to promote its regeneration and/or production process.

The optical treatment may provide to the target biological structure the optical waves of wavelength in the range of 500 to 3000 nm, several wavelengths may be applicable for the treatment of wrinkles e.g. 590, 640, 695, 800, 1320 or 2940 nm. Alternatively other wavelengths may be also used. The energy delivered to the target biological structure may be up to 50 J/cm$^2$, more preferably up to 25 J/cm$^2$, most preferably in the range of 1 to 15 J/cm$^2$.

Still another application of magnetic and optical treatment may be used for treating the scars and/or stretchmarks. The optical treatment may enhance the visual appearance of scars and/or stretchmarks by providing improved the growth of collagen and/or elastin fibers to provide the skin younger, firmer and/or smoother appearance. The optical treatment may induce micro-damages to collagen and/or elastin fibers to promote their regeneration and/or production. The optical treatment may be contributed by magnetic treatment causing at least partial muscle contraction which may induce the increase local metabolism and/or blood circulation. Hence the sufficiency of nutrients may be delivered to the target biological structure to promote its regeneration and/or production process. Furthermore the at least partial muscle contraction may straighten the newly produced collagen and/or elastin fibers by massaging effect.

Still another application of magnetic and optical treatment may be used for lip visual appearance enhancing effect. The optical treatment may improve the growth of collagen and/or elastin fibers to provide younger, fuller, firmer and/or smoother appearance. The optical treatment may be contributed by magnetic treatment causing at least partial muscle contraction which may induce the increase local metabolism and/or blood circulation. Hence the sufficiency of nutrients may be delivered to the target biological structure to promote its regeneration and/or production process.

The above mentioned methods may be combined hence the enhanced effect may be induced. Hence the results may be achieved in shorted time period and may be more significant.

Optical treatment may be applied before the magnetic treatment. The effect of the optical treatment may be stimulating, e.g. increasing the temperature of the target biological structure to prepare a target biological structure to be treated by magnetic treatment inducing at least partial muscle contraction. To enhance the efficiency of the treatment in some indications, it may be advantageous to preheat the tissue by infrared radiation prior to magnetic treatment or combined magnetic and optical treatment.

Alternatively the effect caused by optical treatment may increase the temperature of the target biological structure, e.g. adipose cell or fibrous septae. It may be contributed by magnetic treatment causing at least partial muscle contraction. The at least partial muscle contraction may provide a massage effect for biological structures within proximity of the target biological structure, improve the blood and/or lymph circulation to improve local metabolism. Additionally the at least partial muscle contraction may reduce the number and/or volume of the adipose cells by energy used for the at least partial muscle contraction itself. Moreover, homogenous temperature distribution may be provided due to improved blood flow. Alternatively the at least partial muscle contraction may provide massage effect for promoting movement of fibrous septae.

Simultaneous application of combined magnetic and optical treatment may reach more significant results than separate use of these treatments.

Simultaneous application of magnetic treatment and optical treatment may be administered in two modes: a first mode may generate the magnetic pulses while optical treatment is active or second mode may generate magnetic pulses while the optical treatment is not in an active stimulation period, i.e. the period of magnetic treatment and optical treatment alternates.

The simultaneous application of magnetic treatment and optical treatment to the target biological structure may increase the peak magnetic component of the entire treatment resulting in improved heating of the target biological structure containing higher water volume, e.g. skin. Alternatively, the level of polarization of the optical radiation may be increased due to magnetic field, or a plane of polarization may rotate, e.g. Faraday's effect may occur. Due to increased temperature of skin, the production and/or remodeling of collagen and/or elastin fibers may be improved and the skin may be provided with a younger, smoother and enhanced appearance. The effect of overheating the muscle is reduced by the improved blood flow.

Optical treatment may also be used to attenuate the pain. Alternatively the repetition rate of the magnetic treatment may attenuate pain as well.

Optical treatment may be applied after the magnetic treatment to provide contributing effect such as analgesic effect or it may further improve local metabolism. The magnetic treatment may induce at least partial muscle contraction or to stimulate a muscle structure to increase a muscular tonus of the target biological structure. Both effects may provide a massage effect for biological structures within the proximity of the target biological structure hence the blood and/or lymph circulation may be improved to promote local metabolism. The temperature may be locally increased by the improved blood flow and the target biological structure may accept the following optical treatment at significantly higher efficiency. Hence the muscle may be heated at higher quality. Additionally, the collagen and/or elastin fibers may be remodeled or restored and/or its neogenesis may be improved to provide a younger, smoother and enhanced skin appearance.

Additionally, previous application of magnetic treatment may improve acceptability of the optical treatment. The magnetic treatment may provide pain relieving effect for the biological structure hence the thermic effect caused by the optical treatment may be more tolerable for the patient.

Another benefit may be releasing the adipose cells from the muscle by at least partial muscle contraction and/or by temperature increase causing improved metabolism of adipose cells. Still another benefit of the at least partial muscle contraction may be mechanic breaking large adipose cells bulks into smaller bulks which may be easier removed by the lymphatic and/or blood flow. The liquidity of the smaller adipose bulks may be contributed by application of optical treatment. Due to improved liquidity, improved metabolism and/or blood circulation the cellulite may be treated in a short time and the visual effect on skin appearance may be significantly enhanced.

Optical radiation may be also used to attenuate the pain after the magnetic treatment.

Combined treatments may be applied to one target biological structure to provide combined effect of magnetic and optical treatment. Alternatively the treatment may be applied to different target biological structures, e.g. optical treatment may be applied to at least adipose cell and magnetic treatment may be applied to at least one muscle fiber to improve local and/or adipose cell metabolism.

All applications of combined magnetic and optical treatment may amplify the resulting effect of the treatment. Therefore the results are achieved in significantly shorter time than the same results achieved by separate applications of the optical and magnet treatments. The treatment may be provided in various predefined treatment protocols focused on specific patient's needs, e.g. cellulite treatment, incontinence treatment, pain relieving etc. Each treatment parameter may be adjusted in the treatment protocol by the operator following the patient's needs. Alternatively the specific treatment may be designed by the operator for providing the most effective treatment following the patient's needs.

In still another application the combined treatment including magnetic treatment and mechanical treatment such as acoustic wave, ultrasound wave, shock wave treatment or massage treatment may be used for treatment of muscle issues. The mechanical treatment may be provided to the patient prior, during and/or after magnetic treatment.

Mechanical treatment refers to treatment by mechanical waves and/or acoustic waves and/or shock waves.

Mechanical treatment may be provided prior application of magnetic treatment. The mechanical treatment may induce microdamages in the target biological structure, e.g. a soft tissue such as a muscle. The microdamage may initiate and/or contribute a regeneration process of the target biological structure. The magnetic treatment may be applied consequently to improve blood flow within proximity of the target biological structure, local metabolism and/or to reduce lactate within the muscle. The magnetic treatment may provide relaxation effect.

Alternatively the mechanical treatment may be applied simultaneously with magnetic treatment. In an exemplary application the magnetic treatment may be applied to proximal part of the muscle to provide relaxation and/or pain relieving effect. The mechanical treatment may be applied to the distal part of the muscle. Such combined method may be applied for treatment of e.g. tendinopathy or tensor muscle tensor fascia latae pain syndrome.

Alternatively the mechanical treatment may be applied after magnetic treatment. The effects may be similar to simultaneous application of mechanical and magnetic treatment. In an exemplary application the combined mechanical treatment and magnetic treatment may be used for treatment of erectile dysfunctions. The mechanical treatment, e.g. a shock wave treatment, may be used for treatment of the erectile dysfunction. Afterwards the magnetic treatment may be provided to improve a blood flow within the pelvic floor, promote a sufficient amount of nutrients for the treated tissue, improve local metabolism and/or regeneration. The magnetic treatment may be applied by hand-held applicator and/or by applicator within the patient support.

A treatment device including a a high frequency generator, a low frequency generator, a combiner and an energy deliver element; wherein the at least one energy delivery element provides an electromagnetic treatment and a magnetic treatment for treating a biological structure.

A treatment device including a least one high frequency generator, at least one low frequency generator, a plurality of combiners and a plurality of energy deliver elements; wherein the plurality of energy delivery elements provides an electromagnetic treatment and a magnetic treatment for treating a biological structure.

A method of operating a treatment device comprising: generating a high frequency signal; and generating a low frequency signal; and delivering the high frequency signal and/or the low frequency signal to an energy delivering element; and providing by the least one energy delivery element an electromagnetic and/or a magnetic treatment.

Magnetic stimulation device producing time varying magnetic field for treatment, wherein device comprises: a connection to an energy source, a switch, a coil, an energy storage device, at least one blower and a casing; wherein the coil and the casing are arranged in a manner that fluid can flow in-between and wherein the coil is cooled by fluid flow over at least upper and lower sides of the coil.

Magnetic stimulation device producing time varying magnetic field for treatment, wherein device comprises: a connection to an energy source, a switch, a coil, an energy storage device; wherein the device enables achieve the repetition rates above 100 Hz with the magnetic flux density ensuring at least partial muscle contraction.

A method of operating a magnetic stimulation device including at least one applicator, at least one energy source, a plurality of switching devices, at least one energy storage device and a plurality of magnetic field generating devices, comprising: generating a plurality of peaks of magnitudes of magnetic flux density using a plurality of magnetic field generating devices.

A treatment device including at least one magnetic field generating device, an at least one applicator, wherein the at least one applicator includes at least one human machine interface.

A treatment device for treating a patient including at least one magnetic field generating device, an at least one applicator, at least one feedback information system including at least one sensor for determining an active biological response.

Thus, novel systems and methods have been described. Various changes and substitutions may of course be made without departing from the spirit and scope of the invention. The invention, therefore, should not be limited, except by the following claims and their equivalents.

The following additional applications are incorporated herein by reference:
U.S. Ser. No. 14/951,093 which was filed Nov. 24, 2016
U.S. Ser. No. 15/073,318 which was filed Mar. 17, 2016
U.S. Ser. No. 15/099,274 which was filed Apr. 14, 2016
U.S. Ser. No. 15/151,012 which was filed May 10, 2016
U.S. Ser. No. 15/178,455 which was filed Jul. 9, 2016
U.S. Ser. No. 15/344,811 which was filed Nov. 7, 2016
U.S. Ser. No. 15/396,073 which was filed Dec. 31, 2016
U.S. 62/357,679 which was filed Jul. 1, 2016
U.S. 62/440,912 which was filed Dec. 30, 2016
U.S. 62/440,905 which was filed Dec. 30, 2016
U.S. 62/440,922 which was filed Dec. 30, 2016
U.S. 62/440,936 which was filed Dec. 30, 2016
U.S. 62/440,940 which was filed Dec. 30, 2016

The invention claimed is:

1. A method of enhancing a visual appearance of a patient by applying a time-varying magnetic field using a treatment device which generates the time-varying magnetic field, the method comprising:
positioning a first applicator on a first area of a body region of the patient, the first applicator comprising a first magnetic field generating coil,
wherein the body region comprises one of thighs, buttocks, or abdominals;
positioning a second applicator on a second area of the body region, the second applicator comprising a second magnetic field generating coil,
wherein the first area of the body region differs from the second area of the body region,
wherein the first magnetic field generating coil and the second magnetic field generating coil are both flat and circular, and
wherein the first magnetic field generating coil and the second magnetic field generating coil each have the same inductance;

coupling the first applicator and the second applicator to the body region by a belt;
charging a first capacitor by a first energy source;
charging a second capacitor by a second energy source;
switching a first switching device to discharge the first capacitor to the first magnetic field generating coil to generate a first time-varying magnetic field with an impulse duration in a range of 10 µs to 700 µs, a repetition rate in a range of 1 Hz to 300 Hz, and a peak-to-peak magnetic flux density in a range of 0.4 Tesla to 7 Tesla on a surface of the first magnetic field generating coil,
  wherein the first time-varying magnetic field comprises biphasic impulses;
switching a second switching device to discharge the second capacitor to the second magnetic field generating coil to generate a second time-varying magnetic field with an impulse duration in a range of 10 µs to 700 µs, a repetition rate in a range of 1 Hz to 300 Hz, and a peak-to-peak magnetic flux density in a range of 0.4 Tesla to 7 Tesla on a surface of the second magnetic field generating coil,
  wherein the second time-varying magnetic field comprises biphasic impulses;
generating a first plurality of impulses of the first time-varying magnetic field with a first repetition rate and with an envelope modulated in a magnetic flux density, wherein the first repetition rate is constant;
generating a second plurality of impulses of the first time-varying magnetic field with a second repetition rate,
  wherein the second repetition rate is different from the first repetition rate, and
  wherein the second repetition rate is constant;
cooling the first magnetic field generating coil and the second magnetic field generating coil; and
generating a treatment protocol including the first time-varying magnetic field and the second time-varying magnetic field;
applying the treatment protocol to the body region to cause a muscle contraction such that the patient is simultaneously treated by the first time-varying magnetic field and the second time-varying magnetic field to enhance the visual appearance of the patient.

2. The method of claim 1, wherein the treatment device further comprises a first connecting tube comprising a first fluid conduit,
  wherein the treatment device comprises a second connecting tube comprising a second fluid conduit, and
  wherein the method further comprises directing a cooling media to the first applicator and directing the cooling media to the second applicator.

3. The method of claim 1, wherein the first time-varying magnetic field and the second time-varying magnetic field are each sinusoidal.

4. The method of claim 1, wherein the first applicator comprises a first fluid conduit disposed around a circumference of the first magnetic field generating coil, and wherein the second applicator comprises a second fluid conduit disposed around a circumference of the second magnetic field generating coil.

5. The method of claim 1, wherein the envelope is linearly increasing.

6. The method of claim 1, further comprising generating the first time-varying magnetic field independently of the second time-varying magnetic field.

7. A method of enhancing a visual appearance of a patient by applying a time-varying magnetic field using a treatment device which generates the time-varying magnetic field, the method comprising:
positioning a first applicator on a first area of a buttocks of the patient, the first applicator comprising a first magnetic field generating coil;
positioning a second applicator on a second area of the buttocks, the second applicator comprising a second magnetic field generating coil,
  wherein the first area of the buttock differs from the second area of the buttocks;
coupling the first applicator and the second applicator to the buttocks by a belt;
charging a first capacitor by a first energy source and charging a second capacitor by a second energy source;
switching a first switching device to discharge the first capacitor to the first magnetic field generating coil to generate an impulse of a first time-varying magnetic field with an impulse duration in a range of 10 µs to 700 µs, a first repetition rate in a range of 1 Hz to 300 Hz, and a peak-to-peak magnetic flux density in a range of 0.4 Tesla to 7 Tesla on a surface of the first magnetic field generating coil, wherein the impulse of the first time-varying magnetic field is sinusoidal;
establishing a first pulse of the first time-varying magnetic field,
  wherein the first pulse of the first time-varying magnetic field lasts for a time period, and
  wherein the time period lasts from a beginning of a first impulse of the first time-varying magnetic field to a beginning of a next consecutive impulse of the first time-varying magnetic field;
switching a second switching device to discharge the second capacitor to the second magnetic field generating coil to generate an impulse of a second time-varying magnetic field with an impulse duration in a range of 10 µs to 700 µs, a second repetition rate in a range of 1 Hz to 300 Hz, and a peak-to-peak magnetic flux density in a range of 0.4 Tesla to 7 Tesla on a surface of the second magnetic field generating coil,
  wherein the impulse of the second time-varying magnetic field is sinusoidal, and wherein a first impulse of the second time-varying magnetic field is generated during the time period of the first pulse of the first time-varying magnetic field;
generating a treatment protocol, including:
  a first plurality of impulses of the first time-varying magnetic field, the first plurality of impulses of the first time-varying magnetic field having a third repetition rate, wherein the third repetition rate is constant and wherein an amplitude of magnetic flux density of subsequent impulses of the first time-varying magnetic field linearly increases, and
  a first plurality of impulses of the second time-varying magnetic field, the first plurality of impulses of the second time-varying magnetic field having a fourth repetition rate, wherein the fourth repetition rate is constant and wherein an amplitude of magnetic flux density of subsequent impulses of the second time-varying magnetic field linearly increases;
cooling the first magnetic field generating coil and the second magnetic field generating coil; and
applying the treatment protocol to the buttocks to cause a muscle contraction to enhance the visual appearance of the patient.

8. The method of claim 7, wherein the first applicator and the second applicator are moveable along the belt.

9. The method of claim 7, wherein the treatment protocol further includes:
- a second plurality of impulses of the first time-varying magnetic field,
  - wherein the second plurality of impulses of the first time-varying magnetic field establishes a first rectangular envelope, and
- a second plurality of impulses of the second time-varying magnetic field,
  - wherein the second plurality of impulses of the second time-varying magnetic field establishes a second rectangular envelope.

10. The method of claim 7, wherein the first time-varying magnetic field and the second time-varying magnetic field each comprise biphasic impulses, and wherein the first magnetic field generating coil and the second magnetic field generating coil are each flat and circular.

11. The method of claim 7, wherein the third repetition rate is at least 20 Hz, and wherein the fourth repetition rate is at least 20 Hz.

12. The method of claim 11, further comprising generating each of the first time-varying magnetic field and the second time-varying magnetic field for at least 240 seconds.

13. The method of claim 7, further comprising generating the first time-varying magnetic field for a plurality of time periods, wherein at least two of the plurality of time periods have different repetition rates.

14. The method of claim 13, wherein the treatment protocol which further includes modulating each of the first time-varying magnetic field and the second time-varying magnetic field to generate a first trapezoidal envelope and a second trapezoidal envelope, respectively.

15. A method of enhancing a visual appearance of a patient by applying a time-varying magnetic field using a treatment device which generates the time-varying magnetic field, the method comprising:
- positioning a first applicator on a body region of the patient, the first applicator comprising a first magnetic field generating coil,
  - wherein the body region comprises at least one of a buttocks or an abdomen;
- positioning a second applicator on a second area of the body region, the second applicator comprising a second magnetic field generating coil;
- coupling the first applicator and the second applicator to the body region by a positioning member;
- adjusting at least one treatment parameter via a touchscreen interface;
- charging a first capacitor by a first energy source and charging a second capacitor by a second energy source;
- switching a first switching device to discharge the first capacitor to the first magnetic field generating coil to generate an impulse of a first time-varying magnetic field with an impulse duration in a range of 10 µs to 700 µs, a repetition rate in a range of 1 Hz to 300 Hz, and a peak-to-peak magnetic flux density in a range of 0.4 Tesla to 7 Tesla on a surface of the first magnetic field generating coil,
  - wherein the impulse of the first time-varying magnetic field is biphasic and sinusoidal;
- switching a second switching device to discharge the second capacitor to the second magnetic field generating coil to generate an impulse of a second time-varying magnetic field with an impulse duration in a range of 10 µs to 700 µs, a repetition rate in a range of 1 Hz to 300 Hz, and a peak-to-peak magnetic flux density in a range of 0.4 Tesla to 7 Tesla on a surface of the second magnetic field generating coil,
  - wherein the impulse of the second time-varying magnetic field is biphasic and sinusoidal;
- generating a plurality of impulses of each of the first time-varying magnetic field and the second time-varying magnetic field with a constant repetition rate and with an envelope modulated in an amplitude of magnetic flux density,
- generating the first time-varying magnetic field for a plurality of time periods;
- generating the second time-varying magnetic field for a plurality of time periods,
  - wherein at least two of the plurality of time periods of the first time-varying magnetic field have a first repetition rate and a second repetition rate, respectively, wherein the second repetition rate differs from the first repetition rate,
  - wherein at least two of the plurality of time periods of the second time-varying magnetic field have a third repetition rate and a fourth repetition rate, respectively, wherein the fourth repetition rate differs from the third repetition rate,
  - wherein the first repetition rate and the third repetition rate are the same, and
  - wherein the second repetition rate and the fourth repetition rate are the same;
- cooling the first magnetic field generating coil and the second magnetic field generating coil;
- applying the first time-varying magnetic field and the second time-varying magnetic field to the body region at same time to cause a muscle contraction to enhance the visual appearance of the patient.

16. The method of claim 15, wherein the first magnetic field generating coil and the second magnetic field generating coil are both flat and circular.

17. The method of claim 15, further comprising:
- coupling the first applicator to a first area of the buttocks and coupling the second applicator to a second area of the buttocks, wherein the first area is different from the second area; or
- coupling the first applicator to a first area of the abdomen and coupling the second applicator to a second area of the abdomen, wherein the first area is different from the second area.

18. The method of claim 15, wherein the positioning member is a belt.

19. The method of claim 18, further comprising generating a triangular envelope by the first magnetic field generating coil and the second magnetic field generating coil.

20. The method of claim 18, wherein the first applicator and the second applicator are moveable along the belt.

21. The method of claim 15, wherein the at least one treatment parameter is one of a magnetic flux density or a repetition rate.

22. A method of enhancing a visual appearance of a patient by applying a time-varying magnetic field using a treatment device which generates the time-varying magnetic field, the method comprising:
- positioning a first applicator on a buttocks of the patient, the first applicator comprising a first magnetic field generating coil;
- positioning a second applicator on the buttocks, the second applicator comprising a second magnetic field generating coil, wherein the second applicator is positioned independently of the first applicator;
coupling the first applicator and the second applicator to the buttocks by a belt;
charging a first capacitor and charging a second capacitor;
switching a first switching device to discharge the first capacitor to the first magnetic field generating coil to generate an impulse of a first time-varying magnetic field with an impulse duration in a range of 10 μs to 700 μs and a peak-to-peak magnetic flux density in a range of 0.4 Tesla to 7 Tesla on a surface of the first magnetic field generating coil,
   wherein the impulse of the first time-varying magnetic field is biphasic;
establishing a first pulse of the first time-varying magnetic field,
   wherein the first pulse of the first time-varying magnetic field lasts for a time period, and wherein the time period lasts from a beginning of a first impulse of the first time-varying magnetic field to a beginning of a next consecutive impulse of the first time-varying magnetic field;
switching a second switching device to discharge the second capacitor to the second magnetic field generating coil to generate an impulse of a second time-varying magnetic field with an impulse duration in a range of 10 μs to 700 μs and a peak-to-peak magnetic flux density in a range of 0.4 Tesla to 7 Tesla on a surface of the second magnetic field generating coil,
   wherein the impulse of the second time-varying magnetic field is biphasic, and
   wherein a first impulse of the second time-varying magnetic field is generated during the time period of the first pulse of the first time-varying magnetic field;
modulating the first time-varying magnetic field and the second time-varying magnetic field to establish a trapezoidal envelope generated by each respective magnetic field generating coil;
cooling the first magnetic field generating coil and the second magnetic field generating coil;
applying the first time-varying magnetic field and the second time-varying magnetic field to the buttocks and causing a muscle contraction to enhance the visual appearance of the patient.

23. The method of claim 22, wherein the first applicator is coupled to a first area of the buttocks and the second applicator is coupled to a second area of the buttocks, and wherein the first area of the buttocks is different from the second area of the buttocks.

24. The method of claim 23, wherein each of the first and second areas of the buttocks comprises one of a gluteus maximus, a gluteus medius, or a gluteus minimus.

25. The method of claim 22, further comprising:
generating the first time-varying magnetic field for a plurality of time periods;
generating the second time-varying magnetic field for a plurality of time periods,
   wherein at least two of the plurality of time periods of the first time-varying magnetic field have a first repetition rate and a second repetition rate, respectively, wherein the second repetition rate differs from the first repetition rate,
   wherein at least two of the plurality of time periods of the second time-varying magnetic field have a third repetition rate and a fourth repetition rate, respectively, wherein the fourth repetition rate differs from the third repetition rate,
   wherein the first repetition rate and the third repetition rate are the same, and
   wherein the second repetition rate and the fourth repetition rate are the same; and
modulating each of the first time-varying magnetic field and the second time-varying magnetic field in an amplitude of magnetic flux density.

26. The method of claim 22, wherein the first magnetic field generating coil and the second magnetic field generating coil are both flat and circular.

27. The method of claim 22, further comprising modulating the first time-varying magnetic field and the second time-varying magnetic field in a first repetition rate and a second repetition rate.

28. The method of claim 22, wherein the treatment device further comprises a first connecting tube comprising a first fluid conduit and a second connecting tube comprising a second fluid conduit, and wherein the method further comprises directing a cooling media by the first fluid conduit to the first applicator and by the second fluid conduit to the second applicator.

29. The method of claim 22, further comprising generating each of the first time-varying magnetic field and the second time-varying magnetic field with a repetition rate in a range of 1 Hz to 300 Hz.

* * * * *